United States Patent
Salamini et al.

(10) Patent No.: US 10,092,215 B2
(45) Date of Patent: Oct. 9, 2018

(54) DEVICES AND METHODS FOR VASCULAR NAVIGATION, ASSESSMENT AND/OR DIAGNOSIS

(71) Applicant: Piccolo Medical, Inc., San Francisco, CA (US)

(72) Inventors: Alexey Salamini, San Francisco, CA (US); Eric Yu, San Francisco, CA (US); Daniel R. Burnett, San Francisco, CA (US)

(73) Assignee: Piccolo Medical Inc., San Francisco, CA (US)

( * ) Notice: Subject to any disclaimer, the term of this patent is extended or adjusted under 35 U.S.C. 154(b) by 0 days.

(21) Appl. No.: 15/919,000

(22) Filed: Mar. 12, 2018

(65) Prior Publication Data

US 2018/0220931 A1 Aug. 9, 2018

Related U.S. Application Data

(63) Continuation of application No. PCT/US2017/038374, filed on Jun. 20, 2017.
(Continued)

(51) Int. Cl.
*A61B 5/05* (2006.01)
*A61B 5/06* (2006.01)
(Continued)

(52) U.S. Cl.
CPC ............... *A61B 5/065* (2013.01); *A61B 5/00* (2013.01); *A61B 5/0008* (2013.01); *A61B 5/01* (2013.01); *A61B 5/02* (2013.01); *A61B 5/028* (2013.01); *A61B 5/0275* (2013.01); *A61B 5/042* (2013.01); *A61B 5/6851* (2013.01); *A61B 5/6852* (2013.01); *A61B 6/00* (2013.01); *A61M 25/0026* (2013.01); *A61M 25/0102* (2013.01); *A61M 25/0105* (2013.01); *A61M 31/00* (2013.01);
(Continued)

(58) Field of Classification Search
CPC ..... A61B 5/065; A61B 5/6851; A61B 5/0008; A61B 5/6852; A61B 5/042; A61B 5/01; A61B 5/028; A61M 25/0026; A61M 25/0102; A61M 2025/0166
See application file for complete search history.

(56) References Cited

U.S. PATENT DOCUMENTS 3,748,623 A 7/1973 Millar
3,915,155 A 10/1975 Jacobson et al.
(Continued)

OTHER PUBLICATIONS

PCT Application No. PCT/US2017/038374 filed Jun. 20, 2017 in the name of TheraNova, International Search Report and Written Opinion dated Aug. 29, 2017.

*Primary Examiner* — Scott Getzow
(74) *Attorney, Agent, or Firm* — Levine Bagade Han LLP

(57) ABSTRACT

Devices and methods for vascular navigation, assessment and/or diagnosis are described which determine the location of the tip of a vascular catheter using the introduction of a medium with a measurable parameter (e.g., temperature, light reflection, sound reflection, etc.) and sensing and measuring the measurable parameter as the catheter is advanced. Measurements of the parameter are tracked over time, recorded and analyzed. The value of the parameter and/or the shape of the parameter value vs. time curve may be used in the analysis. For example, curve amplitude, variability, standard deviation, slope, etc. may be used in the analysis of catheter location.

30 Claims, 43 Drawing Sheets

Related U.S. Application Data

(60) Provisional application No. 62/444,941, filed on Jan. 11, 2017, provisional application No. 62/405,879, filed on Oct. 8, 2016, provisional application No. 62/356,383, filed on Jun. 29, 2016.

(51) Int. Cl.
*A61B 6/00* (2006.01)
*A61B 5/00* (2006.01)
*A61B 5/02* (2006.01)
*A61B 5/0275* (2006.01)
*A61M 31/00* (2006.01)
*A61B 5/01* (2006.01)
*A61B 5/028* (2006.01)
*A61B 5/042* (2006.01)
*A61M 25/00* (2006.01)
*A61M 25/01* (2006.01)
*A61M 25/09* (2006.01)

(52) U.S. Cl.
CPC ............ *A61M 2025/0166* (2013.01); *A61M 2025/09175* (2013.01)

(56) References Cited

U.S. PATENT DOCUMENTS

| | | |
|---|---|---|
| 4,380,237 A | 4/1983 | Newbower |
| 4,572,206 A | 2/1986 | Geddes et al. |
| 4,601,706 A | 7/1986 | Aillon |
| 4,798,588 A | 1/1989 | Aillon |
| 4,817,624 A | 4/1989 | Newbower |
| 4,841,981 A | 6/1989 | Tanabe et al. |
| 4,941,475 A | 7/1990 | Williams et al. |
| 5,037,396 A | 8/1991 | Streeter |
| 5,092,339 A | 3/1992 | Geddes et al. |
| 5,250,034 A | 10/1993 | Appling et al. |
| 5,427,114 A | 6/1995 | Colliver et al. |
| 5,900,726 A | 5/1999 | Brugger et al. |
| 5,989,192 A | 11/1999 | Weijand et al. |
| 6,050,972 A | 4/2000 | Zadno-Azizi et al. |
| 6,089,103 A | 7/2000 | Smith |
| 6,179,828 B1 | 1/2001 | Mottola et al. |
| 6,231,498 B1 | 5/2001 | Pfeiffer et al. |
| 6,551,250 B2 | 4/2003 | Khalil |
| 6,672,172 B2 | 1/2004 | Tulkki et al. |
| 6,704,590 B2 | 3/2004 | Haldeman |
| 6,743,208 B1 | 6/2004 | Coyle |
| 6,868,739 B1 | 3/2005 | Krivitski et al. |
| 6,909,919 B2 | 6/2005 | Jain et al. |
| 7,112,176 B2 | 9/2006 | Krivitski et al. |
| 7,121,150 B2 | 10/2006 | Krivitski et al. |
| 7,210,359 B2 | 5/2007 | Krivitski et al. |
| 7,275,447 B2 | 10/2007 | Krivitski et al. |
| 7,549,965 B2 | 6/2009 | Krivitski et al. |
| 7,771,363 B2 | 8/2010 | Thompson |
| 7,775,988 B2 | 8/2010 | Pijls |
| 8,147,486 B2 | 4/2012 | Honour et al. |
| 8,409,103 B2 | 4/2013 | Grunwald et al. |
| 8,480,648 B2 | 7/2013 | Burnett et al. |
| 8,632,469 B2 | 1/2014 | Kassab |
| 8,715,195 B2 | 5/2014 | Ziv |
| 8,715,200 B2 | 5/2014 | Pijls |
| 8,753,292 B2 | 6/2014 | Ingold et al. |
| 8,774,907 B2 | 7/2014 | Rothenberg |
| 8,801,693 B2 | 8/2014 | He et al. |
| 9,119,551 B2 | 9/2015 | Qi et al. |
| 9,125,578 B2 | 9/2015 | Grunwald |
| 9,180,260 B2 | 11/2015 | Huang et al. |
| 9,339,207 B2 | 5/2016 | Grunwald et al. |
| 9,415,188 B2 | 8/2016 | He et al. |
| 2003/0158491 A1 | 8/2003 | Krivitski et al. |
| 2003/0225336 A1 | 12/2003 | Callister et al. |
| 2007/0055141 A1 | 3/2007 | Kruger et al. |
| 2007/0137296 A1 | 6/2007 | Krivitski et al. |
| 2010/0228112 A1 | 9/2010 | Von Malmborg |
| 2011/0004198 A1 | 1/2011 | Hoch |
| 2011/0060199 A1 | 3/2011 | Robinson et al. |
| 2011/0245662 A1 | 10/2011 | Eggers et al. |
| 2013/0072943 A1 | 3/2013 | Parmar |
| 2013/0338530 A1 | 12/2013 | Kassab |
| 2014/0323887 A1 | 10/2014 | Anderson et al. |
| 2015/0031987 A1 | 1/2015 | Pameijer et al. |
| 2015/0080762 A1 | 3/2015 | Kassab et al. |
| 2015/0216445 A1 | 8/2015 | Carmeli et al. |
| 2015/0223707 A1 | 8/2015 | Ludoph |
| 2015/0297113 A1 | 10/2015 | Kassab et al. |
| 2017/0224420 A1 | 8/2017 | Stringer et al. |

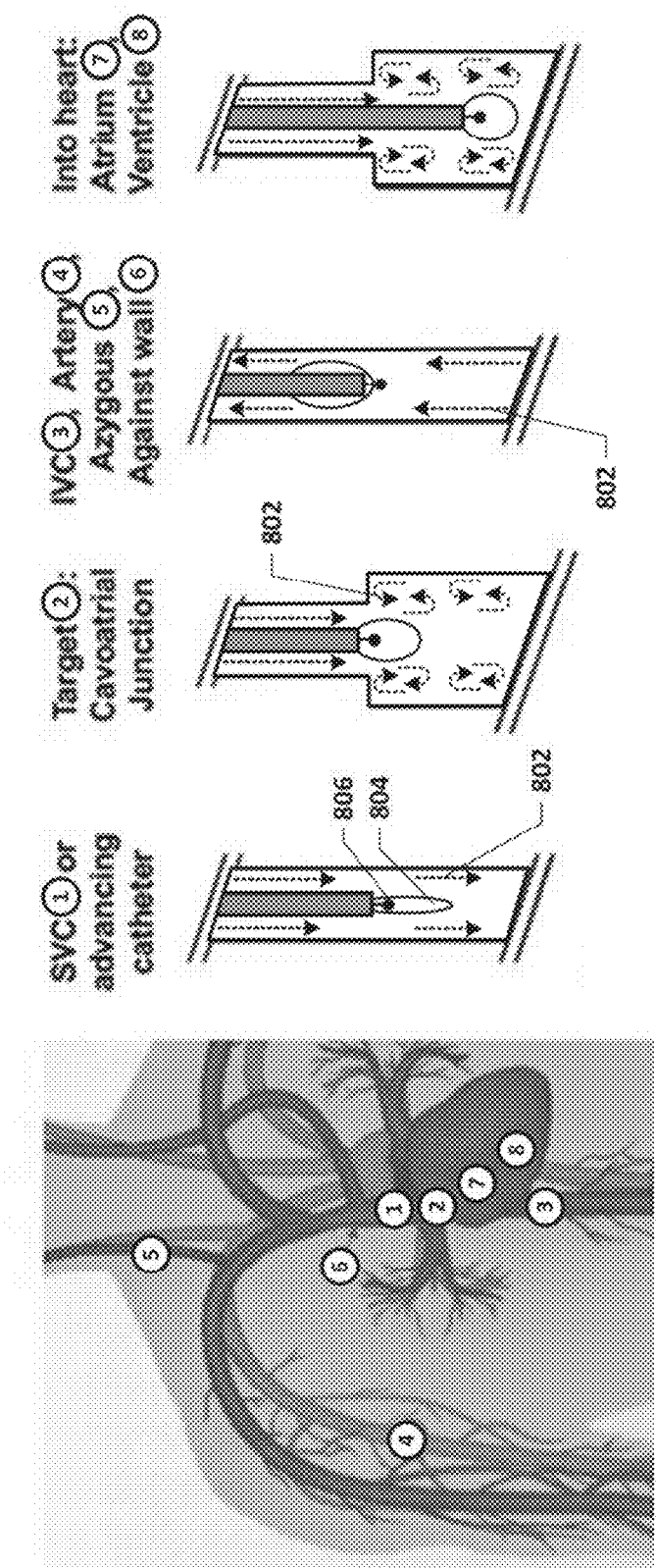

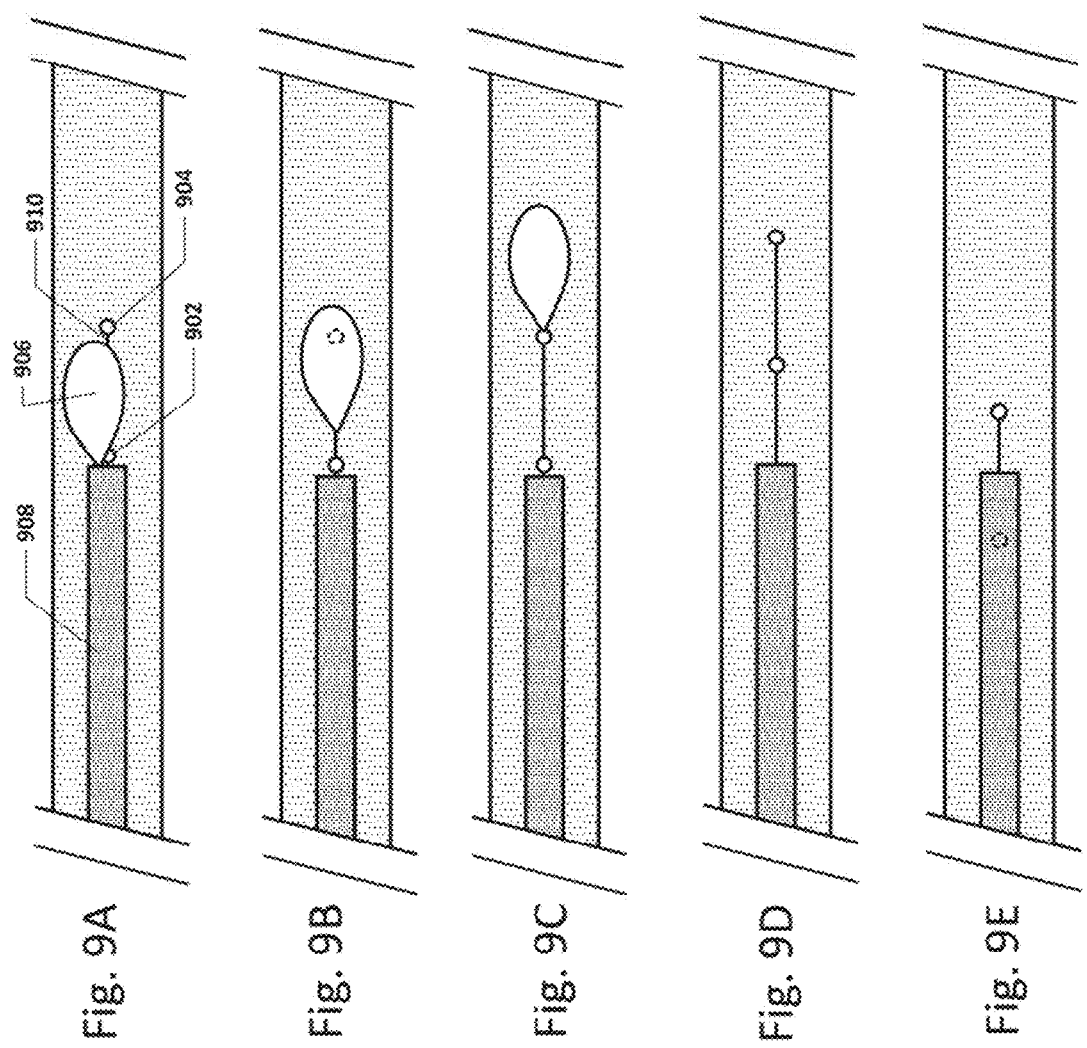

● Proximal temp sensor
○ Distal temp sensor
× Fluid injectate exit or port

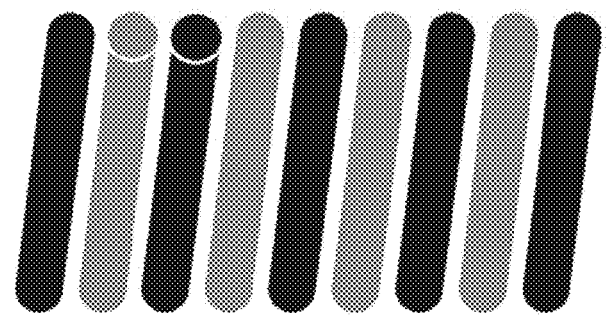
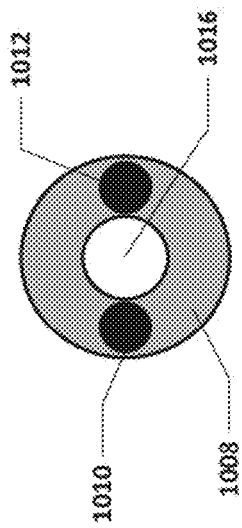
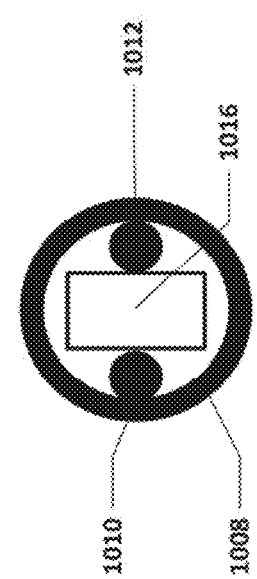
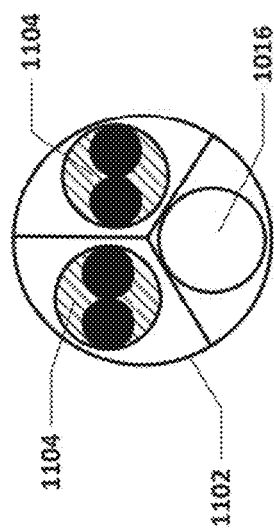

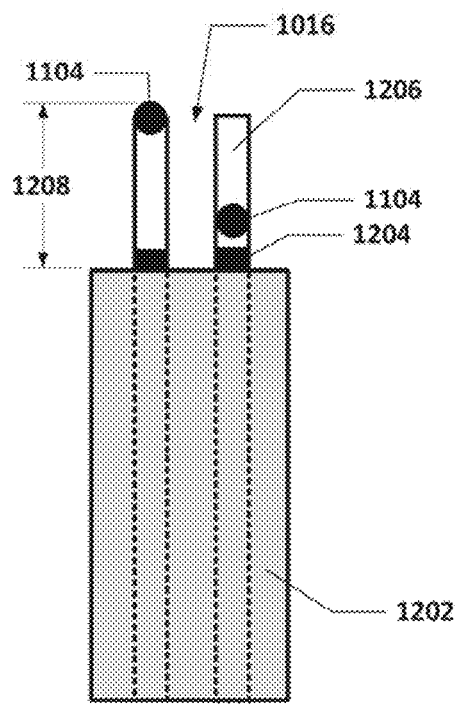
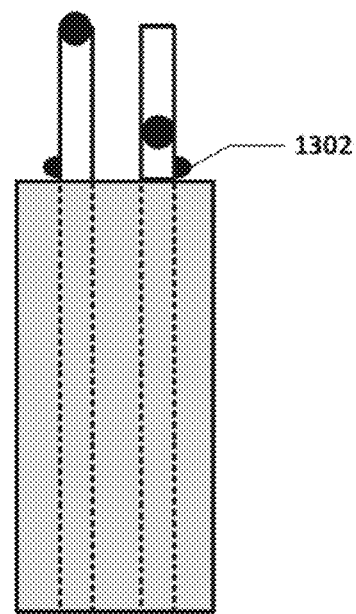
Fig. 12                    Fig. 13
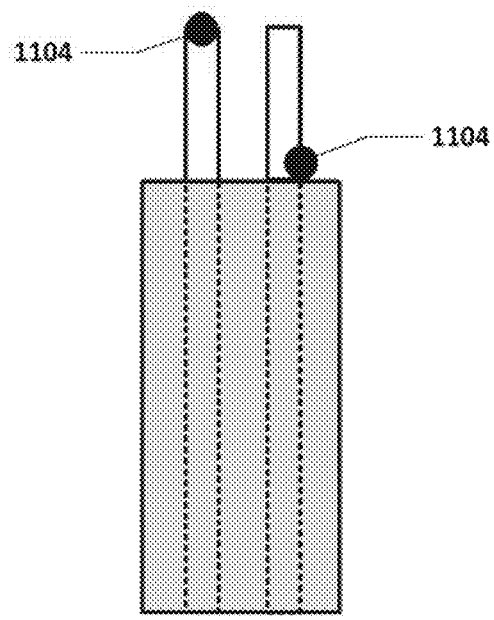
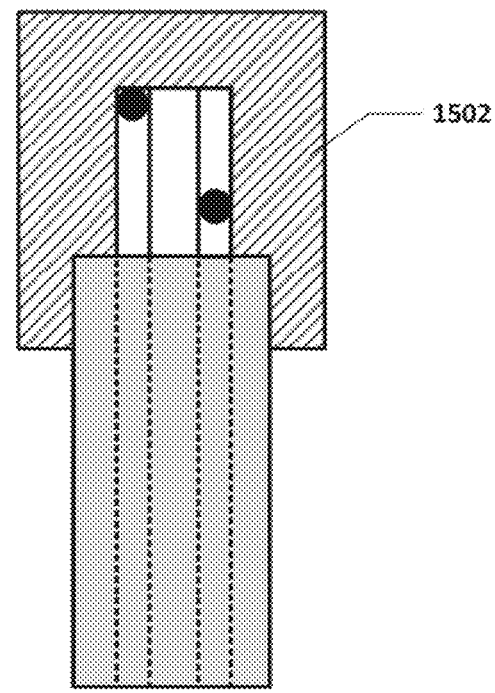
Fig. 14                    Fig. 15

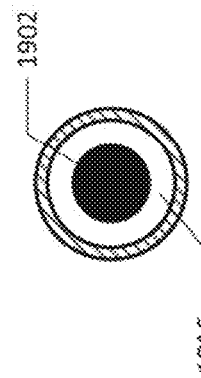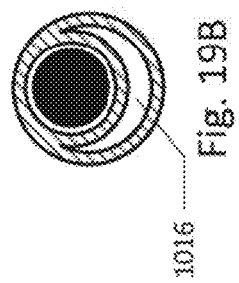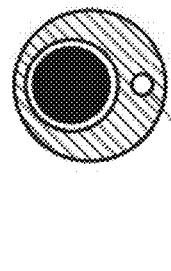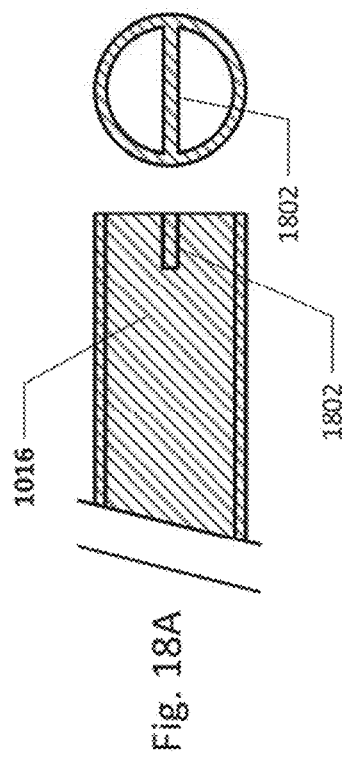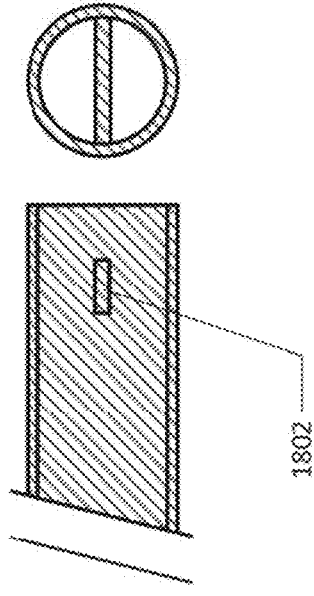

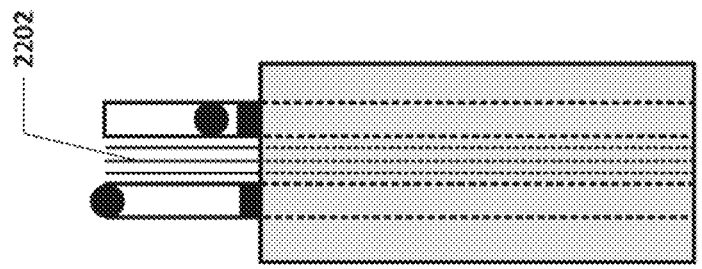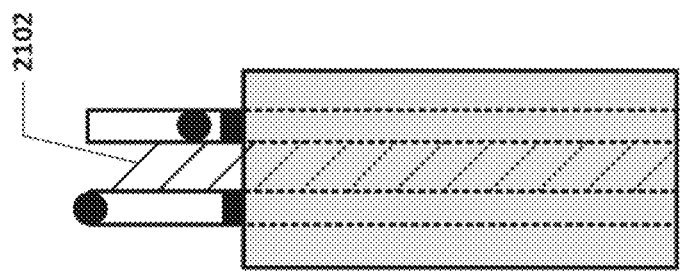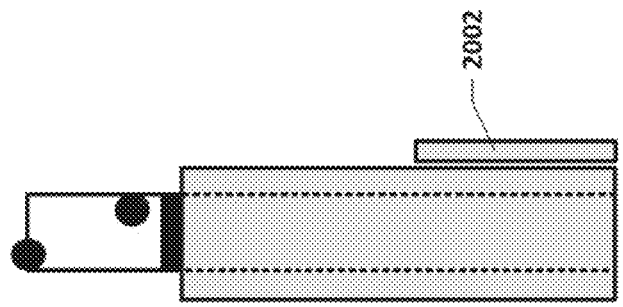

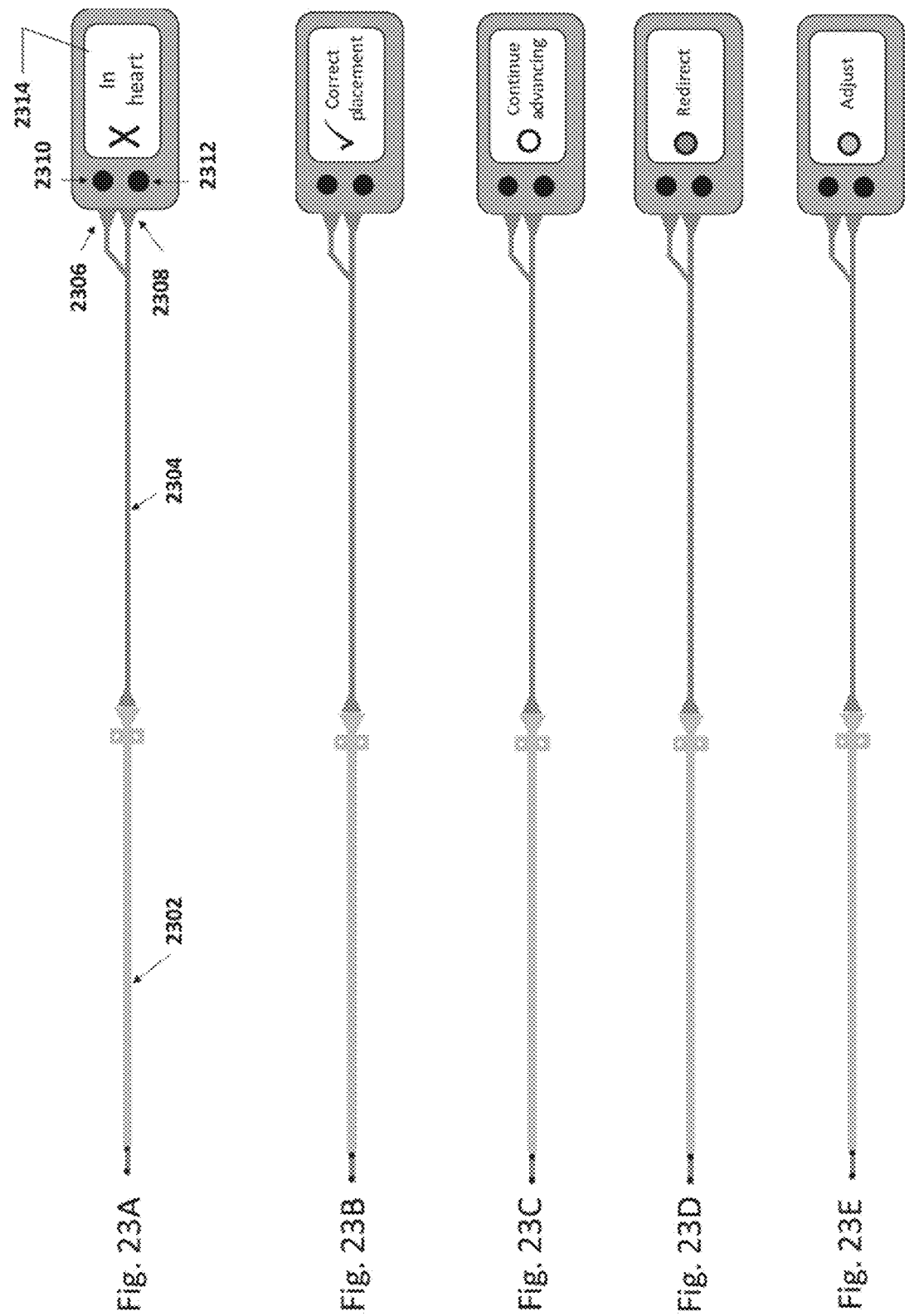

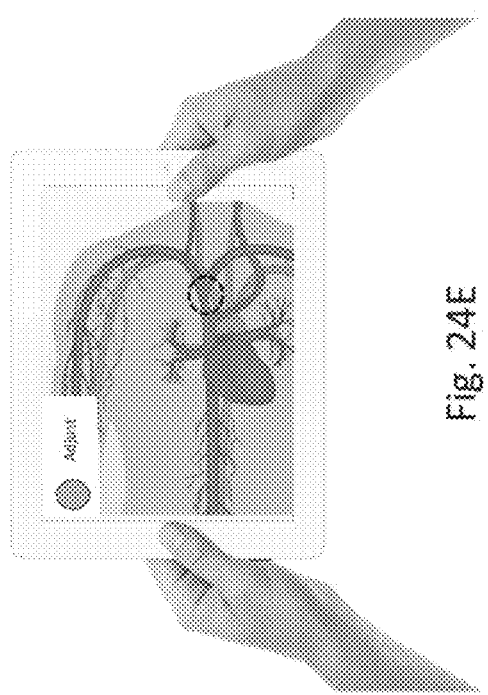

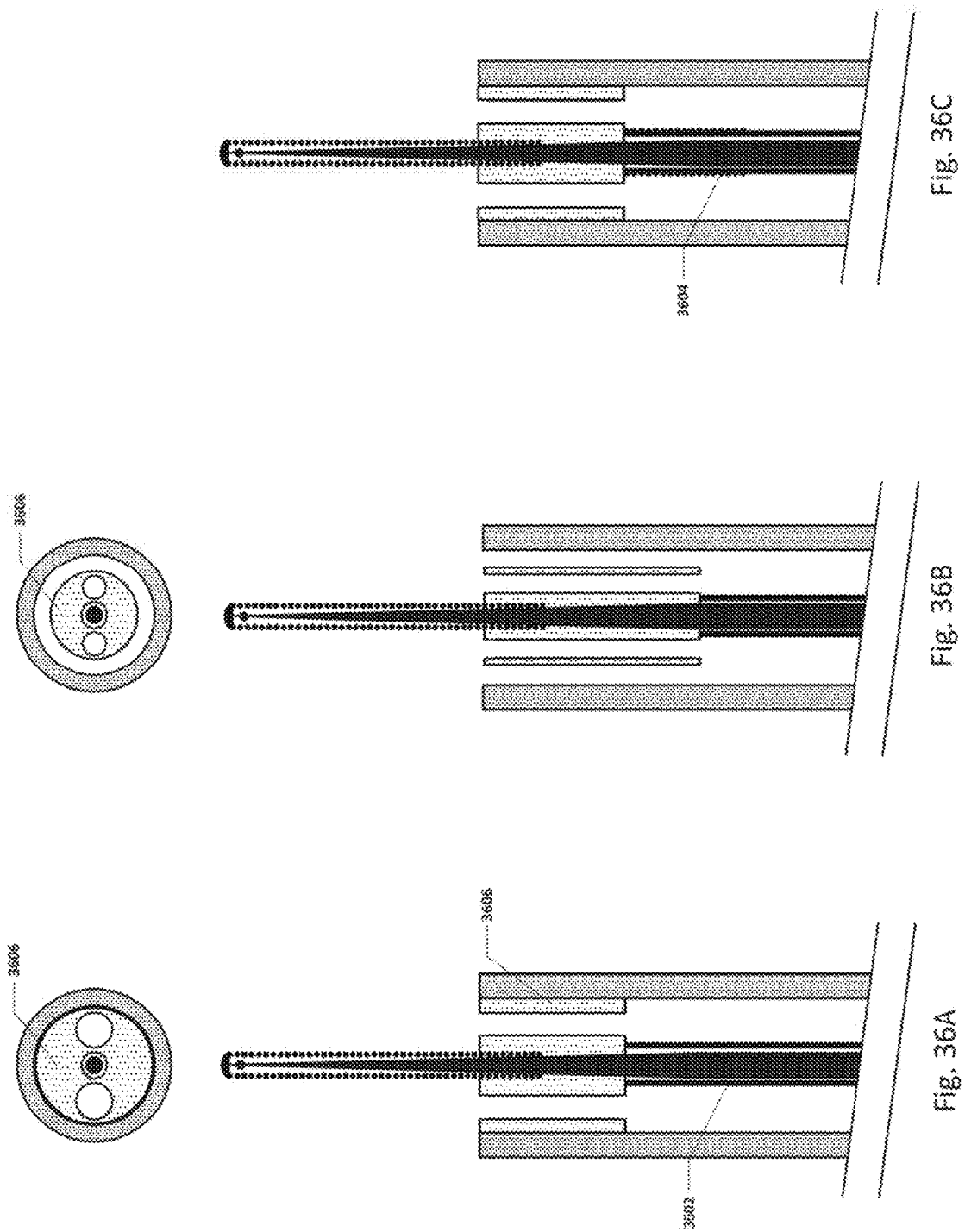

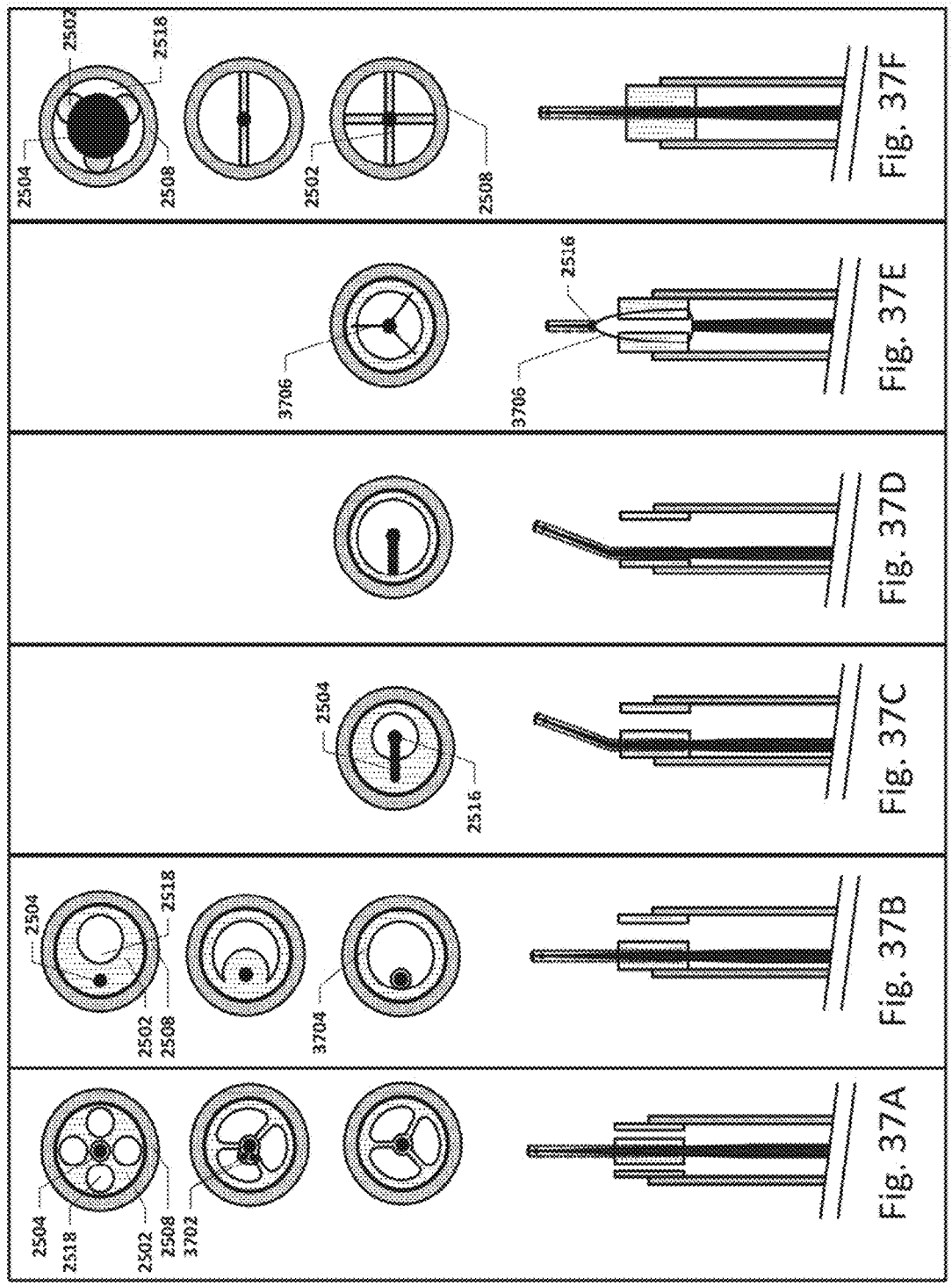

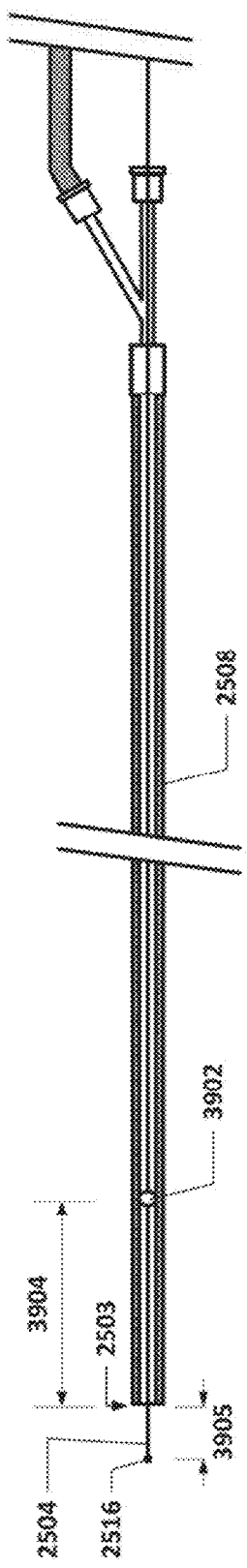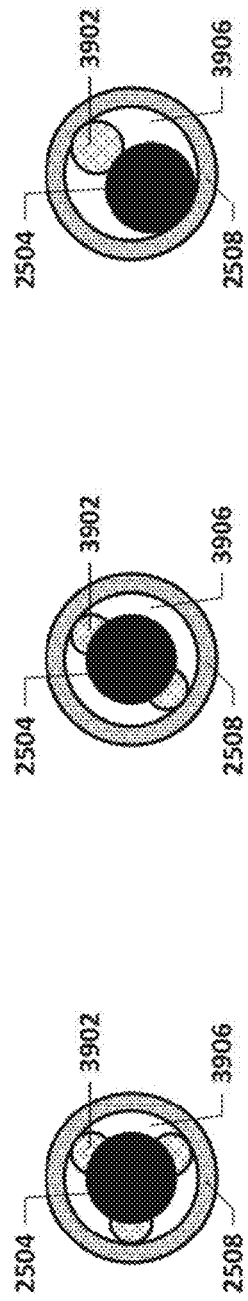

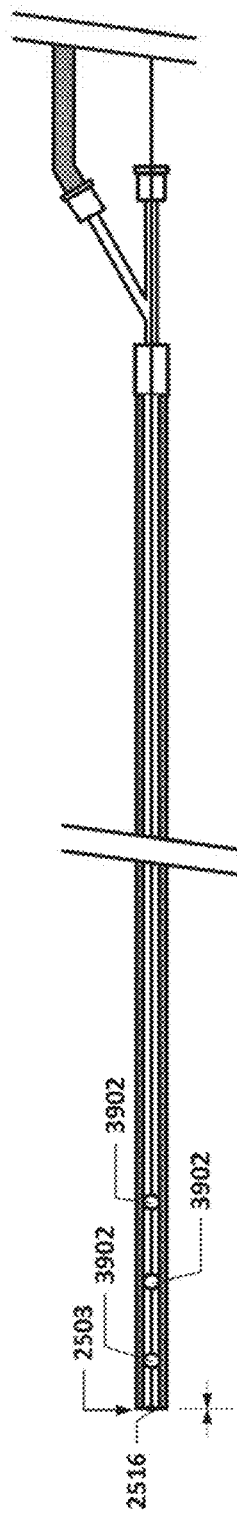
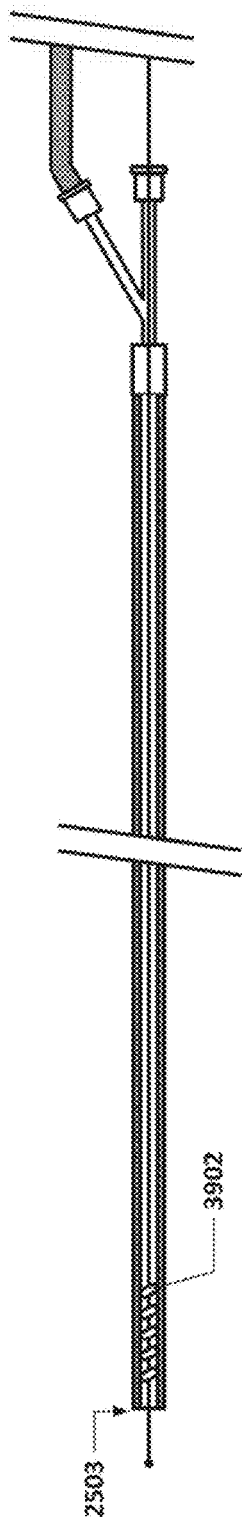
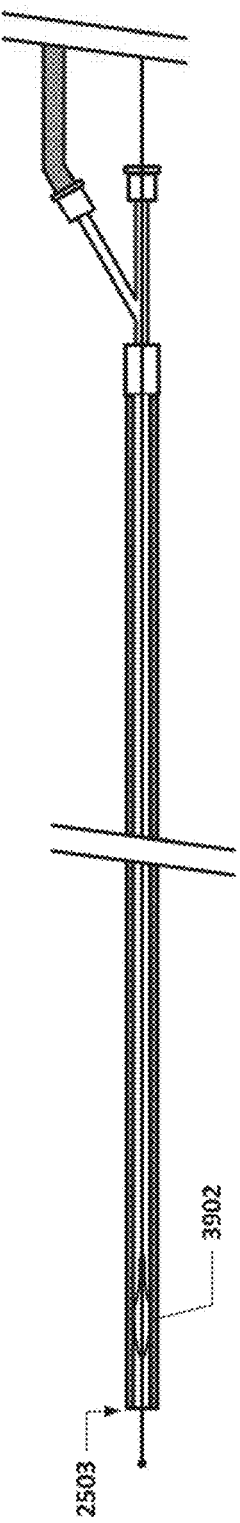
Fig. 39H
Fig. 39I
Fig. 39J

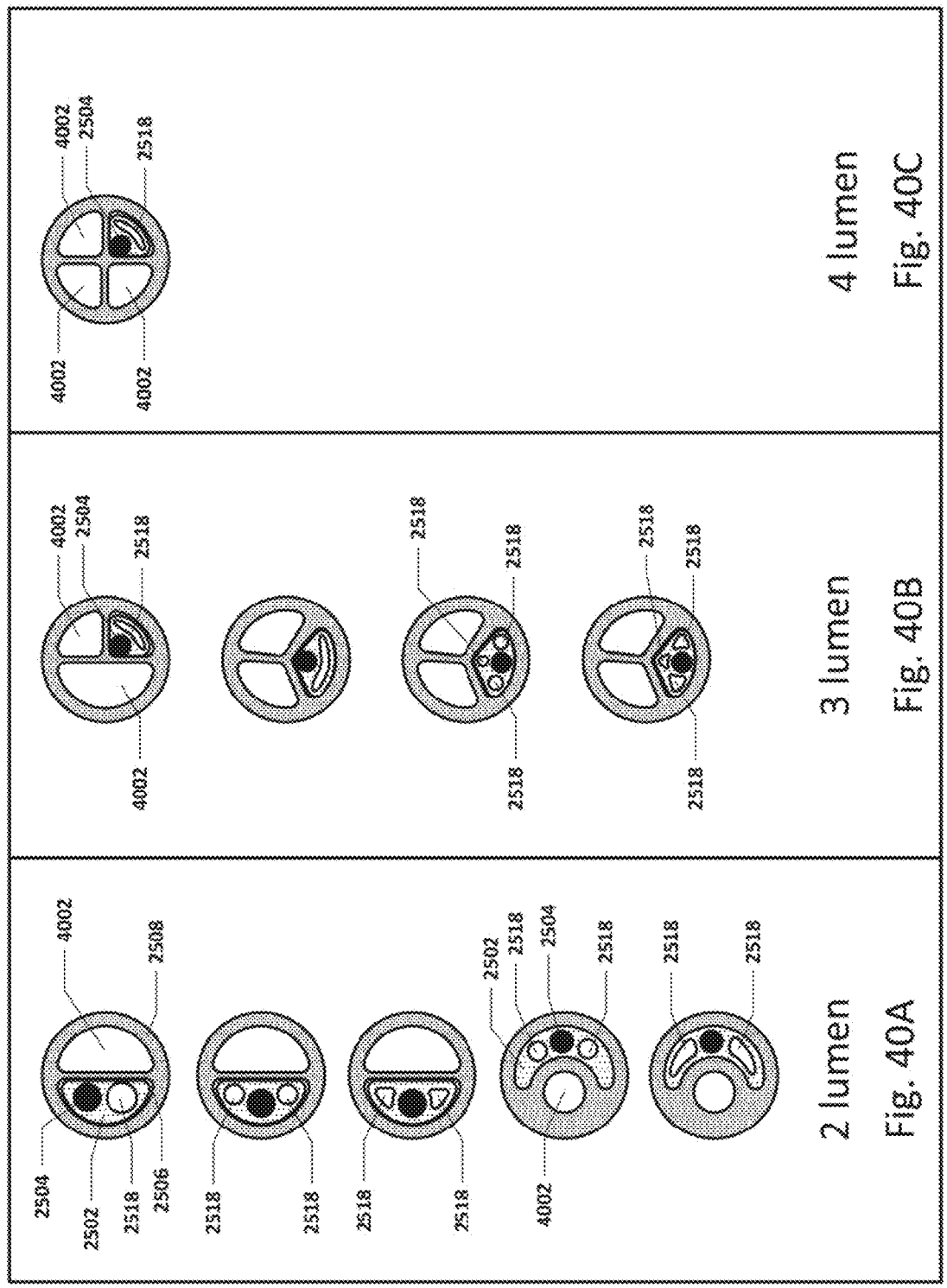

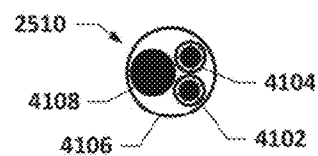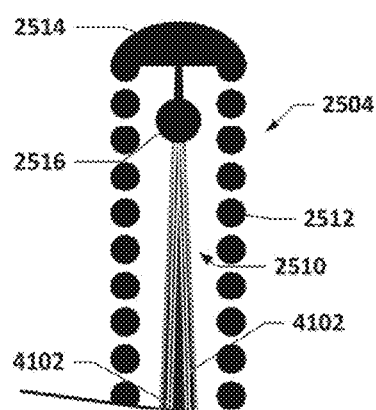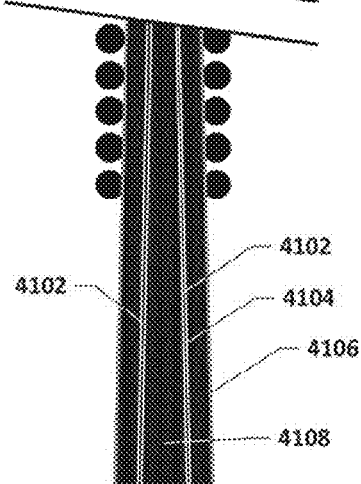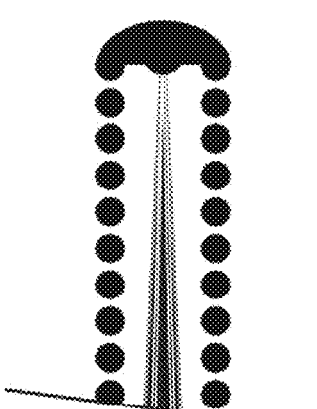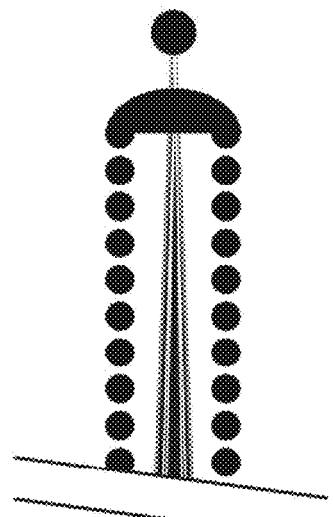
Fig. 41A          Fig. 41B          Fig. 41C

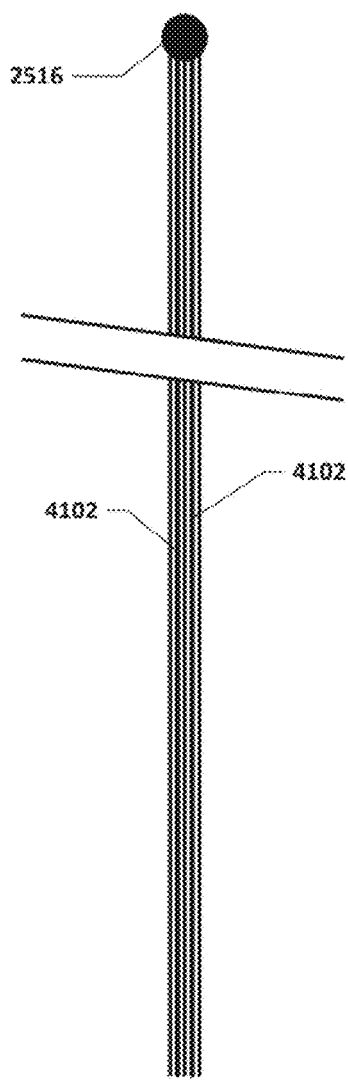
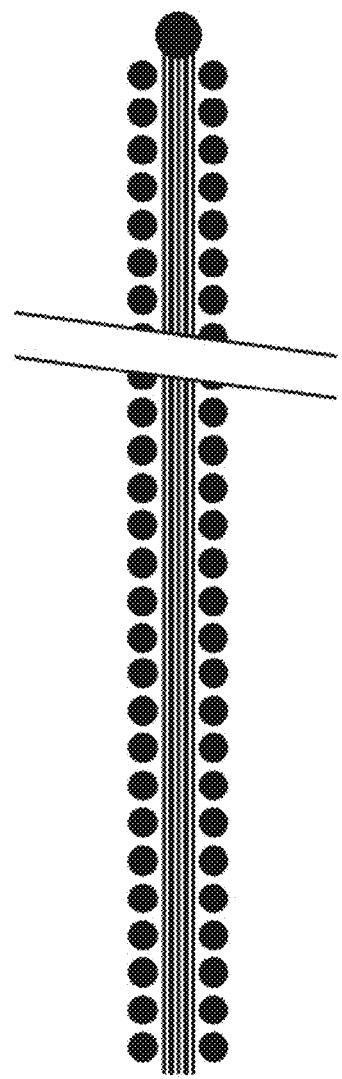
Fig. 42A   Fig. 42B   Fig. 42C

DEVICES AND METHODS FOR VASCULAR NAVIGATION, ASSESSMENT AND/OR DIAGNOSIS

CROSS-REFERENCE TO RELATED APPLICATIONS

This application is a continuation of PCT/US2017/038374 filed Jun. 20, 2017, which claims the benefit of priority to U.S. Provisional Application No. 62/356,383 filed Jun. 29, 2016, U.S. Provisional Application No. 62/405,879 filed Oct. 8, 2016 and U.S. Provisional Application No. 62/444,941 filed Jan. 11, 2017, each of which is incorporated herein by reference in its entirety.

FIELD OF THE INVENTION

The present invention relates to devices and methods for vascular navigation, assessment, and/or diagnosis.

INCORPORATION BY REFERENCE

All publications and patent applications mentioned in this specification are herein incorporated by reference to the same extent as if each such individual publication or patent application were specifically and individually indicated to be so incorporated by reference.

BACKGROUND OF THE INVENTION

A central vascular catheter (vascular catheter), also known as central line, central venous line or central venous access catheter, is a catheter placed into a large vein in the neck (internal jugular vein), chest (subclavian vein or axillary vein) or groin (femoral vein). It is primarily used to administer medication or fluids, obtain blood tests (such as central venous oxygen saturation), and measure central venous pressure.

A peripherally inserted central catheter (PICC or PIC line) is a form of vascular catheter that can be used for a prolonged period of time and/or for administration of substances. It is a catheter that enters the body through the skin (percutaneously) at a peripheral site, extends to the superior vena cava (a central venous trunk), and may remain in place for days or weeks.

Placing the catheter (PICC, central vascular catheter or related vascular catheter, referred to herein as "vascular catheter") in the ideal location can be challenging. The catheter may be mistakenly inserted into an artery instead of a vein, or into the incorrect vein or incorrect venous branch or advanced too far or into/along a vessel wall. Ideally, the catheter tip is placed in the superior vena cava/cavo-atrial junction (SVC-CAJ).

Correct placement currently is determined by taking a physical measurement of the distance from the catheter entry point to the estimated location of the lower one third of the superior vena cava. There are several challenges with current techniques. First, the catheter may enter into an artery instead of a vein. Second, a catheter may be advanced down the incorrect branch of the vein tree. The catheter may advance down an azygous vein, a thoracic vein, a jugular vein, or any number of additional veins on the branch. Third, a catheter may be advanced past the superior vena cava and into the heart or into the inferior vena cava. This can be a dangerous situation. Fourth, a catheter may advance up against, or embed in, a vessel wall which can prevent fluid delivery or fluid draw. Fifth, because the gold standard for catheter placement is essentially blind, placement verification needs to be confirmed with a chest x-ray which is substantially additional cost and time. Sixth, the estimated distance to the lower one third of the superior vena cava may be inaccurate.

There is a need for a relatively easy and accurate way of navigating a vascular catheter by accurately identifying the location of the tip of the catheter as it is advanced to its targeted location.

SUMMARY OF THE INVENTION

The present invention includes vascular catheter location and navigation devices and methods which determine the location of the tip of a vascular catheter using the introduction of a medium with a measurable parameter (e.g., temperature, light reflection, sound reflection, etc.) and sensing and measuring the measurable parameter as the catheter is advanced. Measurements of the parameter are tracked over time, recorded and analyzed. The value of the parameter and/or the shape of the parameter value vs. time curve may be used in the analysis. For example, curve amplitude, variability, standard deviation, slope, etc. may be used in the analysis of catheter location.

In one variation, the location detection system may generally comprise an elongate body; a conduit defining one or more flow passages, where each of the one or more flow passages has a distal end and where the conduit is configured to secure a position of the elongate body relative to the conduit; a sensor positioned at or in proximity to the distal end of the elongate body, wherein the conduit maintains a fixed distance between the sensor and the one or more flow passage distal ends, and wherein the sensor is configured to measure at least one parameter of a fluid after the fluid is emitted from the one or more flow passage distal ends; and a controller in communication with the sensor, wherein the controller is configured to determine a time-derived function of the at least one parameter of the fluid and is further configured to obtain a position of the sensor within a body of a subject.

In one variation for a method of determining a location within a body of a subject, the method may generally comprise positioning an elongate body within a lumen of a catheter; positioning the catheter within the body of the subject; introducing a fluid through the lumen and one or more flow passages of a conduit into the body; measuring via a sensor at least one parameter of the fluid after introduction within the body of the subject, wherein the sensor is positioned at or in proximity to a distal end of the elongate body such that the sensor is maintained at a fixed distance relative to a fluid exit port of the catheter or conduit; determining a time-derived function of the at least one parameter of the fluid; and determining a position of the sensor within the body of the subject based upon the time-derived function.

In yet another variation, the location detection system for use within a catheter lumen may generally comprise an elongate body; a sensor positioned at or in proximity to the distal end of the elongate body, wherein the sensor is configured to measure at least one parameter of a fluid after the fluid is emitted from the catheter lumen; and a controller in communication with the sensor, wherein the controller is configured to determine a time-derived function of the at least one parameter of the fluid and is further configured to obtain a position of the sensor within a body of a subject.

Flow direction, characteristics, profiles, and types, with respect to the catheter and catheter tip can provide a vast array of information on catheter positioning during placement, after initial or subsequent placement, after the catheter has been in place for a period of time, and/or during withdrawal.

Devices and methods disclosed herein can be used to inform the user of one or more of the following conditions: insertion, placement or advancement of the catheter into an artery rather than a vein; insertion, placement or advancement of the catheter into an undesired vein branch; placement or advancement of the catheter too near, into, or past the heart; or placement of the catheter tip up against, or embedded in, a wall of a vessel. Each of these scenarios is described in detail herein.

Blood Flow characteristics and direction can help determine if the catheter is in an artery or a vein. In the case of a vein, the blood will generally be flowing more slowly toward the heart, while with the artery the blood will generally be flowing more quickly away from the heart. At least the blood flow direction and speed with respect to the catheter will be different depending on whether the catheter is in an artery or vein. Other flow parameters may also be different (turbulence, pulsatility, etc.). In addition, the flow characteristics of blood within a smaller branch of the blood vessel will be different than the flow characteristics in a larger vessel. For example, blood flow within a vein branch may completely or substantially stop where a catheter tip is totally or partially occluding the vein branch. In the case where the catheter tip is seated against a vessel wall, flow patterns around the catheter are different than when the catheter tip is in free flowing blood.

In the situation where the catheter tip passes into the superior vena cava, and passes near or into the heart's right atrium or right ventricle, the flow characteristics of the blood will change. For example, the blood flow may become more or less turbulent. More or less turbulence results in different flow characteristics, profiles, and flow types and can be detected by a variety of types of sensors.

These flow profile changes can be measured using devices and methods disclosed herein.

Devices disclosed herein may include a catheter, a guidewire, a stylet, a controller, communications, an infusion mechanism, a medium source, medium sensor or sensors etc.

Devices and methods disclosed herein utilize the introduction of a medium (saline, fluid, light, sound, etc.) which has a measurable parameter (temperature, opacity, light reflectivity, sound reflectivity, density, viscosity, ability to absorb light, ability to absorb sound, amplitude, etc.) where the measurable parameter can be detected using a sensor (temperature sensor, thermocouple, light sensor, sound sensor, microphone, etc.). By introducing a medium at or near the tip of the catheter, and measuring one or more parameters of the medium over time, and possibly over distance, flow parameters, such as flow direction, rate, volume and type, turbulent or laminar, can be determined. Based on these determinations, the user can identify whether the catheter tip is progressing to the desired position in the vasculature via the desired path. Vessels may be identified by type (vein vs. artery, vs heart etc.), size, shape, etc.

The medium may be injected or introduced in boluses or drips, periodically during all or part of catheter placement, continually during all or part of catheter placement, or at regular intervals during all or part of catheter placement. The medium may be introduced manually, or automatically via a controller, or automatically via an intravenous (IV) bag with or without an IV pump, or passively with an IV.

Measurements of one or more medium parameters may be taken before, during and/or after medium introduction. For example, room temperature or other non-body temperature saline (or other fluid) may be injected through the catheter or stylet during placement. One or more sensors at or near the distal tip of the catheter/stylet can measure the temperature of the fluid immediately surrounding the sensor(s) over time. Based on blood flow characteristics, including direction, pulsatility and turbulence, the temperature profile over time will be different at different locations, resulting in a temperature (or parameter) profile or signature for different flow types and therefore different catheter/stylet tip location scenarios.

Temperature sensors may include thermocouples or other temperature sensors, such as, fiber optic, resistive, bimetallic, thermometer, state-change, silicon diode, thermistors, optical temperature measurement (infrared or otherwise), mercury thermometers, manometers, etc. The sensor or sensors is/are in communication with a controller which records and/or analyzes the signal from the sensor(s). The communication between the sensor and the controller may be wired or wireless.

By placing a thermocouple, thermistor, or other temperature sensing device, or an array of temperature sensing devices on or through the catheter, one can determine the direction of flow of a room temperature fluid bolus that is injected into the blood stream. Since blood temperature is around 37 degrees C., a saline (or other) fluid bolus or fluid infusion with a temperature around 20-25 degrees C. or between 15 and 30 degrees C. or between 0 and 35 degrees C., or generally cooler than 37 degrees C. is distinguishable from body temperature and can be used to detect blood flow direction and characteristics, and therefore, device location.

In some embodiments, optical sensing can be used. Optical sensors can be used to detect the direction of flow by measuring the amount of dilution of blood with another fluid with different optical characteristics, such as saline.

Sonar or sound can alternatively be used as the parameter to detect blood flow direction, velocity and other blood flow characteristics. Sound waves may be produced by the controller and conveyed to the tip, or near the tip, of the catheter. A sound detector, or microphone, records the sound waves reflected back by the red blood cells or other components of blood. Saline may also be introduced to create a change in the sound waves detected.

Various mediums and/or parameters may be used in combination in some embodiments. For example, light (visible and/or not visible) and temperature may both be used. In addition, other sensors may be used to aid in locating the catheter, including electro cardiogram (ECG). Pressure, as disclosed in U.S. provisional patent application 62/492,739 filed on May 1, 2017, and incorporated herein in its entirety by reference, may also be used in combination with these embodiments.

Embodiments that incorporate more than one type of sensor may be used either in each situation (vein vs. artery, vessel branch, vessel wall, catheter in heart or past heart), or different sensors may be used in different situations. For example, pressure may be used to determine when the catheter tip is in the heart, where temperature may be used to determine whether the catheter is in an artery. Or, for example, ECG can be used to determine if the catheter is in the cavo-atrial junction but temperature can be used to determine if the catheter has gone down an azygous or unintended vein branch.

In some embodiments, a camera may be used to optically determine the presence, and possibly the density, or number, of red blood cells. If a greater number of cells pass by, then the flow is stronger. If they are flowing in the opposite direction, then the flow has reversed direction, thus the catheter is proceeding in the incorrect direction.

These sensing modalities can also be combined with one or more (ECG) sensors to detect catheter placement. ECG electrodes can be placed precisely either at the target location of the catheter tip (for example, in the superior ⅓ of the vena cava), or over the heart itself to detect an unnecessary over extension of the catheter. Alternatively, one or more ECG sensors may be incorporated into the device itself, for example, into a guidewire/stylet.

In any of the embodiments disclosed herein, the sensors may be located at or near the tip of, or along the length of a guidewire or stylet that passes through a vascular catheter.

BRIEF DESCRIPTION OF THE DRAWINGS

FIG. 8 is a schematic illustration showing fluid flow in different areas of the vascular system.

FIGS. 9A-9E show various embodiments of the vascular catheter navigation device.

FIGS. 11A-I show various views of various embodiments of a stylet/guidewire version of the vascular catheter navigation device.

FIGS. 12-17 show various embodiments of the vascular catheter navigation device.

FIGS. 18A and B show 2 possible embodiments for a flow director.

FIGS. 19A-C show other embodiments of the vascular catheter navigation device injectate lumens.

FIG. 20 shows an embodiment of the vascular catheter navigation device.

FIG. 21 shows features that enhances a controlled turbulent flow.

FIG. 22 shows features that create a controlled laminar (or less turbulent) flow.

FIGS. 23A-E and 24A-E show possible graphical user interfaces of the device.

FIGS. 36A-C show an embodiment of the vascular catheter navigation device which includes a compressible conduit.

FIGS. 37A-F show 2 different cross-sectional views of various embodiments of the vascular catheter navigation device.

FIGS. 39A-D are longitudinal cross sectional views of embodiments of the vascular catheter navigation device.

FIGS. 39E-G are radial cross sectional views of embodiments of the vascular catheter navigation device.

FIGS. 39H-J are cross sectional views of embodiments of the vascular catheter navigation device with securing type conduits.

FIGS. 40A-C show different configurations of vascular catheter lumens and variations of embodiments of the vascular catheter navigation device which work with them.

FIGS. 41A-F show various embodiments of a guidewire/stylet component of the vascular catheter navigation device.

FIGS. 42A-C show an embodiment of the vascular catheter navigation device.

DETAILED DESCRIPTION OF THE INVENTION

Figure 1:
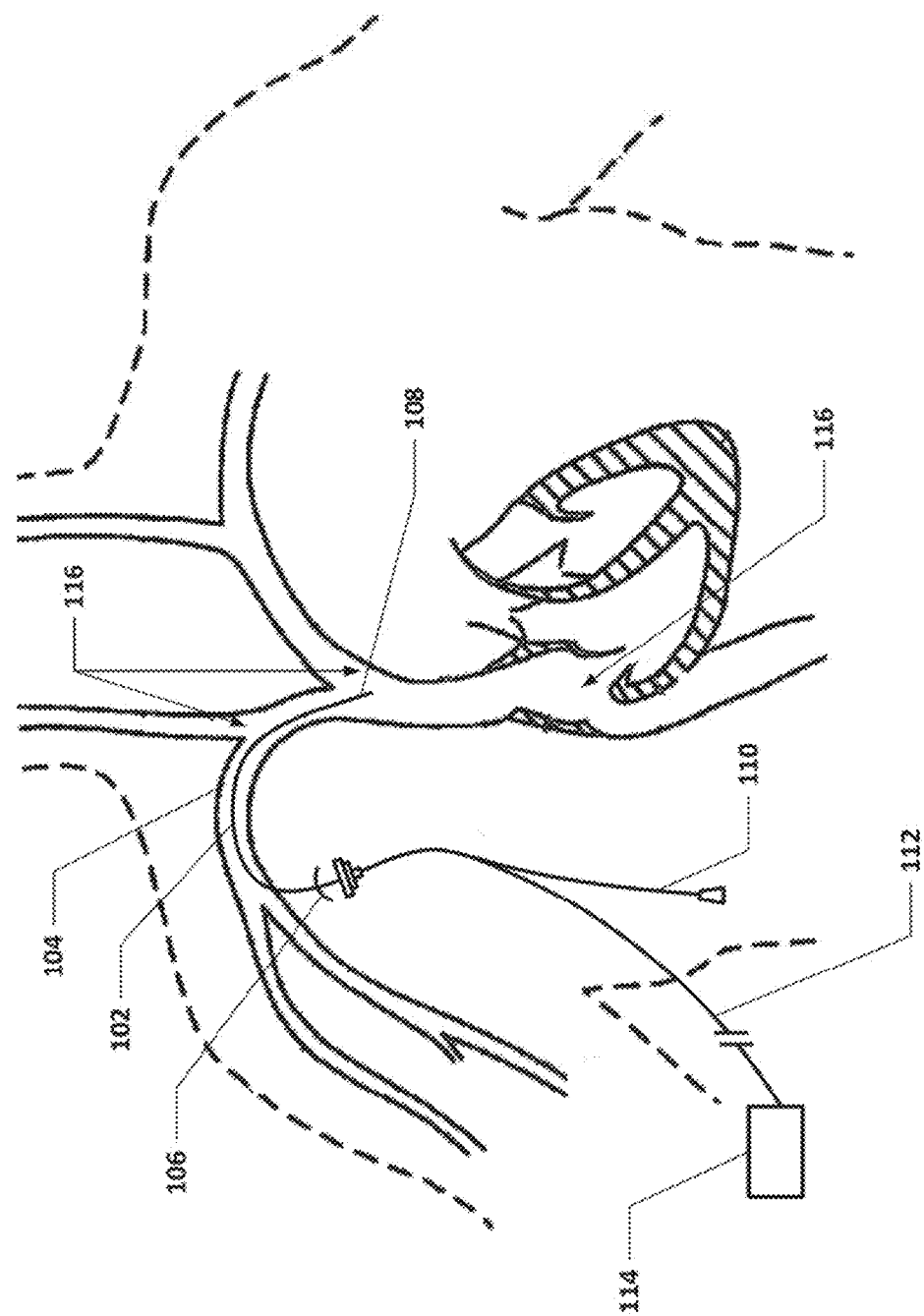
FIG. 1 shows an embodiment of the vascular catheter navigation device navigating the human anatomy.

FIG. 1 shows an embodiment of the vascular catheter navigation device or system navigating the human anatomy. Vascular catheter navigation device 102 is shown in vein 104 of a patient. The vascular catheter navigation device has been inserted into the patient via insertion point 106. The insertion point is shown here in the patient's chest, however the insertion point may alternatively be the patients leg, arm or neck or other location. To navigate a standard vascular catheter into its desired location, several undesirable obstacles need to be avoided and/or overcome. For example, a vascular catheter may be mistakenly placed into an artery instead of a vein, a vascular catheter may venture down or up an incorrect branch of the vascular system, a vascular catheter may become lodged against a wall of a blood vessel, a vascular catheter may be advanced too far, either too close to the heart, into the heart or past the heart, or a vascular catheter may not be advanced far enough to reach its desired location, or may migrate to a less desirable location. A few of these hazard areas are labeled 116. Distal tip of vascular catheter navigation device is shown as 108. At the proximal end of vascular catheter navigation device is shown infusion or sampling lumen 110 which is in fluid communication with opening or openings at or near the distal end of vascular catheter navigation device, and sensing port 112 which is in communication with controller 114. Sensing port 112 is in communication with one or more sensors (not shown here) at or near distal tip 108 of vascular catheter navigation device 102. Although one infusion/sampling lumen and one sensing port are shown here, multiple infusion/sampling and/or sensing ports may exist. Infusion lumen 110 may also be in communication with controller 114.

Figure 2:
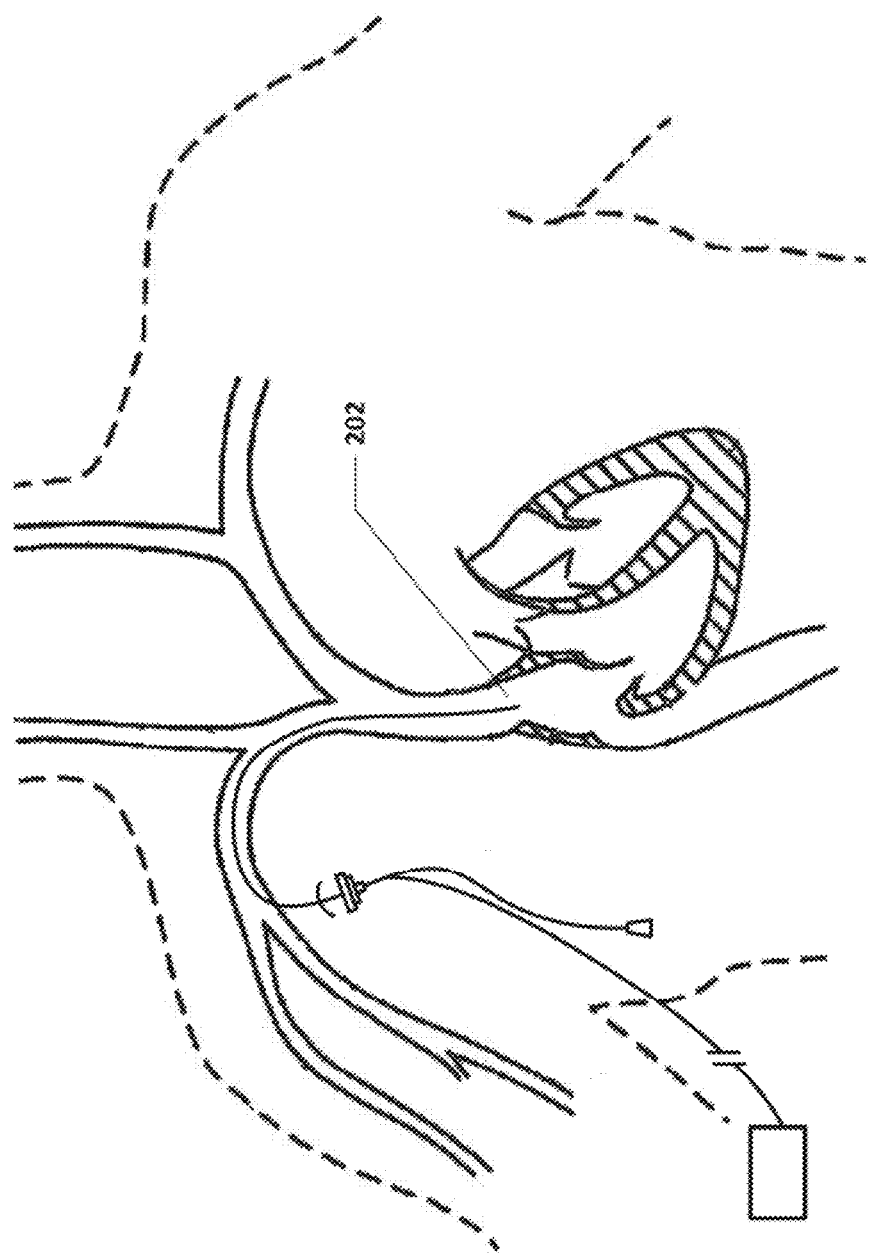
FIG. 2 shows an embodiment of the vascular catheter navigation device placed in the human anatomy.

FIG. 2 shows an embodiment of the vascular catheter navigation device where the distal tip is placed in the superior vena cava/cavo-atrial junction (SVC-CAJ) 202.

Figure 3:
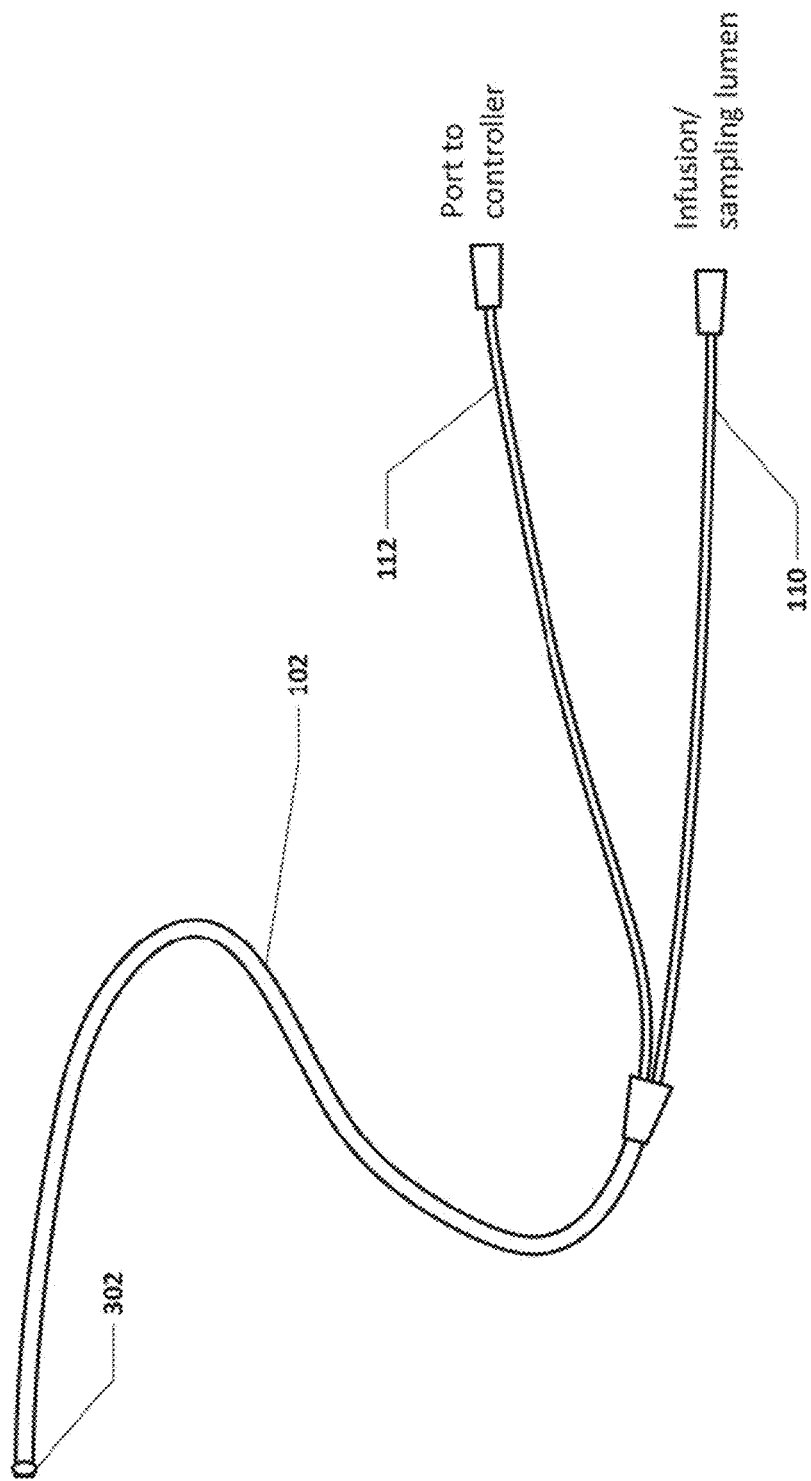
FIG. 3 shows an embodiment of the vascular catheter navigation device.

FIG. 3 shows an embodiment of the vascular catheter navigation device. The distal end of the vascular catheter navigation device is inserted into the appropriate access vein, and advanced along the vein to its target location. After the vascular catheter navigation device is inserted into the blood vessel, generally through a needle, or sheath, sensing element 302 senses a parameter within the blood vessel. A medium, such as fluid, with a measurable parameter, such as temperature, is injected through the device, and into the blood vessel. The sensor signals are communicated back to the controller where the sensor signal(s) are analyzed based on the sensor data over time, including data curve slope, magnitude, value, length, variability, standard deviation, shape, etc. For example, the controller can determine whether the distal end of the vascular catheter navigation device is in an artery instead of a vein, based on magnitude and direction of blood flow around the vascular catheter navigation device by measuring and analyzing the measurable parameter. If the controller determines that the distal end of the vascular catheter navigation device is in an undesired position, an alert or other indicator may communicate with the user. For example, if the controller determines that the catheter is in an artery instead of a vein, a specific identifying signal may sound, including an audible, visual signal etc., instructing the user to remove the vascular catheter navigation device, and any other device, such as sheaths, catheters etc., and apply pressure to the blood vessel.

Similarly, the vascular catheter navigation device can sense when the distal end is in the incorrect branch of a vein, based on flow direction, and possibly flow profile and magnitude. When advancing the vascular catheter navigation device in the correct direction and in the correct vessel (toward the SVC-CAJ, in a vein), the blood flows over the vascular catheter navigation device from the more proximal end to the distal end.

FIG. 3 shows one sensor 302, one sensor port 112 and one infusion/sampling lumen 110. However, more than one infusion/sampling lumen and/or more than one sensors may be present. In addition the port to the controller and the sampling lumen could be the same lumen and be incorporated into a single lumen catheter. The infusion and/or sampling lumen may also be connected to the controller.

Figure 4:
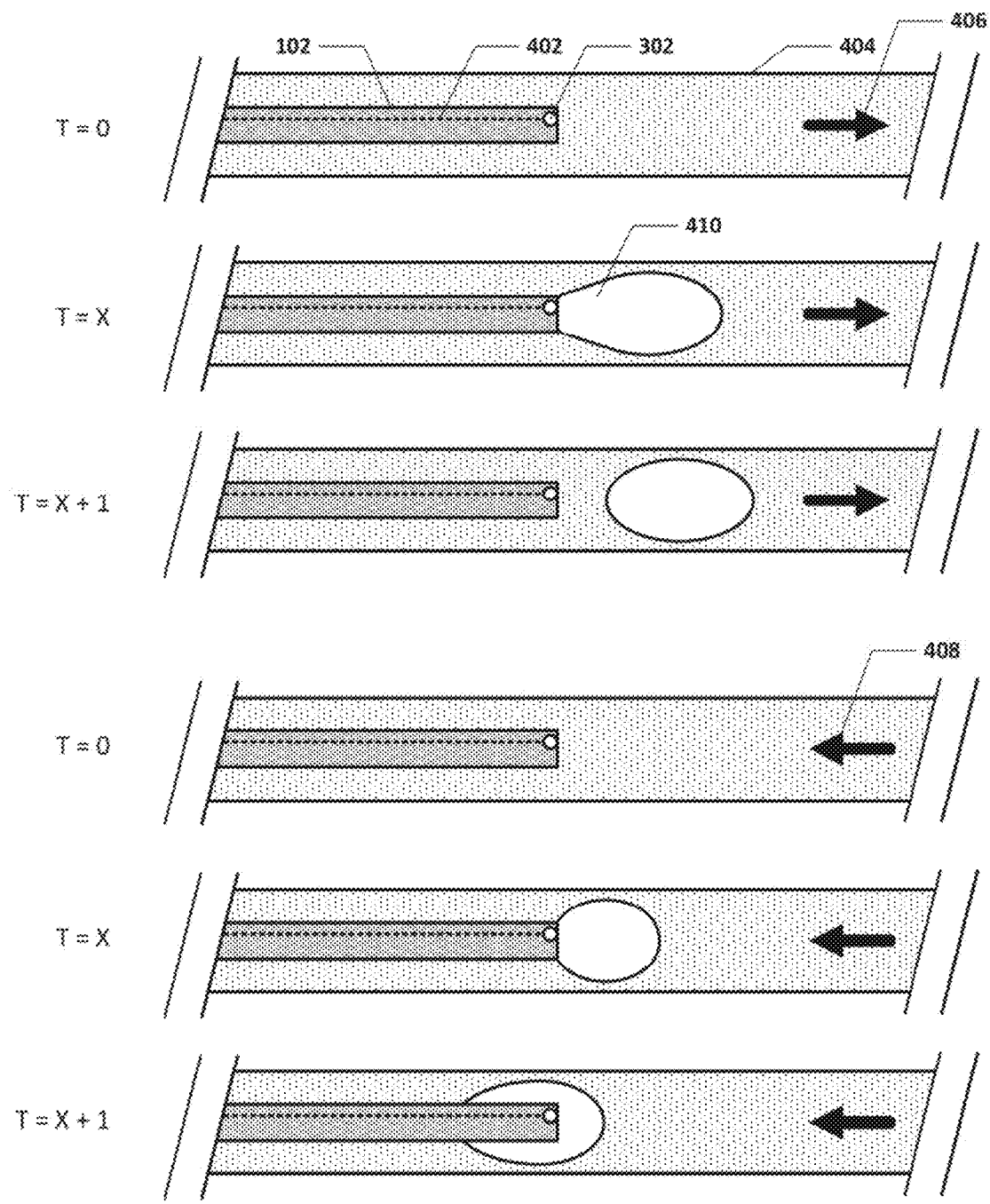
FIG. 4 shows the influence of fluid flow direction on flow behavior of an injected fluid bolus with respect to the catheter tip before, during and after injection.

FIG. 4 shows the influence of fluid flow direction on flow behavior with respect to the catheter tip before, during and after an injected fluid bolus. At time=0, device 102 is in vessel 404. Device 102 includes sensor 302. Sensor 302 is designed to measure a parameter of blood and/or the injection medium. The controller (not shown) is in communication with sensor 302 via connector 402 which, in this example, runs the length of the catheter back to the controller. Sensor 302 and connector 402 may be incorporated into the vascular catheter or may be incorporated into a stylet that runs through the catheter. Medium 410 is introduced into the vessel at time=x. For example, the medium may be saline at a temperature which is different than that of the body. The parameter measured by the sensor in this example would be temperature. After the injection, at T=x+1, blood flow will carry the medium with the blood flow. Where blood flow 406 flows away from the catheter, the bolus of medium 404 travels away from the catheter tip and away from the sensor. Where blood flow 408 flows toward the catheter, the bolus of medium 410 travels toward and over the catheter tip. This example shows a bolus of fluid, but a stream of fluid may also be used.

Depending on the location of the sensor(s), different temperature profiles over time may be measured. Variables in flow rate, direction, turbulence, etc. will affect the mixing of blood and medium and affect the profile of the parameter, in this example, temperature, over time. In this way, the system can determine direction of blood flow at or near the catheter tip.

Figure 5A:
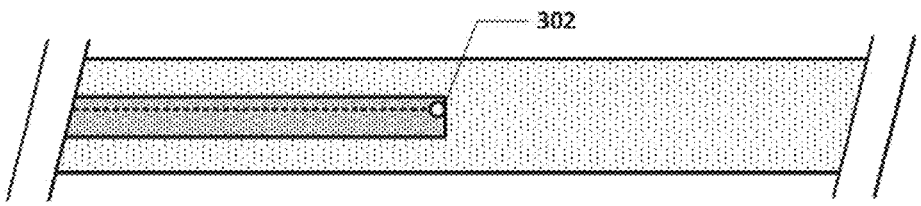
FIGS. 5A-5E show a variety of embodiments of the vascular catheter navigation device.
Figure 5B:
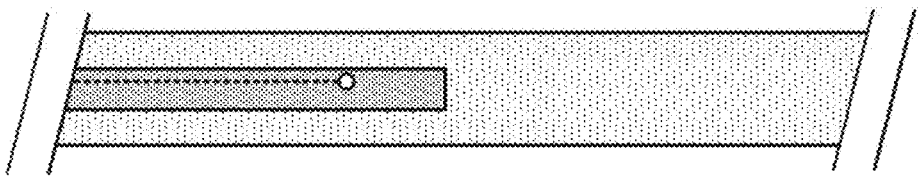
Figure 5C:
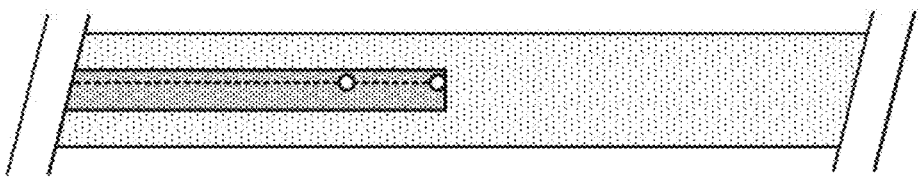
Figure 5D:
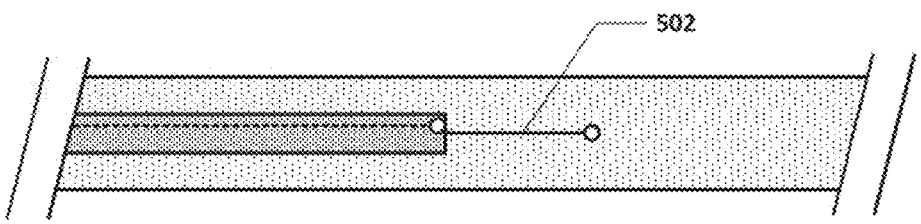
Figure 5E:
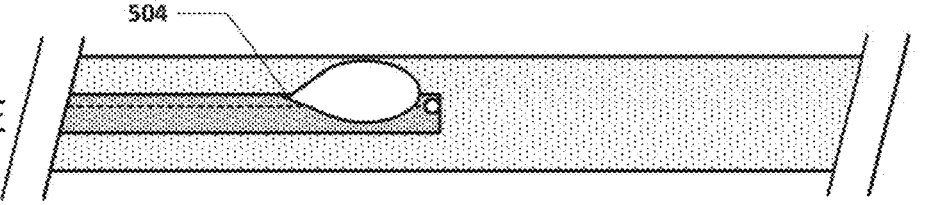

FIGS. 5A-5E and 6A-6E show several example embodiments of the vascular catheter navigation device. FIG. 5A shows an embodiment with sensor 302 at the catheter tip. FIG. 5B shows an embodiment with the sensor near, but not at, the catheter tip. This configuration may prevent the sensor from measuring the parameter during introduction of the medium from the catheter tip, allowing better distinction between flow directions. FIG. 5C shows an embodiment with 2 sensors, one at the catheter tip, and one near, but not at, the catheter tip. Sensor readings at different positions will vary based on fluid flow direction, characteristics, profile etc. A sensor near, but not at, the catheter tip may be from about 0.05 cm to about 2.0 cm back from the tip. Alternatively, a sensor near, but not at, the catheter tip may be from about 0.75 cm to about 1.25 cm back from the tip. FIG. 5D shows an embodiment where a sensor is on guidewire or stylet 502. Stylet 502 may move freely within the catheter allowing one or more sensors to be placed at a distance from the catheter tip. In addition, the guidewire/stylet may be removed after catheter placement. In this embodiment, the catheter may also include a sensor, as shown here. FIG. 5E shows an embodiment with opening 504 which is near, but not at, the catheter tip. This opening may be in fluid communication with a separate medium introduction lumen or infusion lumen. This specific medium introduction lumen may exit at the catheter tip. An opening near, but not at, the catheter tip may be from about 0.5 cm to about 2.0 cm back from the tip. Alternatively, an opening near, but not at, the catheter tip may be from about 0.75 cm to about 1.25 cm back from the tip. The medium introduction lumen may be in the catheter or may be within the stylet.

Figure 6A:
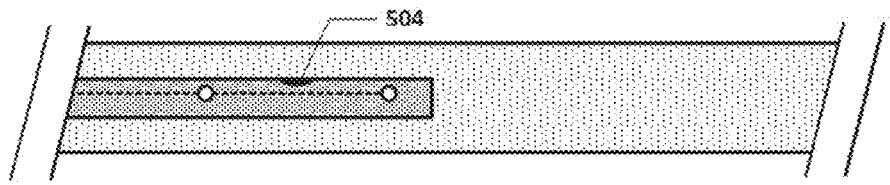
FIGS. 6A-6E show a variety of embodiments of the vascular catheter navigation device.
Figure 6B:
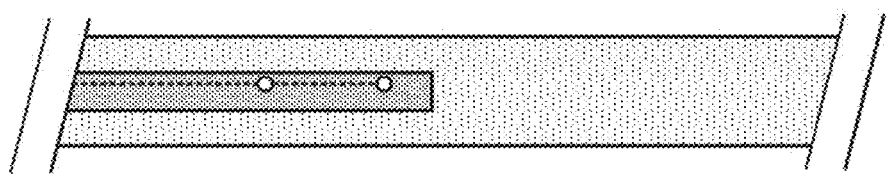
Figure 6C:
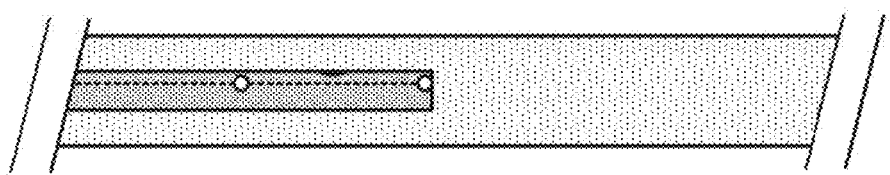
Figure 6D:
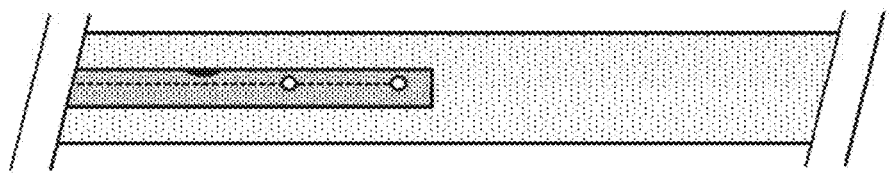
Figure 6E:
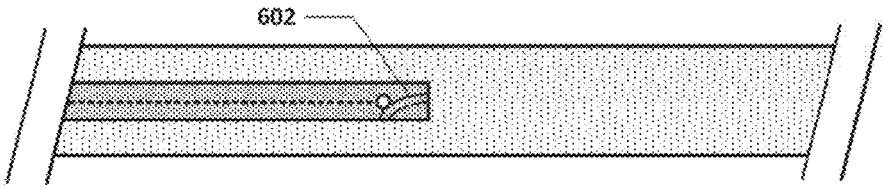

FIG. 6A shows an embodiment with an opening between two sensors, both of which are near, but not at, the catheter tip. FIG. 6B shows an embodiment with more than one sensor near, but not at, the tip of the catheter. FIG. 6C shows an embodiment with an opening between two sensors, one of which is at the catheter tip. FIG. 6D shows an embodiment which includes an opening proximal to 2 sensors. FIG. 6E shows an embodiment with channel 602. Channel 602 allows fluid to flow within the catheter, in proximity to a sensor within the catheter.

It is apparent that numerous variations of these and other embodiments of the vascular catheter navigation device are envisioned. For example, sensors, openings, channels etc. may be on different sides of the catheter and/or guidewire/stylet. Sensors, openings and channels are shown here at or near the catheter tip, however, they may be located anywhere along the catheter and/or guidewire/stylet.

Figure 7A:
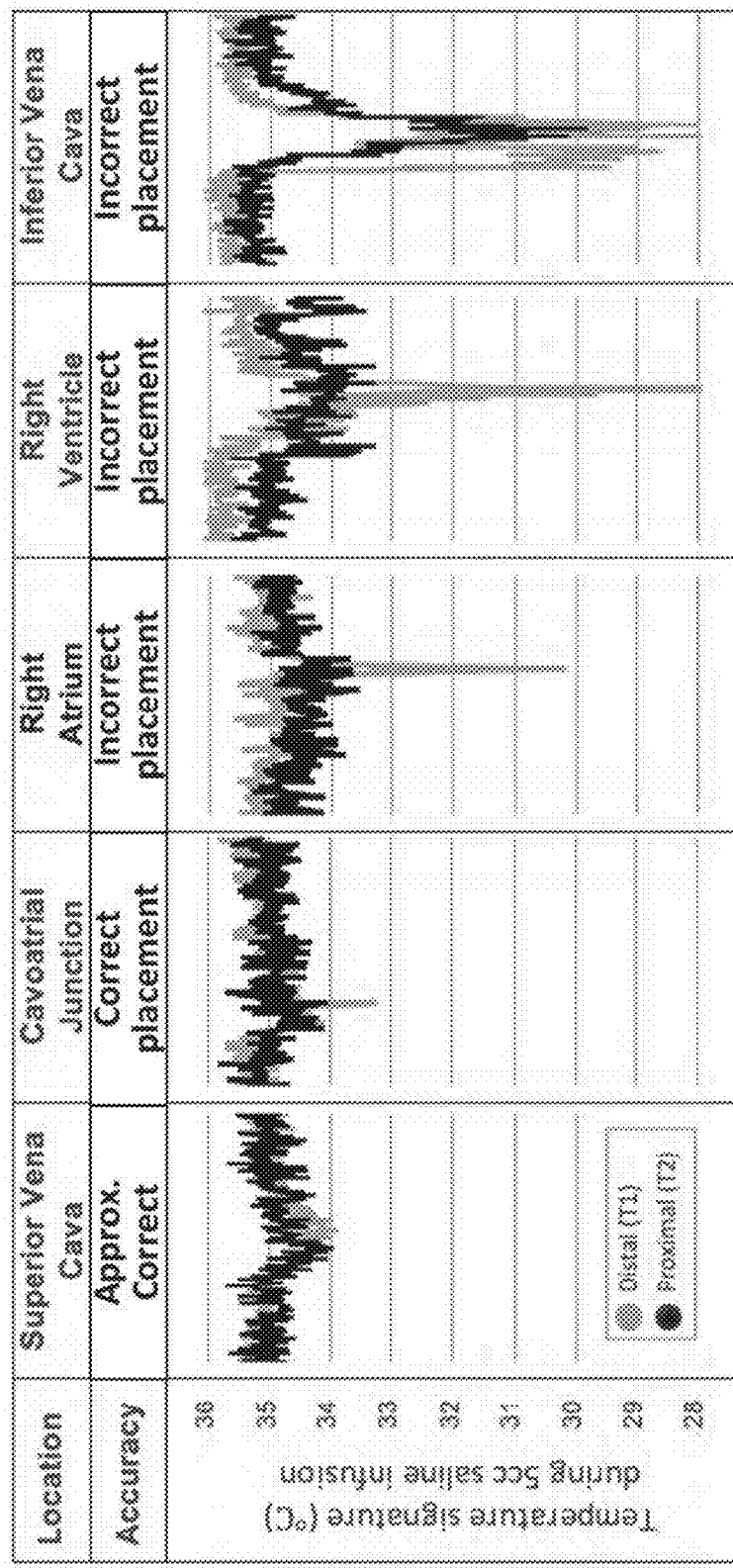
FIG. 7A shows temperature vs time data in various locations of the vasculature of a pig.

FIG. 7A shows temperature vs time data in various locations of the vasculature of a pig using one embodiment of the vascular catheter navigation device. The embodiment used to obtain this data had two temperature sensors—a distal sensor (T1) which was closest to the tip of the device (so in this instance, closest to the heart), and a proximal sensor (T2). The temperature vs. time curve is shown for both sensors for 5 different locations within the vasculature, the superior vena cava, the cavoatrial junction, the right atrium, the right ventricle, and the inferior vena cava. The first two locations, the superior vena cava and the cavoatrial junction, represent correct placement of the vascular catheter navigation device. The other three locations represent incorrect placement of the device. Note that the signatures of the right three temperature vs. time curves (representing incorrect placement) are different than the first two curves (representing correct placement or close to a correct placement). Also note that the right three curves are also able to be differentiated from each other. Different sensor configurations will result in different curve signatures in different vascular locations. For example, a single temperature sensor will give a different set of curves than will a system with 2 temperature sensors. The distance of the sensor(s) from the infusion exit site will also provide different curves. Different infusion rates, infusion volumes, infusion types (bolus vs. stream), infusion pressures, infusion velocities etc., will also provide different curves and thus different anatomical signatures. Different aspects of the curves may be analyzed by the controller to determine vascular location. These may include, but are not limited to, slope, magnitude, value, length, variability, standard deviation, shape, area under the curve, Fourier transform, frequencies, harmonics, etc. In some embodiments, certain frequencies in the data may be filtered out, including those relating to the heartbeat, system noise, etc.

In some embodiments there is one temperature sensor and therefore one temperature vs. time curve. In some embodiments there are two or more temperature sensors and therefore two or more temperature vs. time curves. The graphs of 2 temperature sensors are shown in FIG. 7A. In some embodiments, the infusion exit port is near the more proximal temperature sensor or temperature sensors. In some embodiments the infusion exit port is proximal or distal to the temperature sensor or temperature sensors. In some embodiments the infusion exit port is between the temperature sensors. In some embodiments, one or more than two temperature sensors may be used.

Figure 7B:
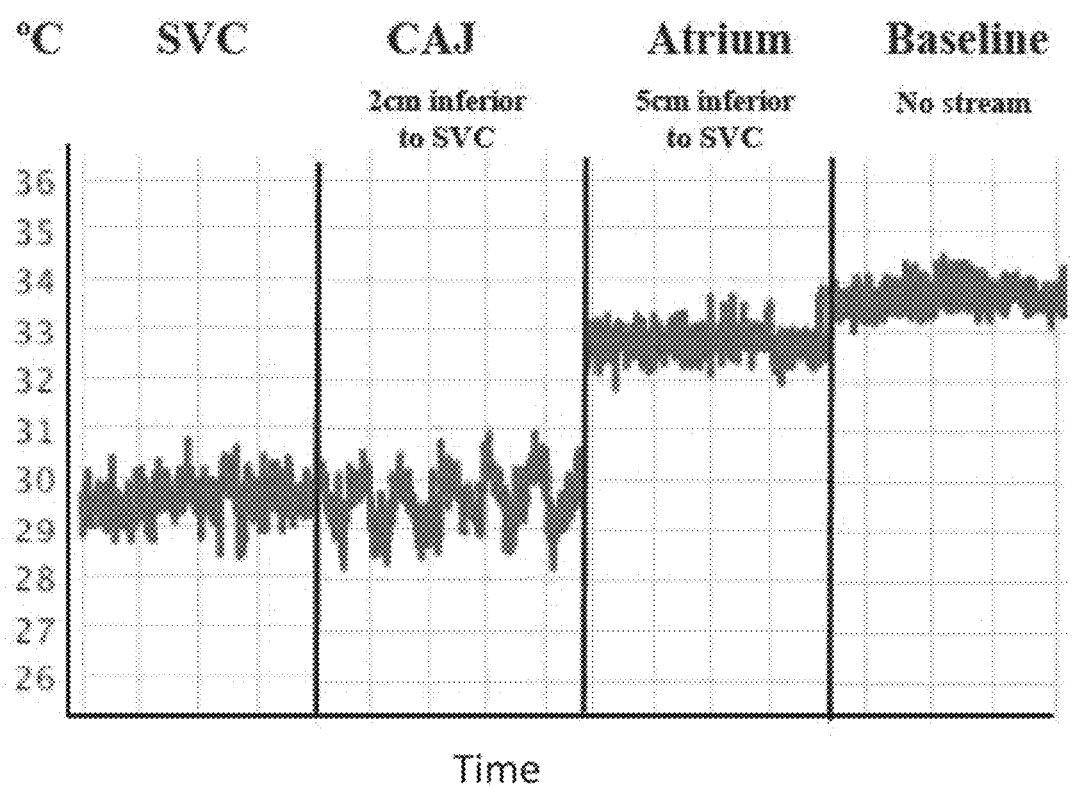
FIGS. 7B and 7C show temperature vs. time curves for varying embodiments of the vascular catheter navigation device.
Figure 7C:
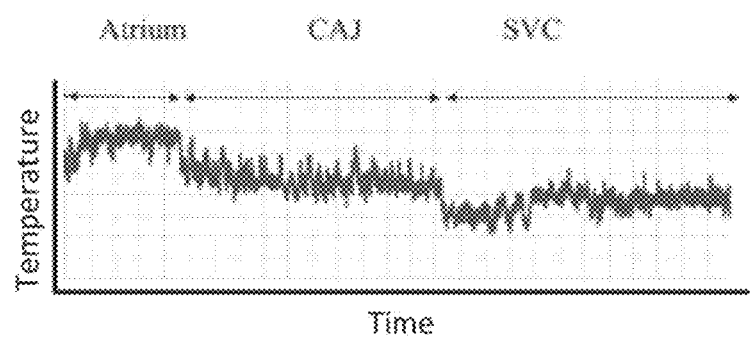

FIGS. 7B and 7C show two alternative temperature vs. time curves. Note that curves may appear different, in different anatomy, and based on the design of the vascular catheter navigation device. For example, the curve may be different for different sensor locations with respect to the fluid exit port. The curve may depend on the type of sensor or the fluid injection rate. The curve may depend on the initial temperature of the injection fluid. Other design factors may also result in different temperature vs. time curve shapes.

In addition, calibration of the temperature vs. time curves may be performed by the controller. For example, a baseline measurement may be derived after insertion of the system, or at other points during use of the system. For example, a baseline measurement may be taken in the blood vessel before any injection fluid is injected, or at a particular injection rate. An example of this is shown in FIG. 7B. "Baseline" data are show in the graph where a temperature measurement was taken without any fluid injection through the system. This baseline measurement may be used in the controller's analysis of the data to determine the location of the vascular catheter navigation device within the anatomy.

Various properties of the temperature vs. time curves may be analyzed to determine the location of the vascular catheter navigation device. For example, curve amplitude, noise, standard deviation, shape, slope, value, area under the curve, Fourier transform, frequencies, harmonics, etc. of one or more curves may be used to determine the vascular catheter navigation device location within the vasculature. These same parameters may be compared between and among multiple temperature vs. time curves to determine vascular catheter navigation device placement location. For example, the location, relative location, magnitude, and/or relative magnitude of peaks (positive or negative) of the curves may be used to determine vascular catheter navigation device location. In addition, the difference between amplitude, noise, standard deviation, shape, slope, value, area under the curve, and/or Fourier transform, harmonics, frequencies of the data from the multiple temperature sensors may be used to determine vascular location. Depending on droplet size and/or infusion rate, an area under the curve, or Fourier transform may be used to analyze the temperature vs. time curve and thus vascular location. Additionally, a maximum, or a number of maxima, may be more relevant.

The term "droplet" used herein may mean a drop, a bolus, a stream, an intermittent stream, etc. when referring to the injectate.

FIG. 8 is a schematic showing fluid flow in different areas of the vascular system representing desired (correct) and undesired (incorrect) device placement. Arrows 802 show blood flow direction. Areas 804 show fluid (such as saline) infusion. Note how the different anatomical locations will yield different flow conditions and thus different dissipation patterns of the fluid infusion. Although 1 temperature sensor 806 is shown here, two, or three, or four or five or six or more may be used, in this, and any other embodiments disclosed herein.

FIGS. 9A-9E show various embodiments of the vascular catheter navigation device where two temperature sensors are on the guidewire/stylet. FIG. 9A shows stylet 910 with proximal temperature sensor 902 and distal temperature sensor 904. The injectate 906 in this embodiment exits at the distal tip of catheter 908, proximal, or near to proximal temperature sensor 902. Alternatively, the injectate may be injected through a lumen of the guidewire/stylet. Although 2 sensors are shown here, one, or more than 2 may be used.

FIG. 9B shows an embodiment where the injectate is injected through the stylet/guidewire and exits between the two temperature sensors. FIG. 9C shows an embodiment where the injectate is injected through the stylet/guidewire and exits near or distal to the distal temperature sensor. If one temperature sensor is used, the fluid injection exit port may be either proximal to, or distal to the sensor.

FIGS. 9D and 9E show an embodiment with two temperature sensors on the stylet/guidewire where the guidewire is able to be moved with respect to the end of the catheter. This embodiment may be used to alter the sensing and/or injectate exit location with respect to the tip of the catheter.

For example, in some embodiments, the stylet/guidewire may include both the injection lumen (i.e. the stylet/guidewire may be hollow) and a temperature sensor so that it may be positioned in the anatomy first and/or independently of the vascular catheter. For example when jugular access is being used for catheterization. Once the stylet/guidewire is placed, the vascular catheter may be advanced so that the distal tip of the catheter is at a known position relative to the distal tip of the stylet/guidewire. The stylet/guidewire may then be removed.

Figure 9F:
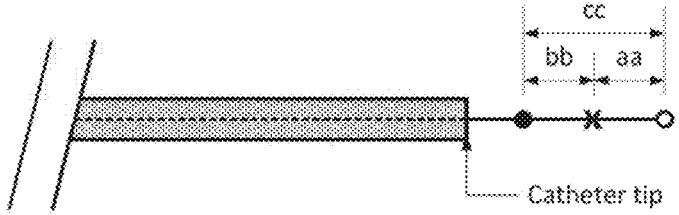
FIGS. 9F-9J show distances between the fluid ports and the temperature sensors.
Figure 9G:
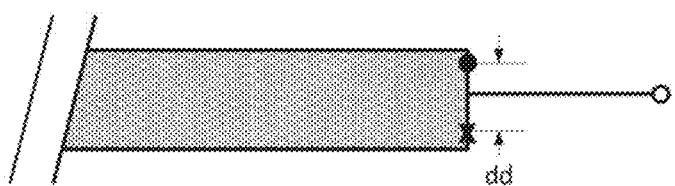
Figure 9H:
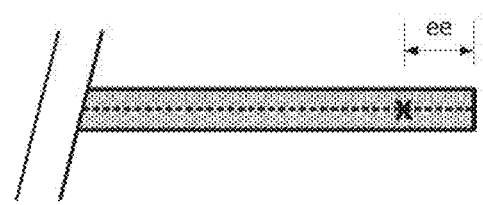

FIGS. 9F through 9H show distances between the fluid exit port and the temperature sensor(s) and distances between the catheter/stylet tip and the sensor(s)/ports. FIG. 9F shows the axial distance aa between the injectate exit or port, and the distal or singular temperature sensor. The axial distance bb is the distance between the fluid exit port and the proximal temperature sensor. The axial distance cc is the distance between the distal temperature sensor and the proximal temperature sensor. These distances may be positive or negative. Although 2 temperature sensors are shown here, the device may have one sensor or more than 2 sensors.

Distance aa may be about 0 mm. Alternatively, distance aa may be a range of about 0 mm to about 0.5 mm, or about 0 mm to about 1 mm. Alternatively, distance aa may be a range of about 0 mm to about 2 mm. Alternatively, distance aa may be a range of about 0 mm to about 3 mm. Alternatively, distance aa may about 3 mm to about 5 mm. Alternatively, distance aa may about 5 mm to about 10 mm. Alternatively, distance aa may be a range of about 0 mm to about 100 mm. These distances may alternatively be negative. For example, distance aa may be about 1 mm or may be about −1 mm. In the case of 1 mm, the distal temperature sensor will be distal to the fluid exit port. In the case of −1 mm, the fluid exit port will be distal to the distal temperature sensor. This is true for all dimensions provided in association with FIGS. 9F-9H.

Distance bb may be about 10 mm. Alternatively, distance bb may be a range of about 0 mm to about 10 mm. Alternatively, distance bb may be a range of about 8 mm to about 12 mm. Alternatively, distance bb may be a range of about 5 mm to about 15 mm. Alternatively, distance bb may be a range of about 1 mm to about 100 mm. Alternatively, distance bb may about 3 mm to about 5 mm. Alternatively, distance bb may about 5 mm to about 10 mm. Alternatively, distance bb may be a range of about 0 mm to about 100 mm. These ranges may also be negative distances.

Distance cc may be about 10 mm. Alternatively, distance cc may be a range of about 0.0 mm to about 5 mm Alternatively, distance cc may be a range of about 5 mm to about 15 mm. Alternatively, distance cc may be a range of about 15 mm to about 20 mm. Alternatively, distance cc may be a range of about 1 mm to about 100 mm.

Distance dd in FIG. 9G is the distance between the fluid exit port and either the distal or proximal temperature sensor. The distance is shown with respect to the proximal temperature sensor here, but distance dd may apply to either. Alternatively, only one temperature sensor may be present. Distance dd may be about 0.75 mm. Alternatively, distance dd may range from about 0.25 mm and 1.5 mm. Alternatively, distance dd may range from about 0.1 mm and 5 mm.

FIG. 9H shows the axial distance ee between the fluid exit port and the end of the catheter and/or stylet. Distance ee may be about 0 mm. Alternatively, distance ee may range from about 0 mm and about 1 mm. Alternatively, distance ee may range from about 0 mm and about 3 mm. Alternatively, distance ee may range from about 0 mm and about 5 mm. Alternatively, distance ee may range from about 5 mm and about 10 mm. Alternatively, distance ee may range from about 0 mm and about 100 mm. These distances may be positive or negative.

Figure 9I:
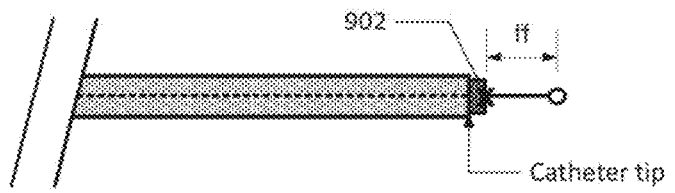

FIG. 9I shows an embodiment of the vascular catheter navigation device which includes only one sensor and includes conduit 902 in the system. Various embodiments of the system including a conduit will be described in more detail elsewhere herein. Conduit 902 incorporates the injectate exit port shown by an X. Distance ff shown here is the longitudinal distance between the fluid injectate exit port of the conduit and the sensor.

Figure 9J:
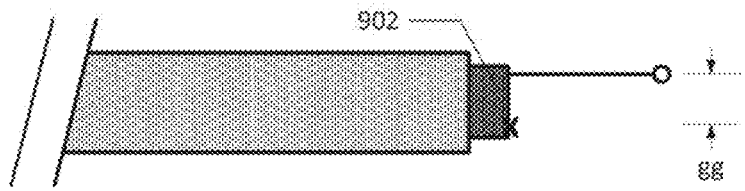

FIG. 9J shows an embodiment similar to that in FIG. 9I where the distance gg represents the radial distance between the fluid injectate exit port of the conduit and the sensor.

Figure 10:
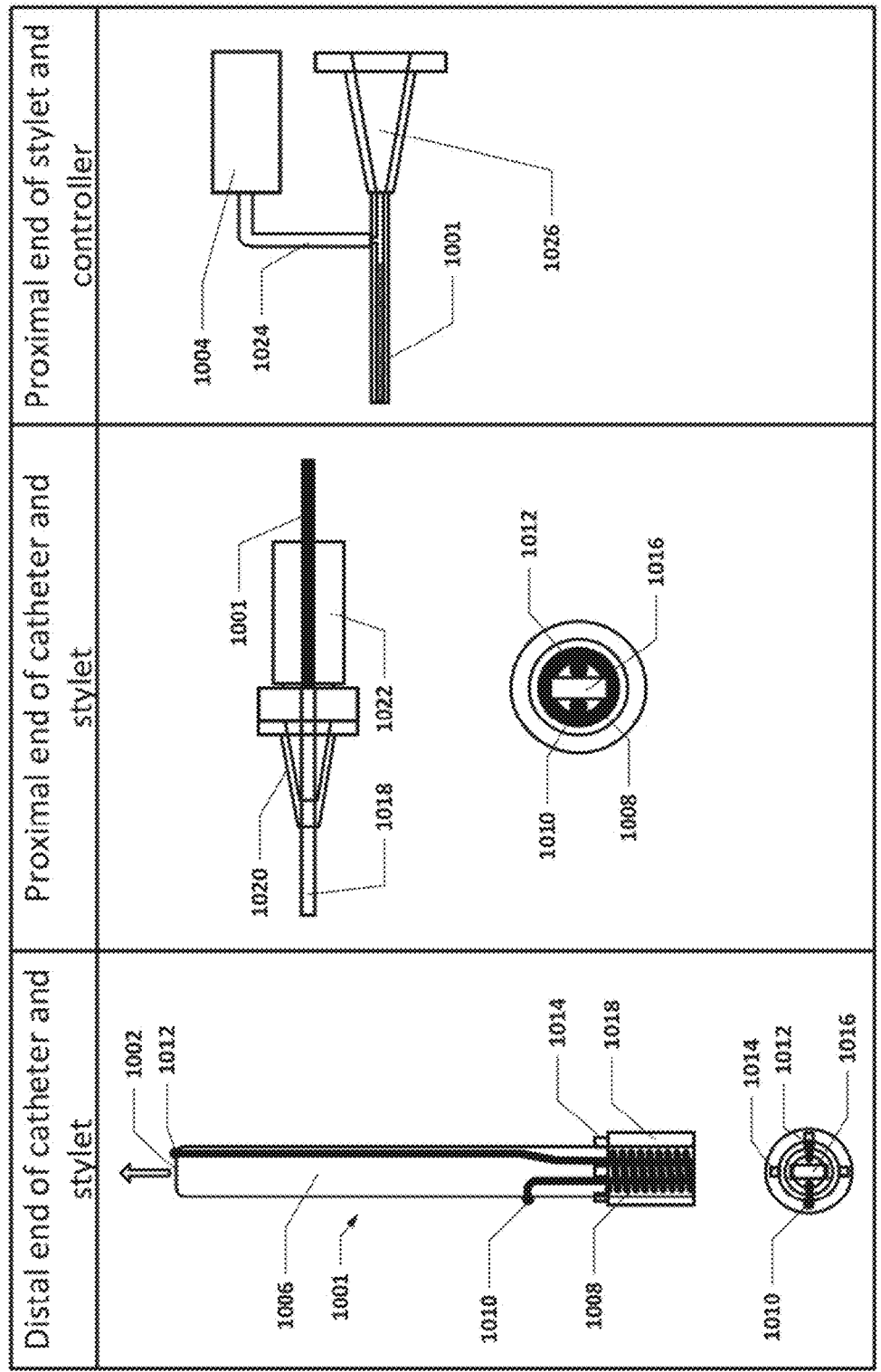
FIG. 10 shows an embodiment of the vascular catheter navigation device which can be used with any catheter.

FIG. 10 shows an embodiment of the vascular catheter navigation device which can be used with any catheter, or in other words, where the temperature sensor(s), the injectate lumen, the controller, and locking mechanism are included with the stylet/guidewire. FIG. 10 shows an embodiment with two thermocouples, distal thermocouple 1012 and proximal thermocouple 1010, and injectate exit port 1002 as part of guidewire/stylet 1001. Alternatively, the stylet/guidewire may only have one temperature sensor, or may have more than two temperature sensors. The stylet/guidewire may include features 1014 to help align the stylet/guidewire and the catheter. This embodiment may include a tip portion 1006, such as a molded urethane, nylon, silicone, or other polymer portion, for embedding the temperature sensor(s). Also shown here is an optional guidewire/stylet coil 1008 and the distal tip of catheter 1018. In the cross sectional view, injection lumen 1016 can also be seen.

This embodiment may include torque or locking device 1022 which may be used to lock the stylet to the proximal end of the catheter, for example using luer lock 1020 at the proximal end of catheter 1018. The torque/locking device may be locked to the stylet/guidewire so that the stylet/guidewire won't move with respect to the vascular catheter. Controller (not shown) may include and/or control an infusion mechanism via fluid port 1026 as well as read data from the temperature sensor(s) via temperature port 1004. The controller may be located near the proximal end of the stylet, or may be located several inches or feet from the proximal end of the stylet. Temperature sensor leads 1024 are also shown. The infusion may be steady or intermittent or consist of boluses.

FIGS. 11A-I show various views of various embodiments of a stylet/guidewire version of the vascular catheter navigation device.

The stylets shown in 11A-11I and some other embodiments serve several functions, including: 1) Stiffening of the catheter to aid in insertion 2) providing a medium for fluid delivery and 3) providing a channel for the wiring for the temperature sensor or sensors. FIG. 11A is a cross section of the stylet such as that shown in the embodiment of FIG. 10. Two temperature sensors are shown here, but the device may include one, or more than two sensors.

FIG. 11B shows an embodiment of a stylet which includes three components in a triple lumen, heat shrink, and/or tubing housing 1102 which contains two temperature sensors 1104 and fluid lumen 1016. Alternatively, one or more than two temperature sensors may be present.

FIG. 11C shows an embodiment in which the stylet coil is made all, or in part, out of the temperature sensor wires. FIG. 11D is a side view of the embodiment shown in FIG. 11C.

Figure 11E:
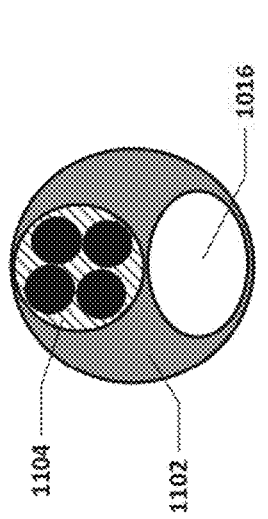

FIG. 11E shows an embodiment including an extrusion, or tube, (metal or plastic) which houses two temperature sensors as well as a fluid lumen. Alternatively, one or more than two temperature sensors may be present.

Figure 11F:
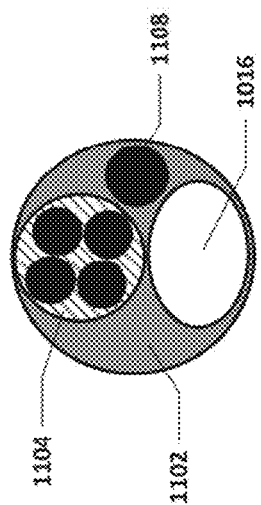

FIG. 11F shows an embodiment including an extrusion, or tube, (metal or plastic) which houses multiple thermocouples within one bundle as well as a fluid lumen.

Figure 11I:
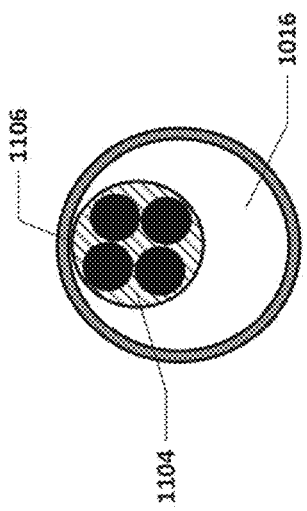
Figure 11G:
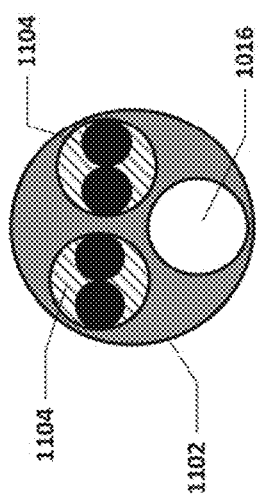

FIG. 11G shows an embodiment including a thin walled extrusion, or tube, where the temperature sensors are surrounded by the fluid lumen. One, two, or more than two temperature sensors may be present.

Figure 11H:
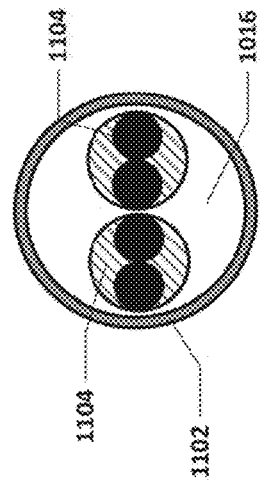

FIG. 11H shows an embodiment including an extrusion, or tube, (plastic or metal) which includes multiple temperature sensors, a fluid lumen, as well as stiffener 1108 which may be a wire or a rod. One, two, or more than two temperature sensors may be present.

FIG. 11I shows an embodiment including an extrusion, or tube, (plastic or metal) which includes a temperature sensor bundle as well as a fluid lumen. The temperature sensor bundle exterior may be made of similar material to the outer extrusion which enables optional chemical or heat formed bond or weld 1106. One, two, or more than two temperature sensors may be present.

In some embodiments, it may be important to either fix, or precisely control, the distance between the catheter tip and the guidewire/stylet, or be able to determine the distance between the catheter tip and the guidewire/stylet. It may also be important to able to fix the location of the injection with respect to a temperature sensor or to know the distance between the location of the injection exit port and a temperature sensor. The distance between the exit port and the temperature sensors will have an effect on the temperature profile during fluid infusion. These distances may be fixed across patients and scenarios, or may be different for different patient types and different scenarios. For example, the distance may be different depending on the vasculature being accessed. The distance may be different for patients of different weight, size, body mass index, health, age, sex, heart condition, or other patient characteristics. The distance may be different for different catheter sizes, catheters with different numbers and shapes of lumens etc.

In some embodiments, the stylet/guidewire is fixed, or locked, with respect to the catheter tip using a torque device near the proximal end of the catheter as shown in FIG. 10.

In some embodiments, the user determines the relative alignment of the catheter and stylet/guidewire by sight and then measures the relative distance from two values.

FIGS. 12-17 show various embodiments of the vascular catheter navigation device which include various registration techniques to either fix, or know, the distance between the temperature sensor or sensors on the stylet, and the catheter tip or fluid injection point.

FIG. 12 shows an embodiment with an indicator on the stylet/guidewire which is a fixed and known distance from a temperature sensor. In this embodiment, the user aligns the tip of catheter 1202 with indicator, or mark 1204, on stylet 1206 before insertion into the patient. The relative distance 1208 of the catheter tip to the tip of the stylet may be locked, preferably at the proximal end, using a torque device, a locking rotating hemostasis valve, a tuohy-borst valve, or other locking mechanism, before the catheter is inserted into the patient. The indicator on the guidewire/stylet may be a visible mark, such as a red stripe or dot, or a tactile mark, such as a bump or groove, or other type of indicator.

FIG. 13 shows an embodiment with raised area, or bump 1302, on the stylet which is a fixed and known distance from the distal temperature sensor. This allows the user to align the tip of the catheter with the bump on the stylet, either visually, or by tactile feel. This alignment may be done outside the body or inside the body. In some embodiments, the bump is small or soft enough that the stylet may be removed from the catheter after placement in the anatomy.

FIG. 14 shows an embodiment similar to that shown in FIG. 13 where a temperature sensor 1104 acts as the bump on the stylet.

FIG. 15 shows an embodiment where jig, or block, or aligner 1502, is used to align the tip of the catheter a fixed and known distance from the tip of the stylet. The relative location of the catheter with respect to the stylet is then locked, at the proximal end, using a torque device, a locking rotating hemostasis valve, a tuohy-borst valve, or other locking mechanism, and/or at the distal end, using a securing style conduit (disclosed in detail elsewhere herein), or both. Jig or block 1502 may itself be adjustable so that it can align the fluid exit port (here the distal end of the catheter) with the temperature sensor for a variety of different lengths.

Figure 16:
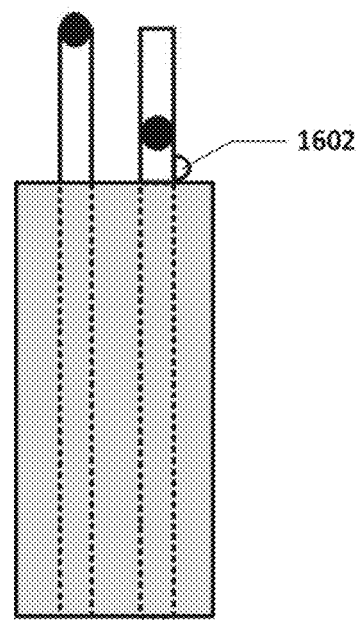

FIG. 16 shows an embodiment similar to that shown in FIG. 13 where inflatable balloon 1602 is used as the bump to align the catheter and the stylet. The balloon may be annular or on one or more sides of the stylet. The balloon may be inflated for use during alignment, and either left inflated during placement, to lock the stylet in position with respect to the catheter, or deflated during placement (where the catheter and stylet have been locked to each other using a torque or valve). In this embodiment, the stylet or catheter will include an inflation lumen to inflate and deflate the balloon. The balloon may be deflated for removal of the stylet after placement of the catheter.

Figure 17:
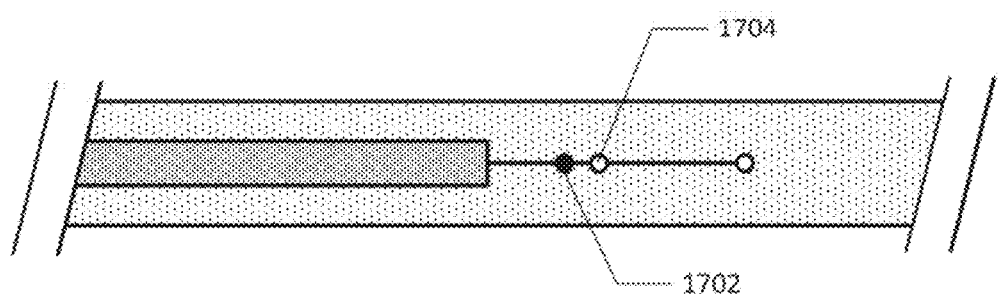
Figure 24A:
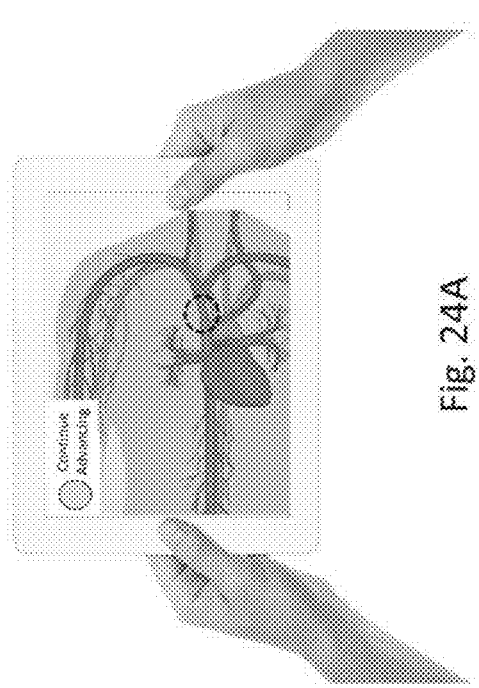
Figure 24B:
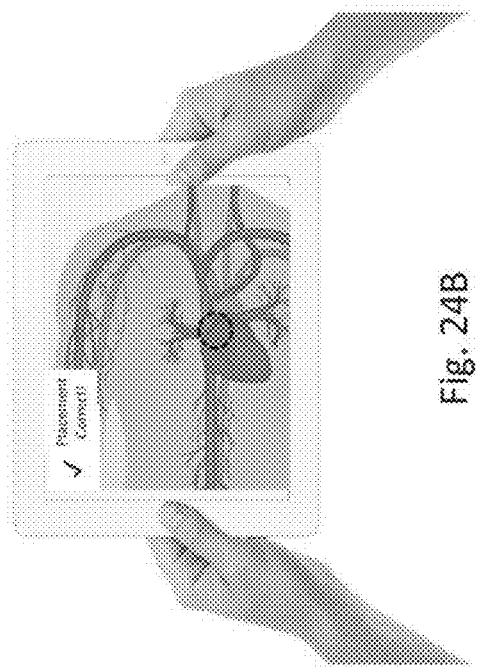
Figure 24C:
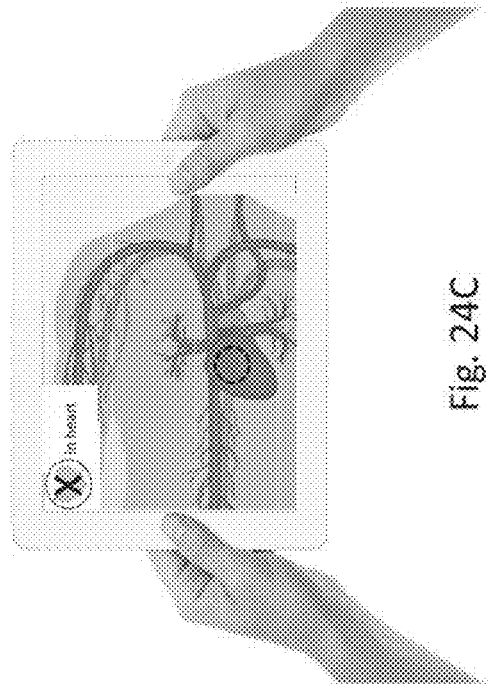
Figure 24D:
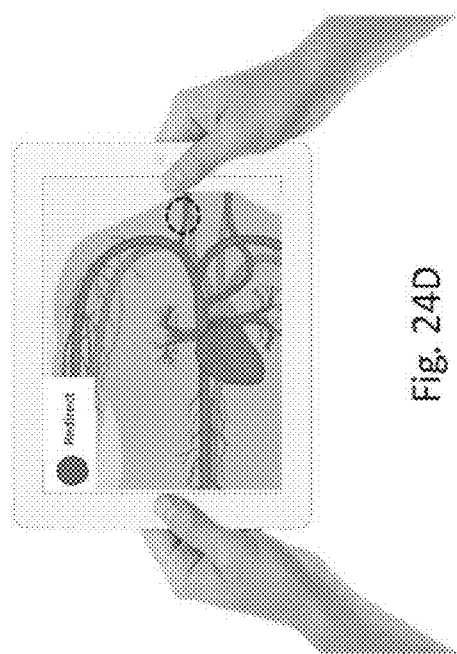

FIG. 17 shows an embodiment of the vascular catheter navigation device which includes a sensor 1702 which can sense when it is inside the catheter tip during use. For example the sensor may be magnetic, ultrasound, light, temperature, etc. In some embodiments, proximal temperature sensor 1704 is used as a sensor to determine when the proximal temperature sensor is inside the catheter tip. The temperature vs. time curve shape after injection of injectate will show a specific profile when the temperature sensor is just inside the catheter tip, and can be used to identify this alignment. This embodiment may include one, two, or more temperature sensors.

In some embodiments, controlling the flow patterns of the injectate exit may be important. to achieve consistent results. It may also be important to contrast the flow of the injectate with that of the blood flow within the vasculature/heart. The flow of the injectate may be purposefully made either more laminar or more turbulent to achieve these goals. Some embodiments may include features that direct the flow and are a part of the catheter or stylet. These features may be surface features, like dimpling, or an orange peel finish, that change the surface finish of the catheter or stylet. These features may be part of the OD of stylet/temp sensors or ID of fluid lumen or both.

FIGS. 18A and B show 2 possible embodiments for a flow director (to create laminar or turbulent flow) in injectate lumen 1016 of the vascular catheter navigation device. Flow director 1802 may be at the end of the injectate lumen, as shown in FIG. 18A, or it may be set back from the tip of the lumen exit, as shown in FIG. 18B.

FIGS. 19A-C show other embodiments of the vascular catheter navigation device where the shape of the injectate lumen controls the type of flow of the fluid exiting the lumen. Some of the parameters which may be varied include injectate lumen opening area, shape, surface condition, etc. Temperature sensor and/or stiffener 1902 is also shown.

Some embodiments may vibrate the stylet and/or catheter to create turbulent flow of the injectate from the injectate lumen.

FIG. 20 shows an embodiment of a stylet without an injection lumen. The fluid may be introduced through another catheter lumen (possibly on a separate catheter) upstream from the catheter tip, closer to the insertion site, or elsewhere. For example, fluid may be injected via "buddy" catheter 2002 shown here alongside the vascular catheter. Fluid may also be heated or cooled via a heating/cooling element on the catheter or on a "buddy" catheter. An infusion "buddy" guidewire/stylet is also envisioned.

FIG. 21 shows features 2102 in the injectate lumen that enhance a controlled turbulent flow.

FIG. 22 shows features 2202 in the injectate lumen that create a controlled laminar (or less turbulent) flow.

Note that several embodiments disclosed herein show 2 sensors. In any of these embodiments, one, two, or more sensors may be used.

In some embodiments the outer diameter (OD) of the stylet is around 1 mm or less. In some embodiments the OD of the stylet is around 0.5 mm or less. In some embodiments the OD of the stylet is around 1.5 mm or less. In some embodiments the stylet could range in OD from about 0.2 mm to about 5 mm.

In some embodiments, where the catheter is double or triple lumen, the stylet functionality may be broken into distinct parts (fluid, stiffener, temperature sensing) etc. and multiple stylets may be used in multiple lumens of the catheter.

Many types of temperature sensors may be used in any of the embodiments disclosed herein, including thermocouples, fiber optic, resistive, bimetallic, thermometer, state-change, silicon diode, thermistors, optical temperature measurement (infrared or otherwise), mercury thermometers, manometers, etc.

In addition to infusing fluids, as disclosed elsewhere herein, other methods to create a thermal change at or near the tip of the catheter/stylet may be used. Fluids at a temperature higher than body temperature may be introduced, a resistive heating element, or a piezo electric cooling element, etc. may be included in the catheter, on the catheter, on the guidewire/stylet, or at the injector, outside of the body. Alternatively, the injected fluid may be at a different, although not strictly controlled, temperature than body temperature and this temperature difference (between body temperature and injectate temperature) is measured and tracked by the controller.

In embodiments with a resistive heating element, the resistive heating elements may be on the catheter or on a stylet. In embodiments where it is on the catheter it may be on the outside of the catheter or on the inside of one or more lumens of the catheter. Alternatively, it may be on the guidewire/stylet. In embodiments where it is on the guidewire/stylet, it may be within the catheter lumen, partially within the catheter lumen, or external to the catheter lumen, where it is exposed to blood. When heating/cooling blood, injection of an injectate may not be required.

As shown in FIGS. 23A-E and FIGS. 24A-E. A graphical user interface may be displayed in the form of a small screen/display 2314, a large screen, a projection, in virtual reality or augmented reality goggles, etc. The major categorization of user interactions may have any combination of user alerts: 1) icon 2) color of icon or warning light 3) auditory tone that accompanies the alert 4) visual map of the body which matches the location of the catheter tip and with the type of alert 5) written phrase or word on the display indicating the status or alert, vibration, etc. The categories may be the following: 1) 'Continue Advancing', which means that that the catheter tip is advancing through a peripheral vein or has rounded the bend and is approaching the superior vena cava. This mode will be accompanied by visual and auditory feedback indicating a positive state such as green lighting and iconography and a positive tone. 2) 'Placement Correct', with the checkmark iconography shows that the tip has arrived at the proper location—the cavo atrial junction for PICC lines, or perhaps another location for another type of catheter insertion. Positive tone and lighting may also accompany this state. 3) If the catheter encounters an opposing flow, the warning, 'Redirect' may appear. This is the warning if the catheter advances down an azygous branch, advances into the IVC, or has been placed in an artery. Since this is not a positive state, lighting or iconography that is red, yellow or orange may accompany this state along with a tone which depicts that a non-favorable situation is in effect. A less pleasant frequency, pitch and tone may accompany. 4) if the catheter is in the heart, either in the atrium or the ventricle, the user may be alerted with the heart icon and/or "In Heart" warning. A negative color and tone may accompany this state. 5) if the catheter tip is up against a wall of a vein, or has an obstruction of some kind the "Adjust" warning may display. A negative color and tone may accompany this state. Also shown in FIGS. 23A-E and 24A-E is catheter 2302, stylet 2304, temperature adapter 2306, fluid adapter 2308, prime button 2310, and insertion/tracking button 2312.

The graphical user interface (GUI) may display in real time the location of the tip of the catheter relative to the 3D space through which it is navigating. The graphical user interface shown in FIGS. 23A-E and 24A-E are two dimensional, however some embodiments include 3D displays which may also communicate the information in three dimensions.

Note that although some embodiments disclosed herein incorporate the sensor(s) into the vascular catheter, the vascular catheter navigation device may be a stand-alone device which fits inside a vascular catheter, and can be removed once vascular catheter placement has been completed. The vascular catheter navigation device, for example, may serve as a stylet or guidewire for a standard vascular catheter.

Figure 25C:
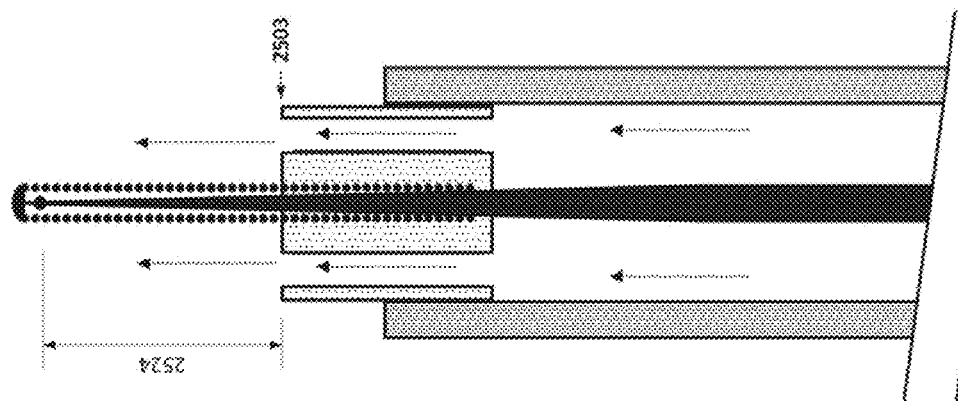
FIGS. 25A-C show embodiments of the vascular catheter navigation device which include a conduit to control fluid flow exiting from the device.
Figure 25B:
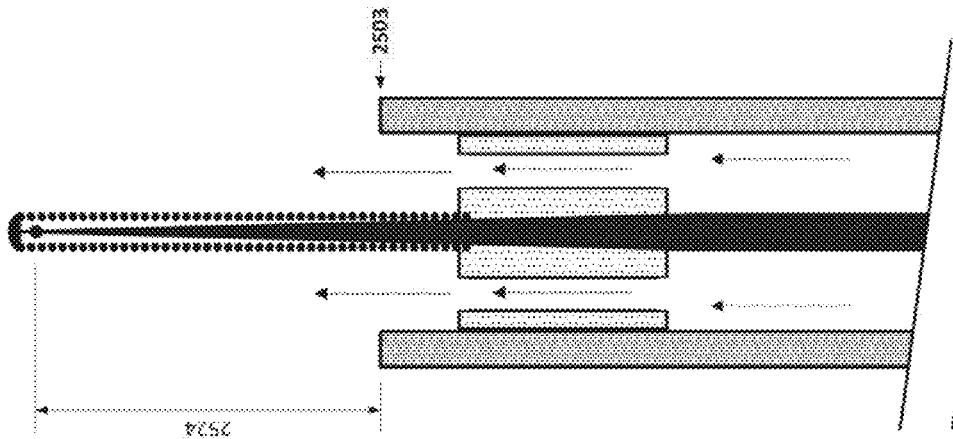
Figure 25A:
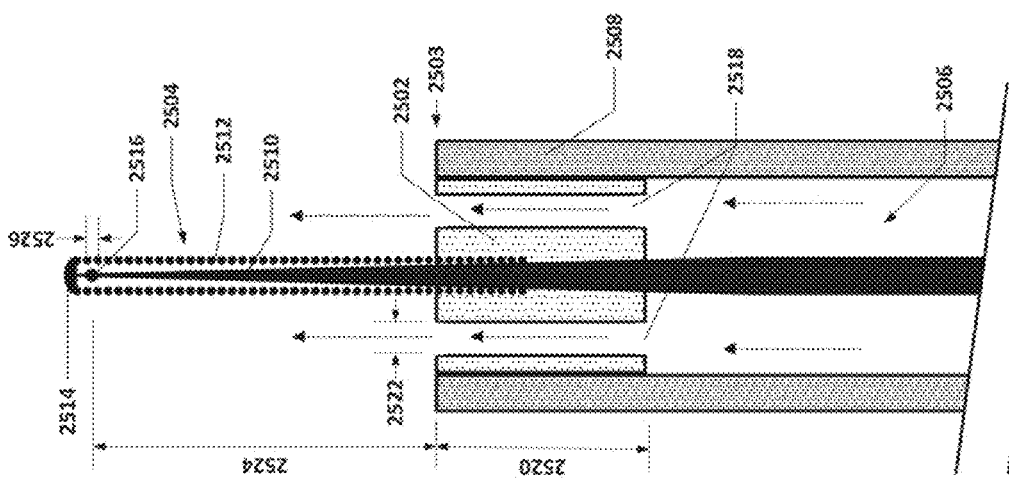

FIGS. 25A-C show embodiments of the vascular catheter navigation device which include a conduit to control fluid flow exiting from the fluid exit point of the device. In this embodiment, conduit 2502 is attached to guidewire/stylet 2504, forming a stylus/conduit combination device. Conduit 2502 is designed to fit inside the ID of infusion lumen 2506 of vascular catheter 2508. In this figure, vascular catheter 2508 only includes one lumen, the infusion lumen, however multiple lumens, in addition to the infusion lumen, may exist in the vascular catheter.

In some embodiments, guidewire/stylet 2504 includes core 2510, coil 2512, endcap 2514 and temperature sensor 2516. Core 2510 may include a stiffening wire, which may be tapered, and leads for the temperature sensor. The temperature sensor may be incorporated into the endcap, or it may be separate. One or more temperature sensor(s) may be present. The temperature sensor may be a thermocouple. A larger cross sectional dimension of the thermocouple may dampen temperature measurements where a smaller cross sectional dimension of the thermocouple may allow for quicker response times. The diameter or cross sectional dimension 2526 of a thermocouple may be about 0.2 mm-0.3 mm. Alternatively, the diameter or cross sectional dimension 2526 of a thermocouple may be about 0.02 mm to about 0.5 mm.

In some embodiments, conduit 2502 has length 2520 and includes fluid flow passage or passages 2518 with diameter or cross sectional dimension 2522. The flow passages may be circular in cross-sectional shape, or oval, or of any shape. A flow passage may be approximately 0.4-0.6 mm in diameter or cross sectional dimension. Alternatively a flow passage may be approximately 0.1-1.0 mm in diameter or cross sectional dimension. Alternatively a flow passage may be approximately 0.01-2.0 mm in diameter or cross sectional dimension. Conduit length 2520 may be about 4-8 mm. Alternatively, conduit length 2520 may be about 0.5 mm-20 mm.

The cross sectional area and shape of the flow passages will determine flow velocity exiting the conduit. The number of flow passages will also affect the flow parameters of the fluid exiting the conduit. Preferably, the fluid infusion rate may be about 2-3 ml/min. Alternatively, the fluid infusion rate may be about 3-5 ml/min. Alternatively, the fluid infusion rate may be about 5-10 ml/min. Alternatively, the fluid infusion rate may be about 1-5 ml/min. Conduit exit flow velocity is preferably about 60-100 cm/sec. Alternatively, conduit exit flow velocity is about 1-300 cm/sec.

Conduit 2502 may serve several purposes:

1) Essentially sealing the distal end of the infusion lumen of the vascular catheter while allowing fluid flow through/past the conduit so that when fluid is infused through the infusion lumen of the catheter, the majority of the fluid exits the vascular catheter via flow passage(s) 2518. It is important to note that the conduit doesn't fully occlude the infusion lumen of the catheter, it allows fluid to pass through it and in some cases, through channels around it.

2) Allowing the distance 2524 between the fluid exit point 2503 and the sensor on the guidewire/stylet to be known and fixed for more controlled temperature measurements in the vasculature. The fluid exit point may be the exit point of the distal end of the flow passage(s) of the conduit, or may be the distal end of the catheter, depending on whether the conduit is partially sticking out of the distal end of the catheter. Distance 2524 may be about 0.0 to 1.0 mm. Alternatively, distance 2524 may be about 0.5 to 1.0 mm. Alternatively, distance 2524 may be about 0.0 to 2.0 mm. Alternatively, distance 2524 may be about 0.0 to 5.0 mm. Alternatively, distance 2524 may be about 0.0 to 10.0 mm. "about 0.0" or "Essentially zero" herein may mean plus or minus 1 mm, or "Essentially zero" may mean plus or minus 2 mm, or "Essentially zero" may mean plus or minus 3 mm. This may be the case with any of the embodiments disclosed herein.

3) Centering or otherwise aligning the fluid exit point(s) of the conduit with the temperature sensor(s).

4) centering or otherwise aligning the fluid exit point(s) with the catheter tip 5) Controlling the flow characteristics of the fluid exiting the exit point(s). For example, the size, shape and number of exit ports will control the flow characteristics of the fluid exiting the port(s). Parameters such as turbulence, flow velocity, volumetric flow rate, flow volume, etc. may be controlled. The cross-section of the flow passages 2518, in addition to the fluid infusion rate, will determine the velocity of the infusion rate exiting the flow passages 2518. The velocity of the infusion rate may be adapted to the velocity of the blood flow.

Allowing the outer surface of the conduit to essentially seal with the inner surface of the infusion lumen of the vascular catheter without having to perfectly align the guidewire/stylet with the vascular catheter. Because the vascular catheter is larger, and more flexible, than the stylet, the relative alignment of the distal tips of each may vary during a procedure. Where the length of the conduit is longer than this variance, the conduit can still seal the infusion lumen of the vascular catheter even if the distal tips of the stylet/conduit combo and the vascular catheter move with respect to each other. Alternatively or additionally, the conduit may fix the guidewire/stylet to the vascular catheter so that one does not move substantially relative to the other at least longitudinally.

The cross sectional dimension/diameter of the conduit may be about 0.5-1.5 mm. Alternatively, the cross sectional dimension/diameter of the conduit may be about 0.1-3 mm. The clearance between the outside of the conduit and the inside of the infusion lumen of the vascular catheter in some embodiments will be small enough to allow an essential seal between the outside of the conduit and the inside of the infusion lumen of the vascular catheter. This encourages essentially all the infused fluid to exit flow passages 2518 which controls the distance between the fluid exit and the temperature sensor. The clearance between the outside of the conduit and the inside of the infusion lumen of the vascular catheter may also be great enough to allow the stylet/conduit combination to move within the infusion lumen of the vascular catheter, for positioning, and/or for removal. The outer surface of the conduit may be coated or manufactured from a lubricious material, such as PTFE, a hydrophobic material, a hydrophilic material, etc. The clearance between the outside of the conduit and the inside of the infusion lumen of the vascular catheter may be about 0.070-0.080 mm. Alternatively, the clearance between the outside of the conduit and the inside of the infusion lumen of the vascular catheter may be about 0.05-0.1 mm. Alternatively, the clearance between the outside of the conduit and the inside of the infusion lumen of the vascular catheter may be about 0.001-1.00 mm.

Note that the clearance between the outside of the conduit and the inside of the infusion lumen of the vascular catheter may be different for embodiments of the conduit which expand/contract, or have features which expand/contract, such as those shown in FIGS. 27, 28, 29A-C, 30, 36A-C. For example, the clearance in the contracted state may be greater than that of a conduit which does not expand/contract and the clearance in the expanded state may be less than that of a conduit which does not expand/contract. For example, the clearance in the expanded state may be essentially zero.

FIG. 25A shows the distal end of conduit 2502 essentially aligned with the distal end of catheter 2508. (Note that "distal" herein means the end of the vascular catheter navigation device which enters the body. "Proximal" herein means the end of the vascular catheter navigation device which does not enter the body.) FIG. 25B shows an embodiment where the distal end of the conduit is designed to sit inside the distal end of the infusion lumen of the catheter for infusion. FIG. 25C shows an embodiment where the distal end of the conduit is designed to sit outside the distal end of the infusion lumen of the catheter for infusion. Note that some embodiments may be designed to sit in more than one position.

The fluid exit point 2503 is shown for the devices in FIGS. 25A-25C and in other figures. Note that the exit point may be the distal end of the conduit, or the distal end of the catheter, depending on the alignment of the conduit with the distal end of the catheter.

In use, the stylet/conduit combination device is inserted (or comes inserted) into the infusion lumen of the vascular catheter. The catheter is then inserted into, advanced through, the vasculature. As the device is advanced, fluid is infused through the infusion lumen. Because the conduit essentially seals the infusion lumen of the catheter, the fluid exits the system through the flow passages of the conduit, and the fluid flows through the vasculature and the temperature of the blood/fluid in the vasculature is sensed by the temperature sensor. The distance between the exit point(s) of the fluid and the temperature sensor is fixed/known and the temperature vs. time curve is related to the flow characteristics within the vessel. The different signatures of these curves are used to identify the location of the tip of the vascular catheter navigation device. After the system has been navigated to its desired location, the stylet/conduit combination device is removed, and the infusion lumen of the vascular catheter serves as a standard infusion lumen. The stylet/conduit combination device may be reinserted into the infusion lumen of the vascular catheter later on to confirm the location of the tip of the vascular catheter.

Figure 26:
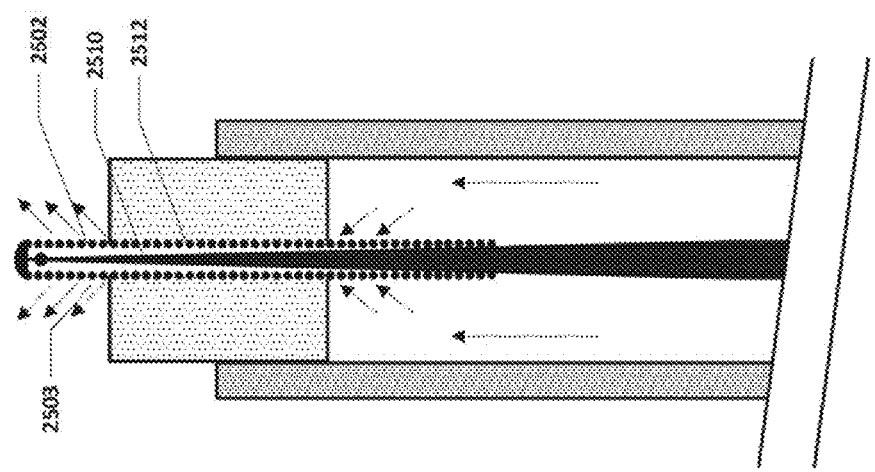
FIG. 26 shows an embodiment of the vascular catheter navigation device where the flow passage is within the guidewire/stylet component itself.

FIG. 26 shows an embodiment of the vascular catheter navigation device where the flow passage is within the guidewire/stylet component itself. In this embodiment, the conduit serves to essentially seal the end of the infusion lumen of the catheter, but the flow passage flows between stylet core 2510 and stylet coil 2512 and exits via openings 2602 between the coils.

Figure 28:
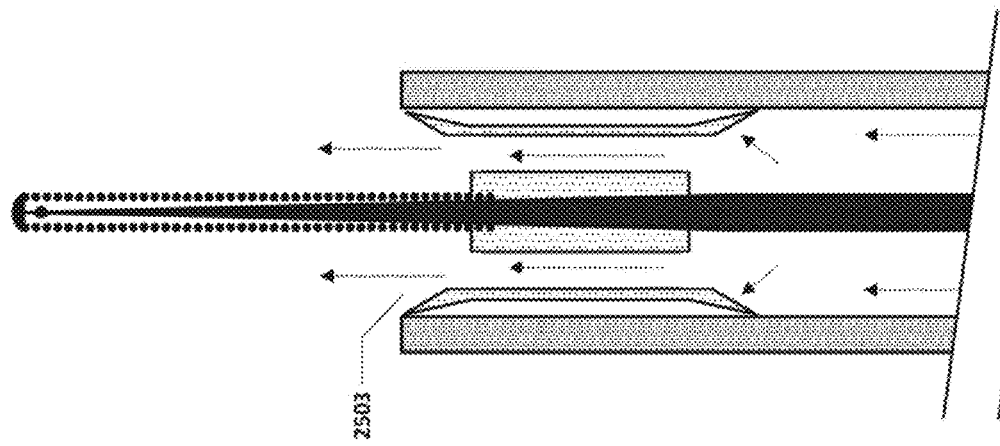
FIG. 28 shows a variation of the embodiment shown in FIG. 27 where the conduit has both a proximal flange and a distal flange.
Figure 27:
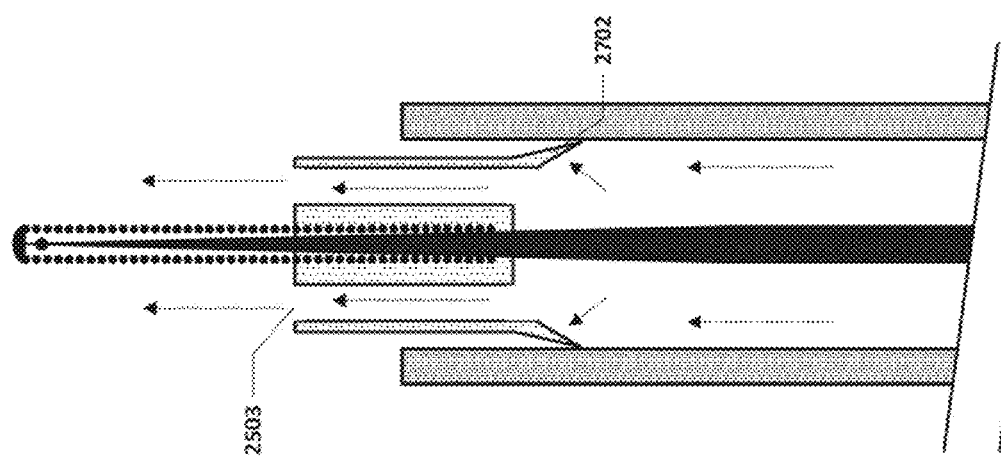
FIG. 27 shows a variation of the conduit which includes a proximal flange.

FIG. 27 shows a variation of the conduit which includes proximal flange 2702. The flange may serve as a seal, essentially sealing the conduit to the ID of the infusion lumen of the catheter, when fluid injected through the infusion lumen of the catheter above a certain pressure. When fluid is no longer infused through the infusion lumen, or when the infusion pressure is reduced below a certain pressure, flange 2702 may collapse slightly, reducing the diameter or cross sectional area of the conduit at the flange, which allows the stylet/conduit combination device to be removed from the vascular catheter after location of the vascular catheter has been established. Alternately, the flange may invaginate and flip direction during withdrawal movement, easing removal of the stylet/conduit combination device. FIG. 28 shows a variation of the embodiment shown in FIG. 27 where the conduit has both a proximal flange and a distal flange. Note that, in these, as well as other embodiments disclosed herein, during use, i.e., during catheter navigation, the distal end of the conduit may be flush with the distal tip of the catheter, distal to the distal end of the catheter, or proximal to the distal end of the catheter.

Figure 29C:
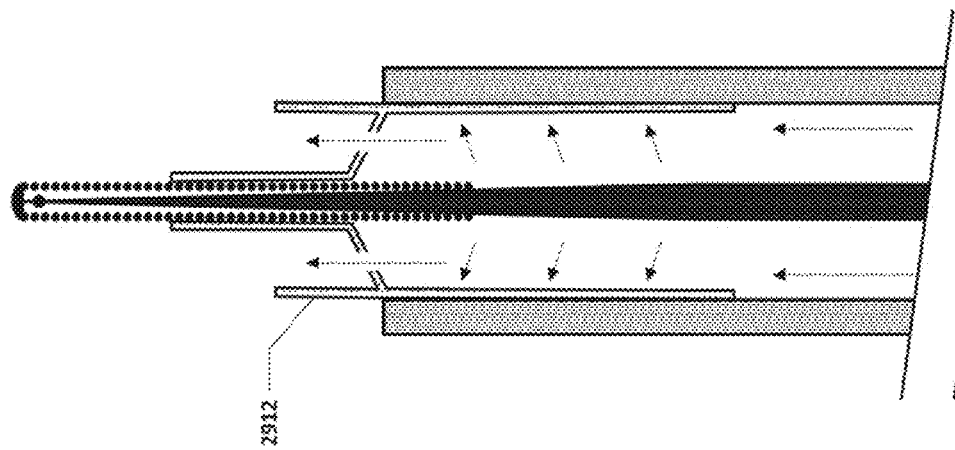
FIGS. 29A-C show an embodiment of the vascular catheter navigation device where the conduit includes a thin-walled inflatable structure.
Figure 29B:
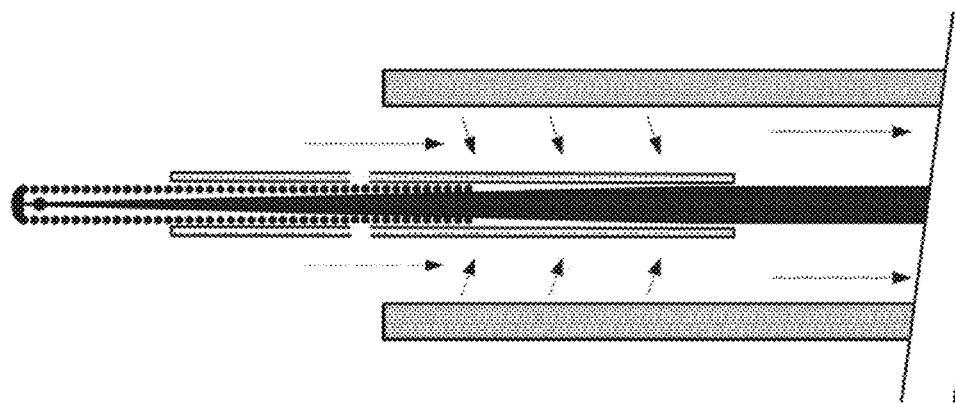
Figure 29A:
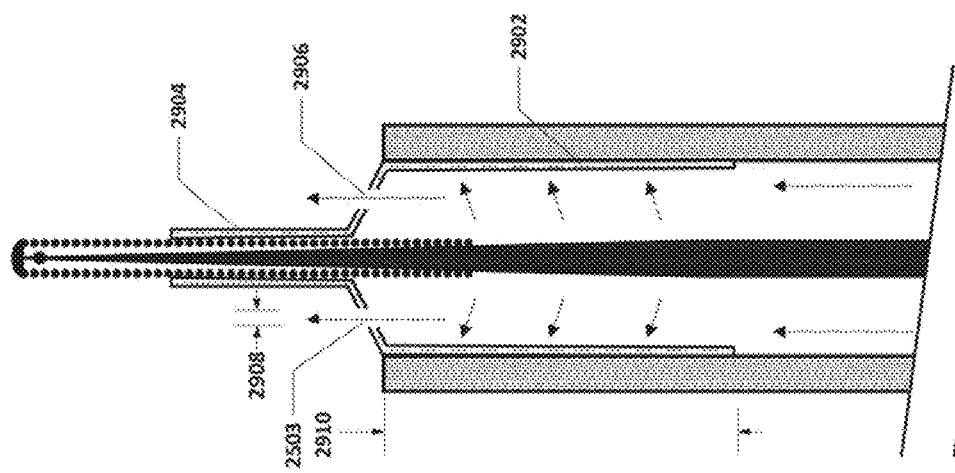

FIGS. 29A-C show an embodiment of the vascular catheter navigation device where the conduit includes a thin-walled inflatable structure. FIG. 29A shows a conduit with thin-walled, inflatable proximal portion 2902 and distal portion 2904, where distal portion is bonded, or otherwise attached, to the stylet. Proximal portion 2902 of the conduit includes opening(s) 2906. Proximal conduit portion 2902 expands when fluid in infused through the infusion lumen of the catheter, essentially sealing the inflatable portion up against the inner walls of the infusion lumen. The infusion fluid also exits the catheter via openings 2906. The openings must be small enough to allow the pressure within portion 2902 to increase so that this portion "inflates" inside the infusion lumen. The openings must be large enough to allow adequate fluid to escape into the blood stream to make meaningful temperature measurements. The diameter or cross-sectional dimension of the opening(s) may be about 0.4-0.06 mm. Alternatively, the diameter or cross-sectional dimension of the opening(s) may be about 0.05-1.0 mm. The length 2910 of proximal section 2902 of the conduit may be about 0.3-0.5 mm. Alternatively, the length 2910 of proximal section 2902 of the conduit may be about 0.3-20 mm.

To remove the stylet/conduit component from the vascular catheter, the fluid infusion is reduced, or reversed, to "deflate" proximal section 2902 of the conduit so that the stylet/conduit can be removed. This is shown in FIG. 29B. In some embodiments, deflation may not be necessary and the stylet/conduit may be removed from the vascular catheter while fluid infusion is taking place.

FIG. 29C shows a variation of the inflatable conduit with collar 2912 which may help direct fluid flow as it exits the conduit.

One of the advantages of an "inflatable" conduit is that the shape of the conduit can conform to any shaped infusion lumen, whether round, semi-circle, triangular, oval, etc. The difference in cross sectional area between the deployed vs. un-deployed conduit can be fairly great, which is useful in smaller infusion lumen devices.

Figure 30:
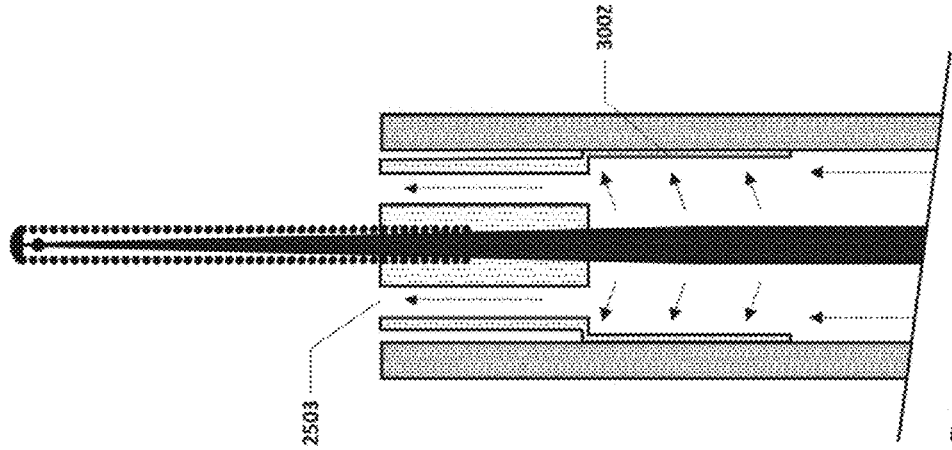
FIG. 30 shows an embodiment which includes a thin-walled "skirt".

FIG. 30 shows an embodiment of the conduit which has thin-walled "skirt" 3002. This "skirt" expands and contracts similar to the "inflatable" portion of the embodiment shown in FIGS. 29A and B.

Figure 32:
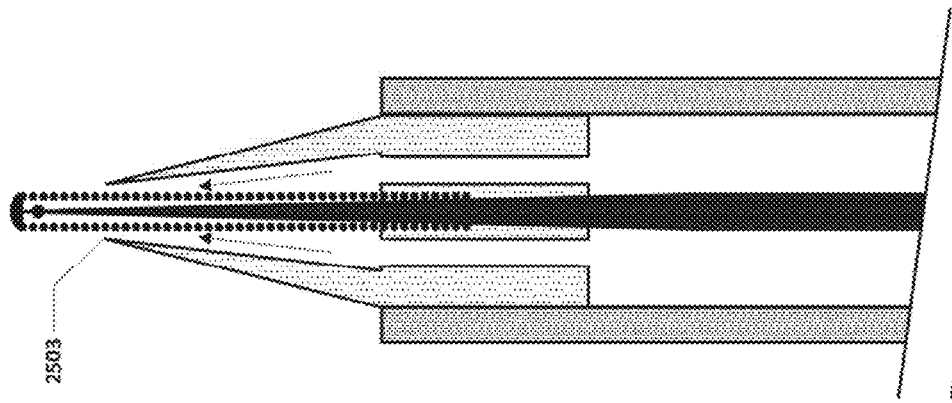
FIGS. 31-33 show embodiments where the conduit includes feature(s) to help direct the fluid flow exiting the conduit.
Figure 31:
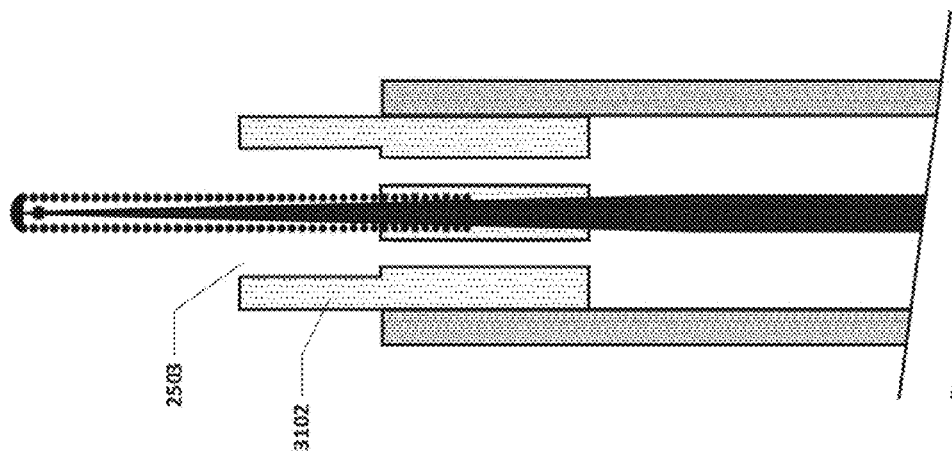
Figure 33:
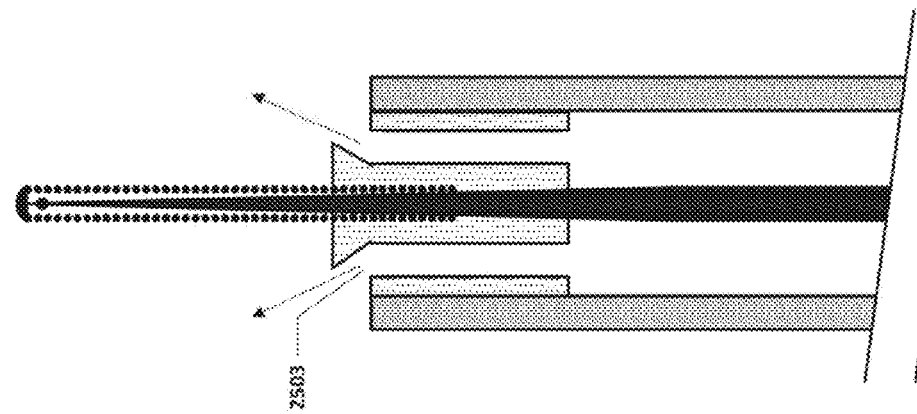

FIG. 31 shows an embodiment of the conduit which includes feature(s) 3102 to help direct the fluid flow exiting the conduit. The feature may direct flow in a parallel manner, as shown in FIG. 31, inward, as shown in FIG. 32, or outwardly, as shown in FIG. 33, or in any other manner.

Figure 34:
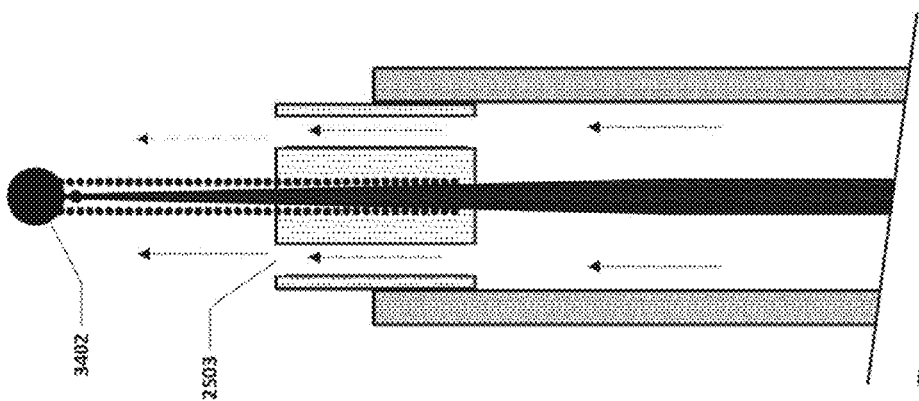
FIG. 34 shows an embodiment with a deflector.

FIG. 34 shows an embodiment with deflector 3402 which helps keep the system away from the wall of the blood vessel. The deflector may be a sphere, or essentially spherical in shape or any other shape. The diameter or cross section dimension of the deflector may be about 0.3-0.4 mm. Alternatively, the diameter or cross sectional dimension of the deflector may be about 0.01-1.0 mm.

Figure 35:
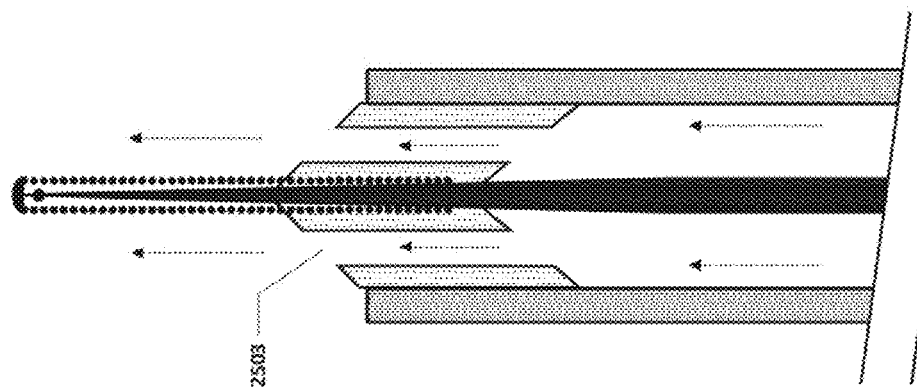
FIG. 35 shows an embodiment of the conduit which is conical shaped.

FIG. 35 shows an embodiment of the conduit which is conical shaped to help seal within the infusion lumen of the catheter during injection.

FIGS. 36A-C show an embodiment of the vascular catheter navigation device which includes a compressible conduit 3606. The compressible conduit may be made out of silicone, polymer, or other suitable material. FIG. 36A shows the conduit in its compressed state. In this state, the conduit essentially seals the infusion lumen of the catheter. FIG. 36B shows the compressible conduit in its uncompressed state, which reduces the diameter/cross-sectional dimension so that it may be repositioned and/or removed. The compressing/uncompressing of the conduit may be performed by rod or hypotube or tube 3602 which is connected to the proximal end of the compressible conduit and can be manipulated (pushed, pulled, twisted etc.) from the proximal end of the catheter to compress and uncompress the conduit. FIG. 36C shows a variation of the system which allows the user to compress/uncompress the conduit by rotating rod/hypotube/tube 3604 which has threads which engage with the conduit. (New embodiment idea: A very small balloon could be used to initiate and remove the seal. This is more applicable for very large catheters.)

FIGS. 37A-F show 2 different cross-sectional views of various embodiments of the vascular catheter navigation device. FIG. 37A shows an embodiment where guidewire/ stylet 2504 is generally centered in conduit 2502 within infusion lumen of vascular catheter 2508. Flow passage(s) 2518 may have different cross sectional shapes, for example, spherical, triangular, those shown here and others. One, two, or more flow passages may be present. The guidewire/stylet may include sensor lead wires 3702.

FIG. 37B shows an embodiment of the vascular catheter navigation device where the guidewire/stylet is off center. The cross sectional views show various possible configurations of the guidewire/stylet and fluid passages. The flow passage(s) may be circular, crescent shaped etc. one, two or more flow passages may be present in any of the embodiments disclosed herein. Note that the conduit may be a simple tube, as shown by 3704.

FIG. 37C shows an embodiment of the vascular catheter navigation device where the guidewire/stylet is off center and the tip of the guidewire/stylet is angled to align with flow passage in the conduit so that temperature sensor 2516 is approximately aligned with a flow passage. The tip of the guidewire/stylet may be aligned in other ways as well, for example, to fall between flow passages or to simple be near the center of the catheter. The cross sectional views show various possible configurations of the guidewire/stylet and fluid passages. The flow passage(s) may be circular, crescent shaped etc. The conduit may be a simple tube.

FIG. 37D shows an embodiment of the vascular catheter navigation device where the conduit is a simple tube, and the guidewire/stylet is either floating in the ID of the conduit (here the ID of the conduit is the same as the flow passage of the conduit), or attached to the inner wall of the conduit. The guidewire/stylet may be angled so that the temperature sensor is more aligned with the center of the conduit flow passage, or straight, or bent or curved in some other way.

FIG. 37E 37D shows an embodiment of the vascular catheter navigation device which includes cage or scaffold 3706 which centers sensor 2516 over a central flow passage within the conduit. The cage/scaffold may be made from metal wire, polymer, may be made from a porous material, etc. Cage/scaffold may be embedded in, or attached to, the conduit.

FIG. 37F shows an embodiment of the vascular catheter navigation device where conduit 2502 does not have an outer surface. In this embodiment, flow passages are in direct contact with the ID of catheter 2508.

Figure 38A:
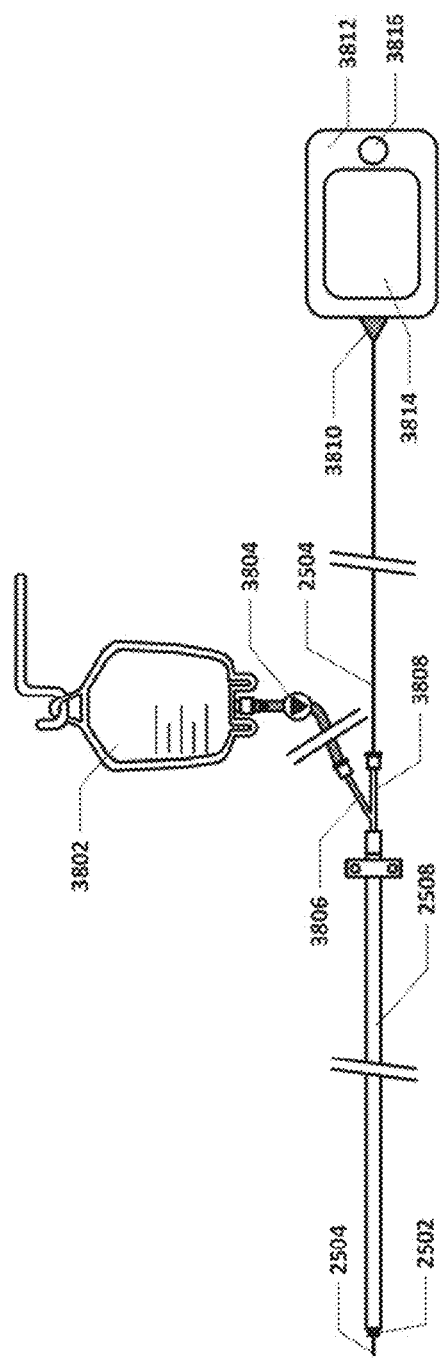
FIGS. 38A-E show various embodiments of the vascular catheter navigation device.
Figure 38B:
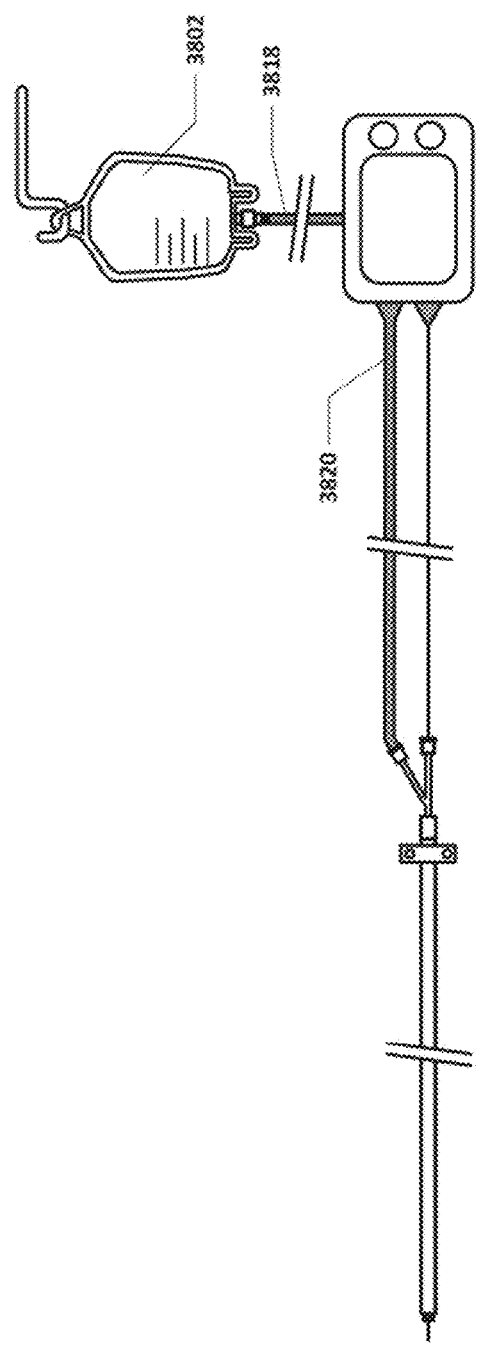

FIGS. 38A-E show some possible architectures of various embodiments of the vascular catheter navigation device. FIG. 38A shows vascular catheter 2508, guidewire/stylet 2504 and conduit 2502, along with IV bag 3802, with optional infusion pump 3804, where the infusion bag is connected to the fluid infusion port 2806 of the vascular catheter. The guidewire/stylet is inserted/removed to/from the catheter via stylet port 3808. In some embodiments, the stylet port of the catheter may be the same port as the infusion port. Stylet/sensing connector 3810 connects to controller 3812, which may include display 3814, as well as one or more controls 3816. In this embodiment the infusion of fluid through the vascular catheter and through the flow passage(s) of the conduit is controlled by the IV bag/infusion pump. The IV bag may be set to a consistent drip, flow, and/or may be controlled by the infusion pump. In this embodiment, the IV bag and/or infusion pump, is connected to the vascular catheter without going through the controller. FIG. 38B shows a similar embodiment, except that the flow of IV fluid from the IV bag is controlled by the controller. IV bag 3802 is connected to the controller via IV fluid line 3818. The controller controls the infusion of fluid from the IV bag and delivers the fluid to the catheter via catheter fluid line 3820. The controller could be disposable or re-usable. The kit could also come with disposable lines which attach to the IV bag or hospital's infusion pump.

Figure 38C:
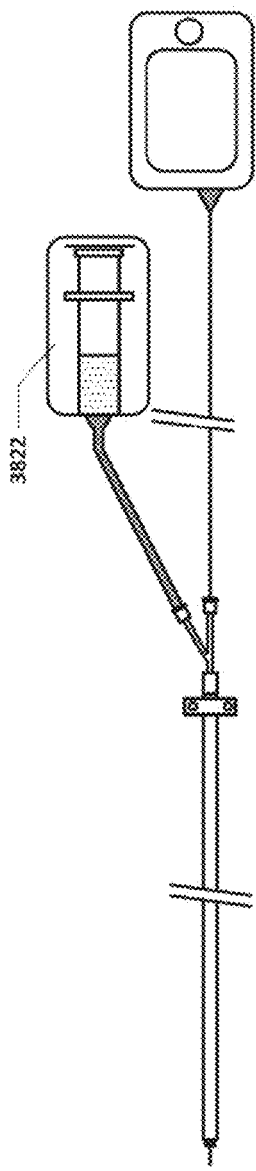

FIG. 38C shows an embodiment of the vascular catheter navigation device which includes fluid pump 3822, such as a syringe pump. The fluid pump may be a standard off the shelf fluid pump. Note that in this embodiment, the fluid pump does not connect to the controller.

Figure 38D:
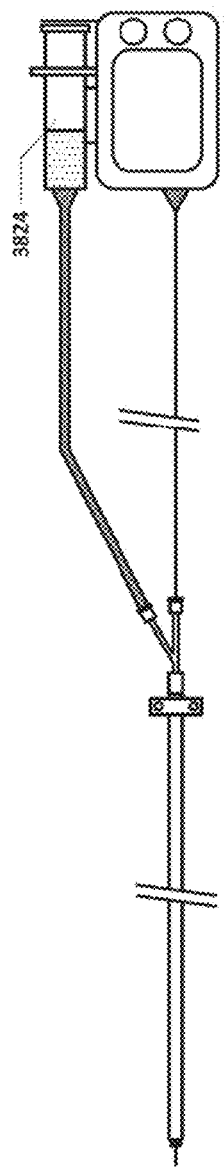

FIG. 38D shows an embodiment where fluid pump 3824 connects to the controller, so that the controller can control the fluid delivery to the catheter via the fluid pump. The controller may have a module that allows the user to attach an off the shelf fluid pump, or the controller may require a specific fluid pump. The fluid pump and/or the syringe cartridge within the fluid pump may be disposable.

Figure 38E:
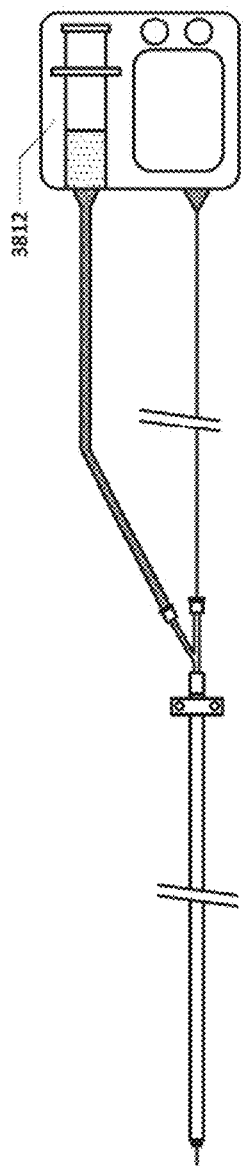

FIG. 38E shows an embodiment where the fluid pump is incorporated into controller 3812. The fluid pump and/or the syringe cartridge within the fluid pump may be disposable.

Figure 39A:
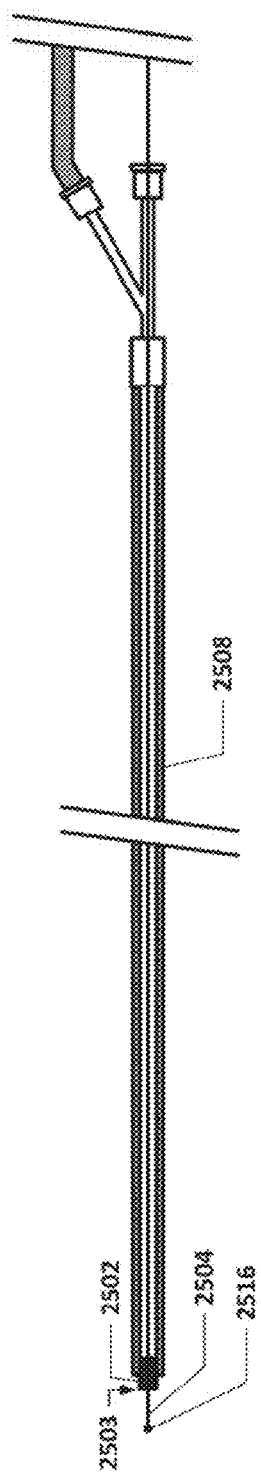

FIG. 39A is a longitudinal cross sectional view of the vascular catheter navigation device including conduit 2502, guidewire/stylet 2504, sensor 2516 and vascular catheter 2508.

Figure 39B:
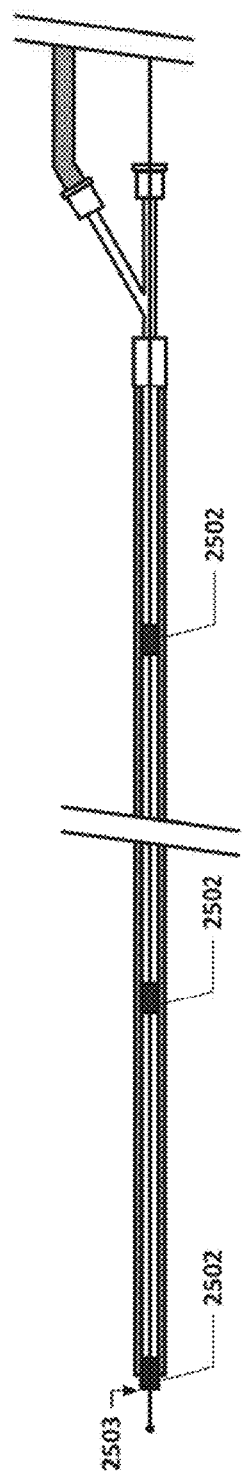

FIG. 39B shows an embodiment of the vascular catheter navigation device with multiple conduits along the length of the guidewire/stylet. There may be 0, 1, 2, 3, 4, 5, 6 or more conduits.

Figure 39C:
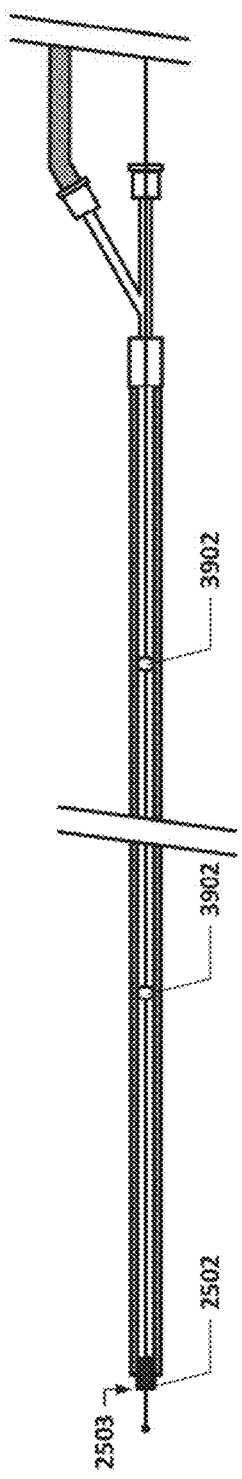

FIG. 39C shows an embodiment of the vascular catheter navigation device with conduit 2502, as well as securing style conduits 3902. In some embodiments, these securing style conduits are inflatable, such as balloons, but they may also be compressible, such as silicone or another soft/compliant material, such as any suitable polymer. The securing style conduit may alternatively be made from a harder material, such as epoxy, or metal, or polymer etc. Preferably, the securing style conduits secure the guidewire/stylet to the inner lumen of the catheter so that the stylet does not move significantly longitudinally with respect to the catheter. As a result, the distance between the fluid exit point, and the sensor, is essentially fixed. Movement of the sensor with respect to the fluid exit point may be limited to plus or minus 1 mm. Or Movement of the sensor with respect to the fluid exit point may be limited to plus or minus 2 mm. Or Movement of the sensor with respect to the fluid exit point may be limited to plus or minus 3 mm. Preferably, a securing style conduit also allows fluid to flow past it as it is securing, and through the catheter lumen during infusion. There may be zero, 1, 2, 3, 4, 5, 6 or more securing style conduits. In embodiments where the guidewire/stylet includes a balloon, it will also include an inflation lumen. Balloons may be relatively non-compliant or relatively compliant. The advantage of a non-compliant balloon is that it will retain its shape, or roundness, when inflated beyond a critical pressure. This will prevent the balloon from conforming to the infusion lumen thus filling it. Instead, a non-compliant balloon will remain relatively circular when inflated, and fluid flow lumens will be available between the inner wall of the catheter infusion lumen, the stiffener/electrodes, and the securing style conduit, as shown in FIG. 39G.

FIG. 39D shows an embodiment of the vascular catheter navigation device with securing style conduit 3902. In this embodiment, the securing style conduit may serve as the conduit. The securing style conduit may be at the tip of the catheter or it may be further back proximally from the tip of the catheter, by length 3904. Length 3904 may be about 0-0.5 mm. Alternatively, length 3904 may be about 0-1.0 mm. Alternatively, length 3904 may be about 0.5-1.0 mm. Alternatively, length 3904 may be about 0-5 mm. Alternatively, length 3904 may be about 0-10 mm. Alternatively, length 3904 may be about 0-20 mm. Alternatively, length 3904 may be about 0-30 mm. Alternatively, length 3904 may be about 0-40 mm. Alternatively, length 3904 may be about 0-50 mm. Alternatively, length 3904 may be about 0-60 mm. Alternatively, length 3904 may be about 0-70 mm. Alternatively, length 3904 may be about 0-80 mm. Alternatively, length 3904 may be about 0-90 mm. Alternatively, length 3904 may be about 0-100 mm.

Length 3905 is the length between the sensor and the tip of the catheter, which in this embodiment, is the fluid exit point. The securing style conduit secures the guidewire/ stylet to the infusion lumen of the catheter essentially fixing length 3905 during placement. Length 3905 may be about 0-0.5 mm. Alternatively, length 3905 may be about 0-1.0 mm. Alternatively, length 3905 may be about 0.5-1.0 mm. Alternatively, length 3905 may be about 0-5 mm. Alternatively, length 3905 may be about 0-10 mm. Alternatively, length 3905 may be about 0-20 mm. Alternatively, length 3905 may be about 0-30 mm. Alternatively, length 3905 may be about 0-40 mm. Alternatively, length 3905 may be about 0-50 mm. Alternatively, length 3905 may be about 0-60 mm. Alternatively, length 3905 may be about 0-70 mm. Alternatively, length 3905 may be about 0-80 mm. Alternatively, length 3905 may be about 0-90 mm. Alternatively, length 3905 may be about 0-100 mm.

The length of securing style conduit 3902 may be around 1 mm. Alternatively, the length of securing style conduit 3902 may be around 1-2 mm. Alternatively, the length of securing style conduit 3902 may be around 1-3 mm. Alternatively, the length of securing style conduit 3902 may be around 1-4 mm. Alternatively, the length of securing style conduit 3902 may be around 0.5-5 mm.

FIGS. 39E-39G show radial cross section views which reveal some of the embodiments of securing style conduit 3902. In FIG. 39E there are 3 balloons, or soft protrusions around guidewire/stylet 2504. FIG. 39F shows 2 balloons/ protrusions and FIG. 39G shows only one balloon/protrusion. Note that the flow passage(s) 3906 of these securing style conduits is the space(s) between the securing style conduit and the inner lumen of catheter 2508, and similar to the conduit shown in FIG. 37F, does not have an outer surface. In several of these embodiments, flow passages are in direct contact with the ID of catheter 2508.

In one embodiment, securing style conduit 3902 is a small silicone protrusion or inflatable balloon near the distal end of the stylet/guidewire and as such, serves as the conduit. Before insertion, the guidewire/stylet is placed into the desired position so that the temperature sensor is correctly positioned with respect to the distal tip of the catheter. At this point, the securing style conduit may be "activated", for example, by inflating the balloon. The securing style conduit holds the relative position of the guidewire/stylet and the catheter during the placement process. During the placement process, fluid is injected through the catheter, past the securing style conduit and out the distal tip of the catheter. For removal, the securing style conduit is either deflated, or is flexible enough to then allow the guidewire/stylet to be removed from the catheter. Sealing style conduit 3902, when activated may be at a cross sectional dimension which is greater than that of guidewire/stylet 2504. The cross sectional dimension of the conduit may be about 0.05 mm greater than that of the guidewire/stylet. Alternatively, the cross sectional dimension of the conduit may be about 0.05-0.1 mm greater than that of the guidewire/stylet. Alternatively, the cross sectional dimension of the conduit may be about 0.05-0.5 mm greater than that of the guidewire/stylet. Alternatively, the cross sectional dimension of the conduit may be about 0.5-1.0 mm greater than that of the guidewire/ stylet. Alternatively, the cross sectional dimension of the conduit may be about 1.0-2.0 mm greater than that of the guidewire/stylet.

FIG. 39H shows an embodiment of the vascular catheter navigation device which includes multiple securing style conduits 3902. Multiple securing style conduits may allow for better longitudinal fixation between the guidewire/stylet and the catheter near the distal end of each. Note in this example, length 3905 is essentially zero, which is the case when sensor 2516 is essentially at the distal tip of the catheter. "Essentially zero" may mean plus or minus 1 mm, or "Essentially zero" may mean plus or minus 2 mm, or "Essentially zero" may mean plus or minus 3 mm. This may be the case with any of the embodiments disclosed herein.

FIG. 39I shows an embodiment of the vascular catheter navigation device where securing style conduit is a helix. The helix stabilizes and centers the guidewire/stylet within the infusion lumen of the catheter, while allowing fluid to flow past the conduit. The helix is preferably open on the ends to allow fluid to flow therethrough.

FIG. 39J shows an embodiment of the vascular catheter navigation device where securing style conduit 3902 is one or more metal wires or filaments, which secure the stylet with respect to the catheter lumen via outward mechanical force. The filaments may run the length of the guidewire/ stylet and may be expanded/retracted using a mechanism at the proximal end of the guidewire/stylet. The filaments may be single strands of metal, or may be a cage, or spiral etc.

Markings or any other mechanism may be used to align the conduit with the distal end of the catheter for catheter navigation. For example, a moveable marker may exist on the proximal end of the guidewire/stylet so that the distal tip of the vascular catheter (possibly after having been cut to length) can be aligned with the conduit outside of the body, the moveable marker moved so that it lines up with the proximal end of the vascular catheter, and then the catheter may be inserted into the body. Other mechanisms include valves, such as a tuohy-borst valve, or clamps, torque device, etc. The length of the conduit may be long enough so that exact alignment of the distal tips of the catheter and the conduit is not necessary. For example, the vascular catheter may move about 0-2 mm with respect to the guidewire/stylet during the placement procedure. Alternatively, the vascular catheter may move about 0-4 mm with respect to the guidewire/stylet during the placement procedure. The conduit may be longer than this, for example, about 2-12 mm, to accommodate for these changes in alignment and ensure that the conduit spans the distal tip of the catheter.

Some embodiments of the vascular catheter navigation device may restrict the conduit from exiting the distal end of the vascular catheter. Some embodiments may allow the conduit to exit the distal end of the vascular catheter. The proximal end of the conduit may be tapered to a smaller cross sectional area proximally so that the conduit can be pulled back into the catheter without catching.

FIGS. 40A-C show some different configurations of vascular catheter lumens and variations of embodiments of the vascular catheter navigation device which work with them. Vascular catheters may have one, two, three, four, five or more lumens. FIG. 40A shows some example configurations of 2 lumen vascular catheters. These configurations include infusion lumen 2506 and auxiliary lumen 4002. The auxiliary lumen may be an additional infusion lumen, a sampling lumen, a pressure lumen, a guidewire/stylet lumen, a tools lumen, or a lumen used for any other purpose. Shown here are guidewire/stylet 2504, conduit 2502, flow passage(s) 2518 and vascular catheter 2508. Some of the various components of the vascular catheter navigation device, including the stylet, conduit, and flow passage(s) may have different cross sectional shapes to accommodate the different shape vascular catheter lumens. Some examples are shown here, but others are envisioned. The shape of the conduit may be preformed, for example in the form of a polymer conduit, or may take on the shape of the lumen, for example via an inflatable or conformable conduit, for example as shown in FIGS. 27, 28, 29A-C, 30, and 36A-C.

FIG. 40B shows some examples of configurations of 3 lumen vascular catheters. FIG. 40C shows an example of a configuration of a 4 lumen vascular catheter.

Note that although embodiments disclosed herein show the vascular catheter navigation device in an infusion lumen of a vascular catheter, it is also possible that the vascular catheter navigation device may be used in any lumen of a vascular catheter, for example a sampling lumen. It is also possible that more than one vascular catheter navigation devices may be used at once in more than one lumen.

Figures 41D, 41E, 41F:
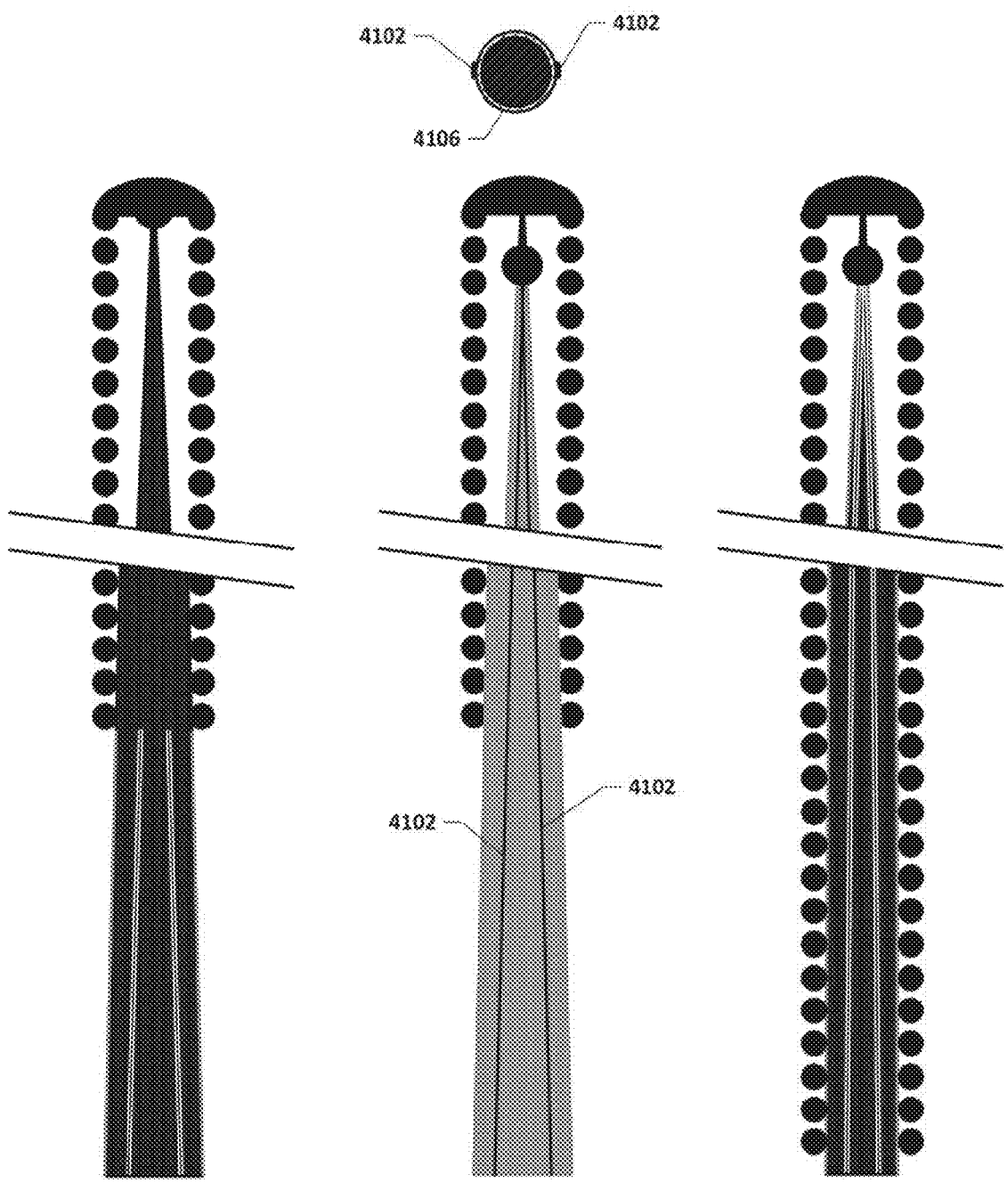

FIGS. 41A-F show various embodiments of a guidewire/stylet component of the vascular catheter navigation device. FIG. 41A shows guidewire/stylet 2504, including core 2510, coil 2512, endcap 2514 and temperature sensor 2516. Also shown here are temperature sensor lead wires 4102, temperature sensor lead wire insulation layer 4104, stiffener 4108 and core enclosure 4106. The temperature sensor lead wires connect the temperature sensor on the distal end of the device to the controller on the proximal end of the device. There may be one, two or more lead wires. For example, a thermocouple will usually have 2 lead wires. Some thermocouples, however, may have 3 lead wires if one of the lead wires is a ground wire. The lead wires are preferably made out of metal. The lead wires may be insulated with insulation layer 4104 which surrounds each lead wire. In some embodiments, only one of the lead wires is insulated. The insulation material may be made out of polymer such as polyethylene or PTFE or polyimide or other suitable material and may or may not be heat shrinkable. The stiffener may be made out of metal and may be tapered to a smaller cross sectional dimension at the distal tip, or the stiffener may have a consistent cross section over its length. The stiffener may be round in cross sectional area or may be any other shape. The stiffener may alternatively be a polymer. The lead wire(s) may serve as the stiffener in which case, and additional stiffener will not be present.

The core, which includes the lead wire(s) and an additional stiffener, if present, may be encapsulated with enclosure 4106. Enclosure 4106 may be a tube made out of polymer, such as polyimide, polyethylene, PTFE etc., or metal or other suitable material. The enclosure may alternatively be a dip or spray coating. The enclosure may be a heat shrinkable tubing.

FIG. 41A shows a guidewire/stylet where lead wires travel to the distal end of the stylet where temperature sensor 2516 exists separately from endcap 2514 and proximally to the endcap. FIG. 41B shows an embodiment where the endcap and the temperature sensor are combined. FIG. 41C shows an embodiment where the temperature sensor is distal to the endcap.

FIG. 41D shows an embodiment of the stylet/guidewire where the coil serves as the lead wire(s). In this embodiment, the lead wire(s) exit the core and are incorporated into the coil proximal to the temperature sensor.

FIG. 41E shows an embodiment where lead(s) 4102 are made out of conductive ink. In this embodiment, the lead(s) may be on the outside of enclosure 4106. The ink may be deposited onto the enclosure. The conductive ink lead(s) may be sandwiched between two enclosures. Note that conductive ink may be used for any of the sensors, including thermocouples, ECG, temperature sensors, etc., and may be printed on the stylet and/or catheter and/or conduit.

FIG. 41F shows an embodiment of the stylet/guidewire where the coil exists over the entire length, or substantially the entire length, of the stylet/guidewire.

FIG. 42A shows an embodiment of the stylet/guidewire where lead(s) 4102 also serve as stiffener(s). The lead(s) may be encapsulated in enclosure 4106 and connect to sensor 2516. Additional stiffness may be added to this embodiment by using thicker leads, thicker/stiffer enclosure, for example, metal braid or coil or filament reinforced polyimide or polymer tubing etc. Alternatively, the gap between the enclosure and the leads may be filled with epoxy or adhesive. The leads may be welded or bonded to each other or to the enclosure. The enclosure may be co-extruded with one or more of the insulation layers of the lead(s), as shown in FIG. 42B. Thermoset polymers and/or metals may be used in the enclosure, insulation and/or leads. Each lead may include an insulation layer or only one lead may have an insulation layer or neither lead may include an insulation layer, for example in the embodiments where adhesive or epoxy is used to stiffen the stylet. In such embodiment, the lead diameter, cross-section design, and material may be designed to match desired stiffness of the stiffener. One or more of the leads may be spiral, coiled, or braided to achieve desired stiffener mechanical properties.

FIG. 42C shows the embodiment shown in FIG. 42A with the addition of a coil.

Any of the guidewires/styli disclosed herein may be used with any of the embodiments disclosed herein including any of the conduit embodiments.

Some embodiments disclosed herein may be used to determine fluid levels, or hydration level, of a patient. Fluid levels are particularly important when a patient has congestive heart challenges. A lower fluid level may result in lower amplitude pulses in the blood flow, where a higher fluid level may result in greater amplitude blood flow pulses. Other flow patterns may be different between a hydrated patient and a less hydrated patient. These flow patterns can be detected using embodiments disclosed herein. Hydration level can be monitored in a patient over time or compared among patients.

Where "sensor" or "temperature sensor" is used herein, other types of sensors may be used, including any measurable parameter including temperature, opacity, light reflectivity, sound reflectivity, density, viscosity, ability to absorb light, ability to absorb sound, pressure etc.

Figure 43:
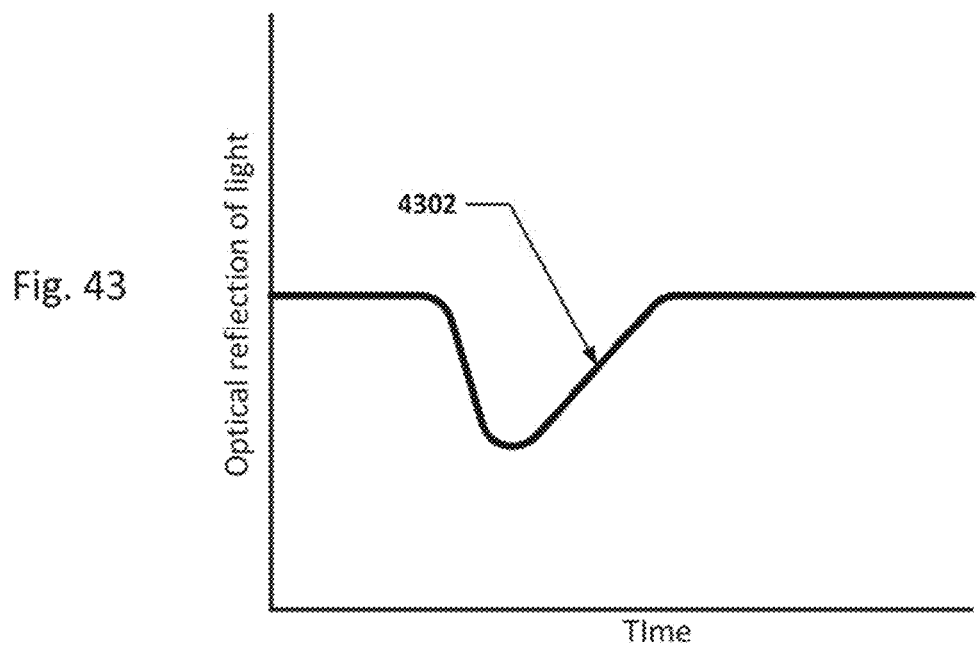
FIG. 43 shows an embodiment of the vascular catheter navigation device which uses optical reflection.

FIG. 43 shows that an optical signal can provide information on direction of blood flow and other blood flow parameters. In this embodiment, the medium is light and the parameter measured is light intensity and/or reflected light. Curve 4302 represents a measurement of reflected light over time in a blood vessel where blood flow is toward the device.

Figure 44:
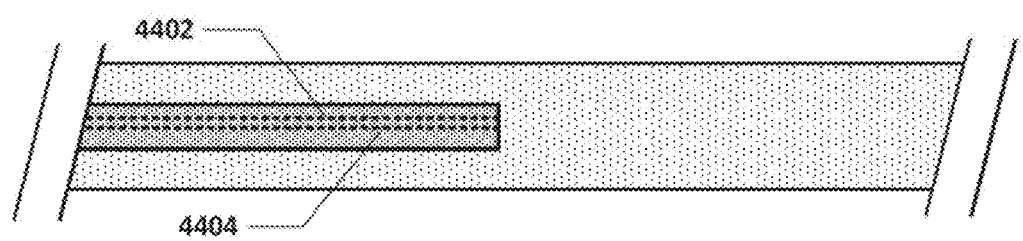
FIG. 44 shows an embodiment of the vascular catheter navigation device which uses optical reflection.

FIG. 44 shows an embodiment of a device which uses optical sensors. Fiber optic cables 4402 and 4404 can be used for transmission and detection of light. One cable may be used to introduce the medium (light) and the other cable serves as a sensor for a parameter of the medium (light intensity/wavelength). A detector and emitter combination can be used or an optical detector can be used without an emitter, requiring only one fiber. In some embodiments, light at particular wavelengths may be used. For example, red light of approximately 620 nm to 750 nm may be emitted, which is reflected more by red blood cells than by saline, or saline diluted blood. Thus a response can indicate a flow direction or characteristic. This same embodiment can be enabled more broadly with other types of visible light of about 350 nm-800 nm and near infrared light between about 400 and 1400 nm. This embodiment can be achieved with detector and/or emitters that are located at the point of measurement and potentially used in combination with a flex circuit. The optical measuring embodiment can also be used with the use of fiber optics (plastic, glass or other,) or light pipes where the actual detector and emitter are located in the controller and the light pipe or fiber optic communicates information collected at or near the catheter tip with the controller located outside the patient. This can be performed with fiber optic lines which are about 0.1 mm to about 0.5 mm in diameter or about 0.5 mm to about 4 mm in diameter. The fiber optic cable(s) may have an insulated coating. In some embodiments, a single optical fiber may be used to measure temperature.

Figure 45:
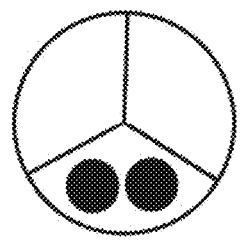
FIGS. 45 and 46 show temperature profiles in the superior vena cava and in the heart.
Figure 46:
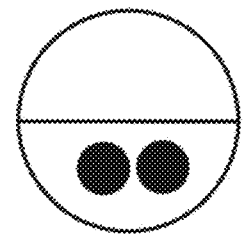

FIGS. 45 and 46 show a triple lumen device and a double lumen device respectively, with 2 fiber optic cables.

Figure 47:
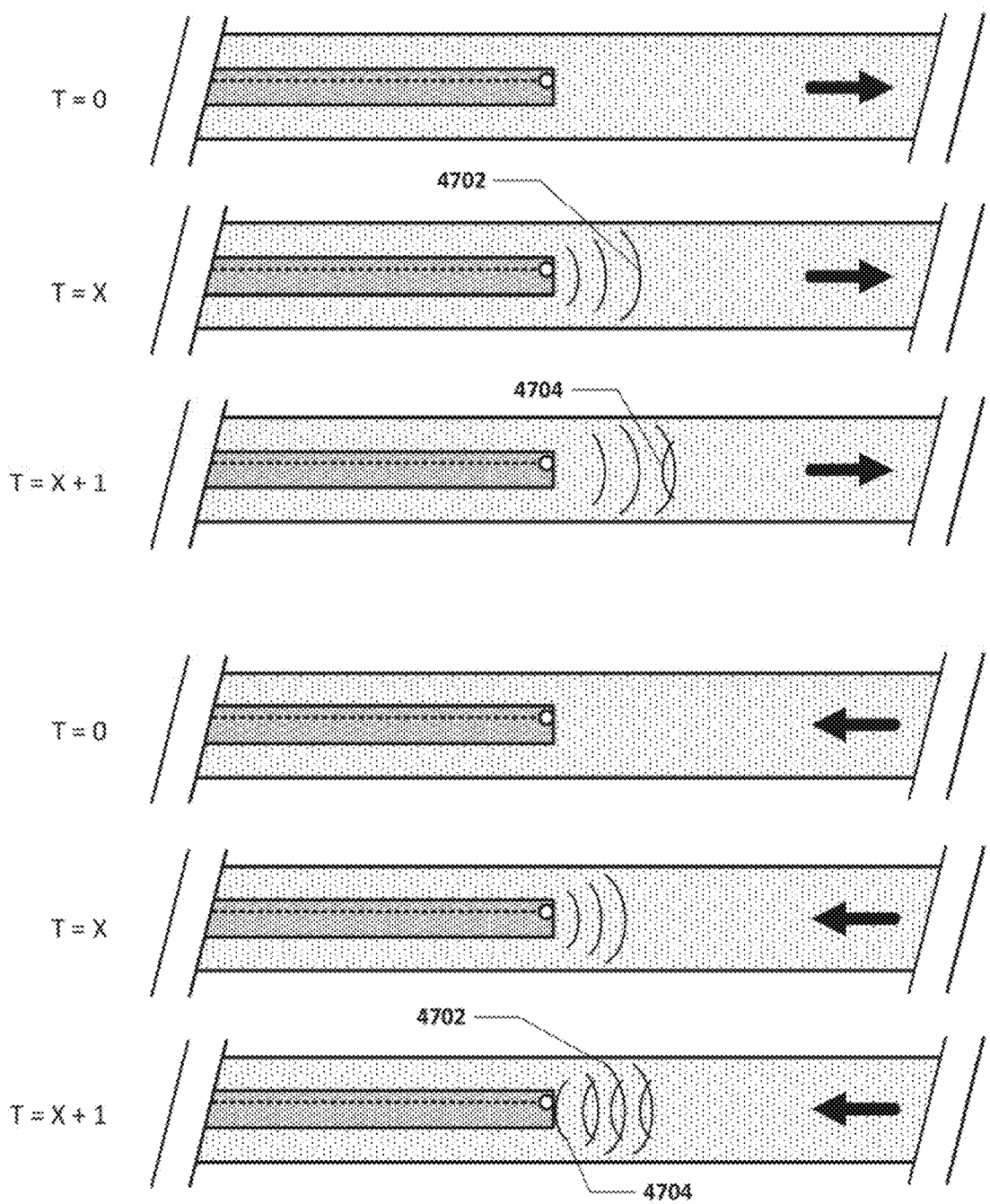
FIG. 47 shows an embodiment which uses sonar and sound waves to detect blood direction.

FIG. 47 shows an embodiment which uses sonar and/or sound waves to detect blood direction. In this embodiment, the medium introduced is sound and the parameter measured by sensors is reflected sound intensity and/or wavelengths. Sound is introduced via the device resulting in sound waves 4702 transmitted into the blood vessel. Some sound waves will be reflected back as reflected sound waves 4704 and can be measured by a sensor, such as a microphone, on the device.

Figure 48:
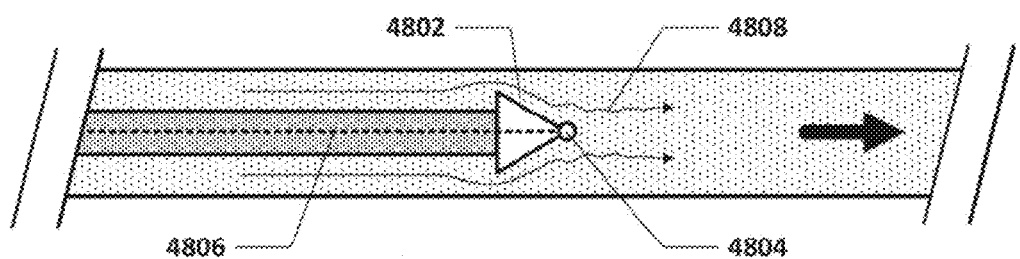
FIGS. 48 and 49 show an embodiment which uses one or more pressure sensors, with the aid of a turbulence inducer, to determine directionality of flow.
Figure 49:
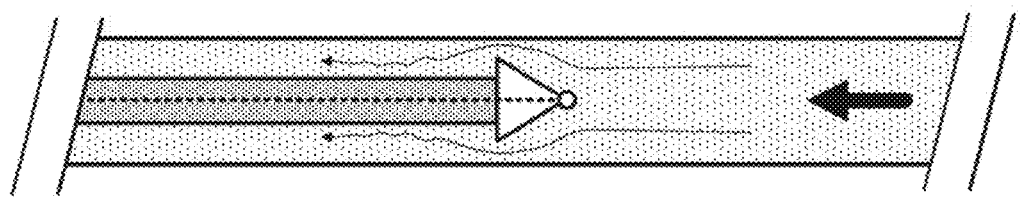

FIGS. 48 and 49 show an embodiment which uses one or more pressure sensors, with the aid of a turbulence inducer, to determine directionality of flow. A single pressure sensor 4804 or multiple pressure sensors can be used to detect the direction of flow with respect to the catheter or pressure sensor. This embodiment can include mechanism 4802 that induce turbulent flow 4808 to create different pressures at the reading location depending on if the flow disruption feature is upstream or downstream of the pressure sensor. Pressure data measured by pressure sensor 4804 is communicated to the controller (not shown) via connector 4806. This turbulence inducer can be included on the stylet and deployed much like an umbrella and then retracted. This turbulence inducer can be deployed and pushed through the vasculature as the device approaches the heart, or the turbulence inducer could be deployed at specific times when the location of the device needs to be determined. This could either be at a predetermined intervals, for example, about every 3 seconds (or ranging from 1 second to 5 seconds) or simply deployed whenever the operator would like to take a measurement. Alternatively, the turbulence inducer may be small enough so that it may be permanently deployed.

Figure 50:
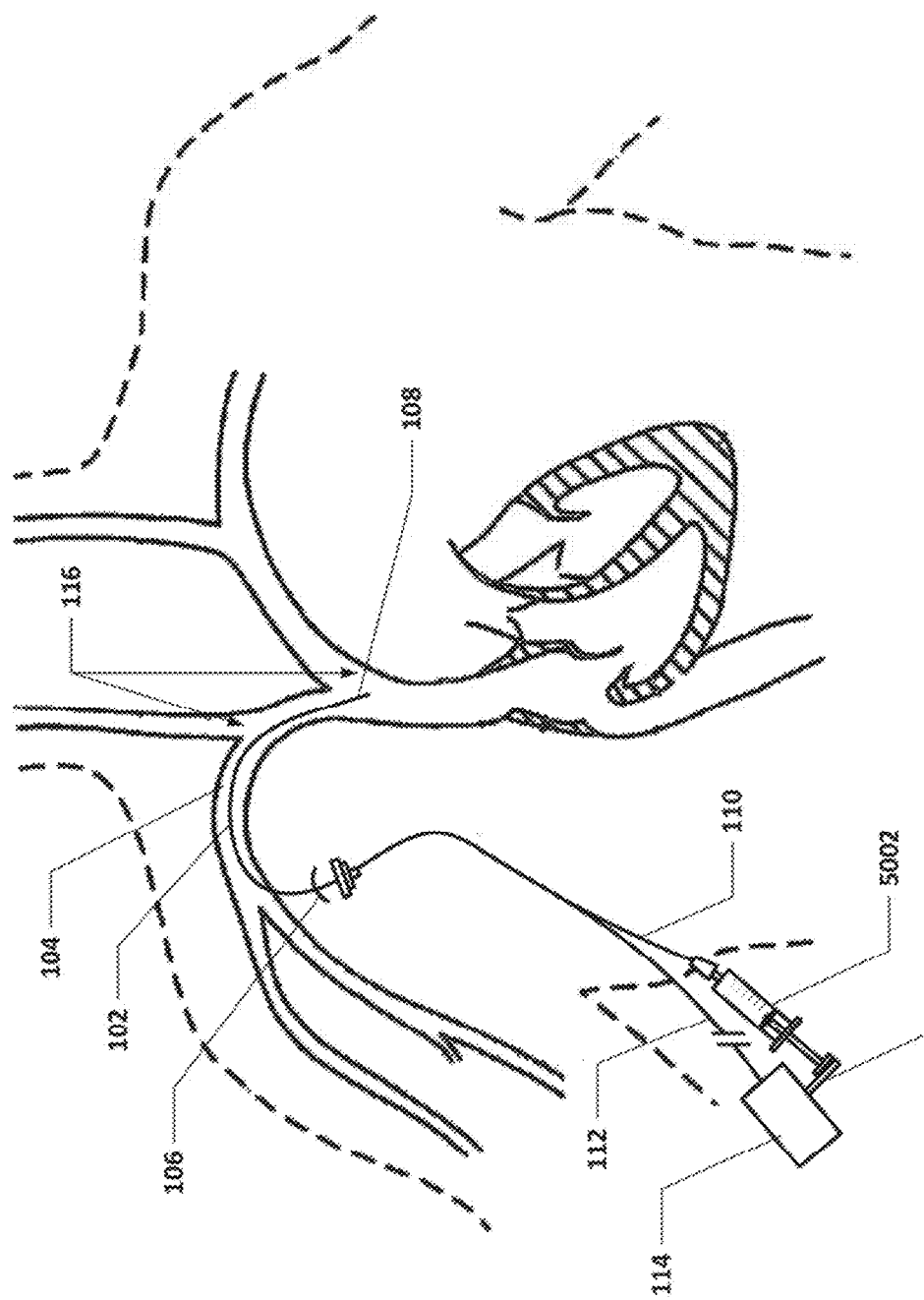
FIG. 50 shows an embodiment which includes a controller and a medium introduction mechanism.

FIG. 50 shows an embodiment which includes controller 114 and a medium introduction mechanism 5002 controlled by the controller via lever or mechanism 5004. The medium introduction mechanism may be a syringe containing saline or other fluid and mechanism 5004 may be a lever controlled by a motor within the controller. Alternatively, the controller may be remote from the medium introduction mechanism. The media introduction mechanism may alternatively be manually driven. The controller may be at the patient's bedside or remote. The controller may provide real time feedback if there are any changes of safety issues. It may be used standard PICC, subclavian, and intra jugular catheters, central catheters, regardless of brand.

Controller

The controller may control delivery of the medium and detection of the medium parameter in the blood flow. In addition the controller will receive information from the one or more sensors and interpret the information to assess the location, relative location, and/or hazard zones within the vasculature. The sensor signals are communicated, via a wire, fiber optic cable, or other means, back to the controller where the signal(s) are analyzed based on the measured parameter, parameter profile, parameter of more than one sensor, or change in parameter over time and/or distance. For example, the controller can determine whether the distal end of the vascular catheter navigation device is in an artery instead of a vein, based on magnitude and direction of blood flow, and/or other flow parameters, near the vascular catheter navigation device. For example, if the controller determines that the distal end of the vascular catheter navigation device is in an artery instead of a vein, a specific identifying signal may sound, including an audible, visual signal etc., instructing the user to remove the vascular catheter navigation device, and any other device, such as sheaths, catheters etc., and apply pressure to the blood vessel. For example, instructions for advancing, retreating, redirecting, stopping or removing, the vascular catheter navigation device may be displayed by the controller on a screen connected to the controller either. The connection may be wired or wireless and the screen may be local or remote. The signal from the controller may be transmitted over Bluetooth, or other wireless protocol, to a computer such as a laptop, tablet, phone, watch, or other peripheral device.

The controller may control introduction of medium, including injection of a temperature controlled solution, such as saline, introduction of sound, introduction of light etc. Temperature controlled may mean a temperature which is different than body temperature.

The controller may also integrate with other system, such as electronic medical systems, electronic health systems etc. The integration may be wired or wireless and may be local or remote. The integration may be via "EMR sniffers".

Injection Mechanism and Fluid Properties

The infusion drip, bolus, droplet, stream, etc., used to detect catheter location may have specific parameters. The infusion may be a drip or it may be a stream. The preferred intermittent volume size (drip, drop, bolus, intermittent stream) is between about 0.5 cc to about 3 cc, but can range between about 0.1 cc and about 10 cc. Alternatively the volume may range from about 0.5 cc to about 1 cc. Alternatively the volume may range from about 0.5 cc to about 2 cc.

The preferred drip interval may be between about every 0.5 second to about every 4 seconds to a broader range of about every 0.25 seconds to about every 10 seconds. Where the infusion is a continuous stream, the preferred flow rate is about 4 cc/minute but may range from about 0.25 cc/minute to about 15 cc/minute or from about 0.1 cc/minute to about 30 cc/minute or from about 0.1 cc/minute to about 60 cc/minute.

The pressure applied to the injection mechanism (syringe, for example) for injection may be around 3 psi but may range from about 1 psi to about 5 psi, or the range may be from about 0.1 psi to around 200 psi.

The fluid temperature in a thermo-dilution sensing solution is optimally around 22.5 C but may be about 20 C to about 25 C or from about 1 C to about 36 C. Alternatively the fluid may be greater than body temperature, optimally about 40 C but ranging from about 39 C to 42 C or about 37 C to about 45 C.

The controller may control an injection device, or volumetric displacing device, such as a syringe, so that the injection device introduces a controlled volume and/or rate of fluid into the catheter or stylet/guidewire. The fixed volume and/or rate of fluid may be at a controlled temperature, either above or below that of blood (approximately 37 degrees Celsius), or at a known temperature which is measured. The injection device may inject a controlled volume and/or rate of fluid at predetermined intervals, or other intervals, or continuously. The controlled volume and/or rate of fluid may remain the same throughout a procedure, or the volume and/or rate may change depending on the patient, the location of the catheter/system within the vasculature, etc. For example, the volume and/or rate of fluid injected may increase as the tip of the catheter gets closer to the heart. The volume and/or rate may be different for different sized vascular catheters or different sized lumens of vascular catheters, for example in catheters with multiple lumens.

The volume and/or rate of fluid injected may be controlled by a lead screw, cam, linear actuator motor etc. The force of the injection requirements may also be controlled and/or monitored. For example, if an unusually high force is required to inject the fluid, an alert may tell the user that a possible catheter blockage situation exists, including a catheter kink, a blood clot, the catheter tip up against a vessel wall, or within a small vessel, or other catheter patency situation. Higher or lower force injections may be used in different areas of the anatomy, or to confirm location within the anatomy. For example, a higher forced injection of a smaller volume and/or rate may provide different temperature curve information than a lower force, higher volume and/or rate injection. Small volume injections at a higher frequency may provide different information than larger volume injections at a lower frequency, etc.

The fluid injector may also be configured to withdraw fluid through the catheter/stylet/guidewire to determine injection lumen/tip patency. The controller may assess force to withdraw fluid to determine that fluid is flowing freely through the catheter/stylet/guidewire. If fluid is not flowing freely, a patency alert may alert the user. Alternatively the controller may have a sensor which senses the existence of blood in the system when the injector withdraws fluid through the catheter/stylet/guidewire. This may be done optically or otherwise.

Figure 51:
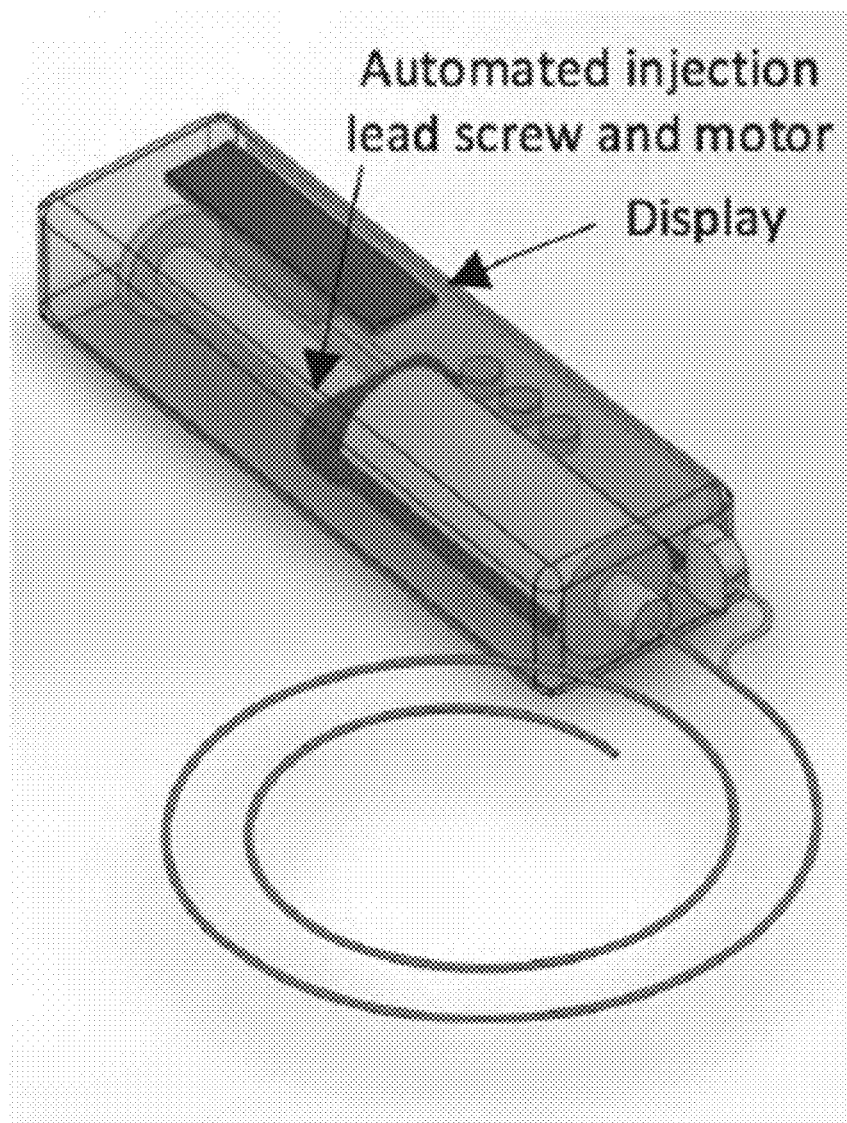
FIG. 51 shows an embodiment which includes an automated injection system for the cartridge/syringe/reservoir which may be a motor driving lead screw.

An embodiment of the injection mechanism is shown in FIG. 51. This embodiment may include an automated injection system for the cartridge/syringe/reservoir which may be a motor driving lead screw. The controller controls the infusion delivery parameters, including pressure, volume, frequency, rate, etc. The controller may also control the GUI. The buttons, shown in FIG. 51 may turn the device on and off, purge the catheter of air prior to insertion, and/or may stop operation of the device in case of a sensed problem situation. The unit may be fully disposable, partially disposable or non-disposable, and may reside in the sterile field or the unsterile field during the procedure.

The system may come packaged with a prefilled injection device, or a fillable injection device. Saline may be used as the fluid. Contrast medium may be used (which is a higher viscosity than saline). Fluids of differing viscosity may be used, or fluids may be mixed (such as contrast medium and saline) to achieve a desired viscosity or other desired properties. Fluids of different surface tension, different specific heat capacity, different acidity or other different attributes may be used. Fluids with properties that differ from those of blood will provide different temperature curves and therefor provide different information regarding the location of the catheter/guidewire/stylet tip in the vasculature. Some fluids may be soluble in blood and others less soluble. Since the injection fluid is injected into the blood stream, the fluid used will preferably be biocompatible.

Additives may be added to the injection fluid for different results. For example, salts, such as NaCl may be added. Different salts or other additives may improve an ECG signal in embodiments that include an ECG electrode. A different fluid (liquid or gas) may be introduced with the primary fluid to modify the fluid properties. For example, a biocompatible liquid or gas may be "bubbled" into saline.

A user interface controlled by the controller may include a display, alerts (auditory, visible, lights, vibrations etc.) and other information. The user interface may include a display of the anatomy with a virtual reality indicator of the location of the catheter/guidewire/stylet tip within the anatomy. For example, the display may be an image of the human vascular system, and a moving indicator, such as a light, may show where within the anatomy the catheter/guidewire/stylet tip is. The display may be actual size, and possibly even projected upon the patient, or it may be a smaller or larger size, for example, displayed on the controller, a tablet, or projected up on the wall. The controller and/or display may include a computer, laptop, tablet, mobile phone, virtual reality/augmented reality glasses, etc.

The system may be fully disposable. A fully disposable system primary package includes: syringe, syringe pump, the syringe filled with the fluid of choice, a controller, a user interface which can exist as any combination of display, alert, and lights, catheter, stylet/guidewire, and introduction mechanism. All of these elements may be fully disposable. By doing so, the chance of infection will be reduced.

Another embodiment includes all of the items listed above where the display is non-disposable. The display may be within the non-sterile field and communicate via cable or a wireless communications protocol such as Bluetooth. Alternatively, the display may be within the sterile field using a wired or wireless connection. Additionally/alternatively, the display may be projected on glasses—either virtual reality or augmented reality glasses. The glasses may be within the sterile or non-sterile field. Additionally, a projector may project the display on a surface of choice and the projector may be in sterile or non-sterile field.

Another embodiment consists of two subsystems. The disposable elements may include catheter, stylet/guidewire, and a fluid filled volume displacing device, such as a syringe. The non-disposable elements may include a controller in a housing, mechanics/motors to depress the lead screw on the syringe/cartridge, display, audio, and visual elements, as well as user interaction buttons, etc.

Any of the catheter/stylet/guidewire placement and/or patency techniques disclosed herein may be used while placing the device in the vasculature, as well as after placement, to determine that the device has not significantly strayed from its placement location.

Any of the embodiments disclosed herein may be used with any type of central vascular catheter including Central Venus lines, Clavicle lines, midline, etc. In addition, any of the embodiments disclosed herein may be used with peripheral vascular catheters, dialysis catheters, and cardiac catheters including catheters used for: coronary arteries, patent foramen ovale, atrial septal defect, etc. Any of the embodiments disclosed herein may be used with any type of urinary catheters. Similar technology may be used in underwater navigation, mining, oil and gas exportation, utility fabrication or repair, transportation infrastructure fabrication and repair, etc.

Other technologies may also be used in conjunction with the sensor readings from the vascular catheter. For example ECG readings, ultrasound readings, Doppler readings, x-ray readings, inductive current technology, pressure readings, etc. Some, all or no readings may be augmented via a turbulence inducer. These, and other, other types of readings may be used in conjunction with the sensor readings by the controller to determine the location of the vascular catheter navigation device distal tip. Specific modalities may be better at identifying specific vascular landmarks or conditions.

For example, any of the conductive components of the vascular navigation device may be used as an ECG lead. Another ECG lead may be placed on the patient's skin. For example, the guidewire stylet stiffener, coil, enclosure, thermocouple leads, sensor leads, thermocouple, endcap, conduit, etc. may be used as an ECG lead. Alternatively, a separate ECG lead may be added to the system.

Embodiments of the vascular navigation device may include the ability to measure cardiac output. The temperature vs. time curve may be analyzed by the controller to determine cardiac output in addition to vascular location, either simultaneously, or at separate times. Cardiac output may also be used to help establish the location of the vascular navigation device within the vasculature.

Several embodiments have been disclosed herein. It will be understood that any of the features of any of the embodiments may be combined with any embodiment.

Some embodiments of the vascular access or vascular navigation device may be used in other applications. For example, the controller of the device may be equipped with logic to navigate, identify, and assess the health of various vascular or other anatomies. For example, some embodiments may be configured to identify the location of valves within the peripheral vascular (for example, venous) system. Valve location may be identified based on the flow characteristics near and within a valve. Valve health may be assessed based on flow characteristics near and within a valve. Valve function may be assessed based on flow characteristics near and within a valve. Valve closure may be assessed based on flow characteristics near and within a valve. Vascular flow characteristics may be used by the system to navigate near to, within, and/or past valves. Some embodiments of the vascular navigation device may be used in conjunction with treatment procedures. For example, the system may be used to aid in placement of valve prosthetics, valve repair etc. The system may be used to assess the success of such procedures, based on flow characteristics, placement location etc. The system may also be used to navigate to vessel stenting locations, and to assess the function of a vessel before and after a procedure. The system may be used to assess the function and/or location and/or health of a prosthetic (stent, valve etc.) before and after its placement.

In some embodiments, the system may be used to diagnose a stenosis, blockage, narrowings or disease of a blood vessel based on flow characteristics. The system may be used to classify a stenosis, blockage, narrowings or disease of a blood vessel based on flow characteristics. The system may be used to identify the location and quantity of spinal fluid leak.

In some embodiments of the system, the vascular system is accessed peripherally, via a leg, arm, groin, etc.

Some embodiments of the system may be used to diagnose other diseases or health based on flow characteristics of vessels or other organs (such as the bladder, lungs, etc.)

Some embodiments of the system may be used to assess health of, and navigate through, other vessels such as those in the brain. For example, the system may be used to identify, navigate to and assess the health of, aneurysms, blockages, narrowings, stenosis with the brain and elsewhere in the body.

Embodiments of the system may be used for any interventional radiology procedure including Angiography, Arteriovenous Malformations (AVM), Balloon Angioplasty, Biliary Drainage and Stenting, Bleeding Internally, Central Venous Access, Chemoembolization, Embolization, Gastrostomy Tube, Hemodialysis Access Maintenance, High Blood Pressure, Infection and Abscess Drainage, Needle Biopsy, Radiofrequency Ablation, Stent, Stent Graft, Thrombolysis, TIPS (Transjugular Intrahepatic Portosystemic Shunt), Urinary Tract Obstruction, Uterine Artery Embolization, Uterine Fibroid Embolization, Varicocele Embolization, Varicose Vein Treatment, Vena Cava Filter, Vertebroplasty, Deep Vein Thrombosis, etc.

Some embodiments of the system may be used to identify blood flow direction, speed, flow characteristics, etc. This may be useful not only for navigation of the venous system, but also in assessing venous or arterial flow conditions that are useful for identifying heart disease, chronic venous disorder, venous outflow obstructions, etc.

Some embodiments of the system may be used to identify the change in flow characteristics of the blood as it responds to drugs such blood thinners (heparin, etc.) acutely or over time. For example, blood thinness, viscosity, or other properties may be assessed based on the flow characteristics.

Some embodiments of the multi sensor technology may also be included in a permanent implant within the body rather than used as a temporary device. It may be used to measure the performance or health of the cardiovascular system over time, measure post intervention performance over time, etc. This type of intervention may be surgical only, such as when used in a bypass procedure, and may also include monitoring the results and/or performance, and/or success of interventions such as mechanical valves, stents, balloons, etc. It may also be used for the assessment of the need for interventions.

In another embodiment, in addition to or instead of measuring temperature of a fluid bolus or stream that is injected, the system may measure the electrical conductivity of a bolus or stream of fluid. As a stream or bolus of fluid fluctuates with various flow conditions and directions, variation in electrical conductivity can be detected. Additionally, fluid may be injected to optimize the electrical conductivity. For example, fluid containing one or more salts may be used to make the fluid more electrically conductive.

This technology may also be used outside of the body on the surface of the skin in proximity to one or more veins. This may be done on the skin or just under the skin, across the skin or within the skin. For example, the temperature sensors can be placed in several locations on top of the skin or vein. A heating or cooling event may be administered intravascularly to detect blockages, flow, or navigation requirements. Conversely, the heating and or cooling event may happen externally to the skin while the system senses the temperature intravascularly. Alternatively, pressure, or electrical conductivity may be used. Some embodiments may also detect flow characteristics, diagnose venous or arterial disease, challenges, and obstructions, in either acute or chronic events. Embodiments of the device on the surface of the body or vein may be a temporary assessment tool, or may be a more permanently worn biosensor such as a watch, ring, wristband, necklace, earing, contact lens, etc.

Example of Data Processing System

Figure 52:
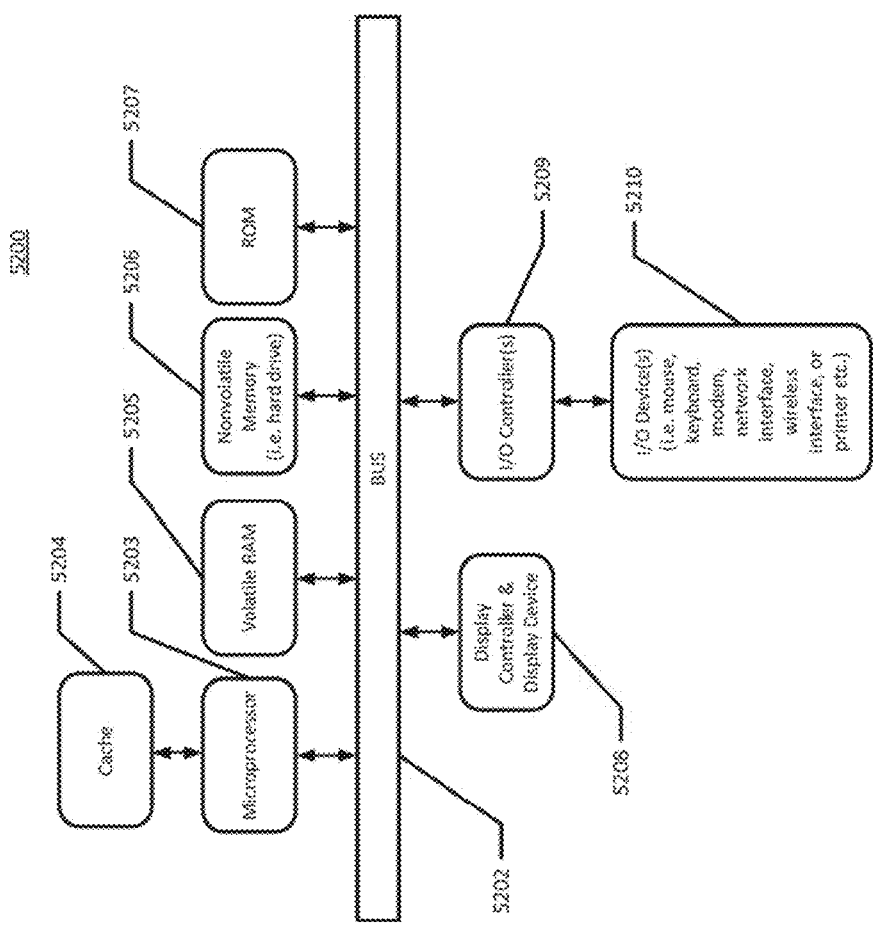
FIG. 52 is a block diagram of a data processing system, which may be used with any embodiments of the invention.

FIG. 52 is a block diagram of a data processing system, which may be used with any embodiment of the invention. For example, the system 5200 may be used as part of the controller. Note that while FIG. 52 illustrates various components of a computer system, it is not intended to represent any particular architecture or manner of interconnecting the components; as such details are not germane to the present invention. It will also be appreciated that network computers, handheld computers, mobile devices, tablets, cell phones and other data processing systems which have fewer components or perhaps more components may also be used with the present invention.

As shown in FIG. 52, the computer system 5200, which is a form of a data processing system, includes a bus or interconnect 5202 which is coupled to one or more microprocessors 5203 and a ROM 5207, a volatile RAM 5205, and a non-volatile memory 5206. The microprocessor 5203 is coupled to cache memory 5204. The bus 5202 interconnects these various components together and also interconnects these components 5203, 5207, 5205, and 5206 to a display controller and display device 5208, as well as to input/output (I/O) devices 5210, which may be mice, keyboards, modems, network interfaces, printers, and other devices which are well-known in the art.

Typically, the input/output devices 5210 are coupled to the system through input/output controllers 5209. The volatile RAM 5205 is typically implemented as dynamic RAM (DRAM) which requires power continuously in order to refresh or maintain the data in the memory. The non-volatile memory 5206 is typically a magnetic hard drive, a magnetic optical drive, an optical drive, or a DVD RAM or other type of memory system which maintains data even after power is removed from the system. Typically, the non-volatile memory will also be a random access memory, although this is not required.

While FIG. 52 shows that the non-volatile memory is a local device coupled directly to the rest of the components in the data processing system, the present invention may utilize a non-volatile memory which is remote from the system; such as, a network storage device which is coupled to the data processing system through a network interface such as a modem or Ethernet interface. The bus 5202 may include one or more buses connected to each other through various bridges, controllers, and/or adapters, as is well-known in the art. In one embodiment, the I/O controller 5209 includes a USB (Universal Serial Bus) adapter for controlling USB peripherals. Alternatively, I/O controller 5209 may include IEEE-1394 adapter, also known as FireWire adapter, for controlling FireWire devices, SPI (serial peripheral interface), I2C (inter-integrated circuit) or UART (universal asynchronous receiver/transmitter), or any other suitable technology. Wireless communication protocols may include Wi-Fi, Bluetooth, ZigBee, near-field, cellular and other protocols.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques shown in the Figures can be implemented using code and data stored and executed on one or more electronic devices. Such electronic devices store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals—such as carrier waves, infrared signals, digital signals).

The processes or methods depicted in the preceding Figs may be performed by processing logic that comprises hardware (e.g. circuitry, dedicated logic, etc.), firmware, software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

What is claimed is:

1. A location detection system, comprising:
    an elongate body;
    a conduit defining one or more flow passages, where each of the one or more flow passages has a distal end and where the conduit is configured to secure a position of the elongate body relative to the conduit;
    a sensor positioned at or in proximity to the distal end of the elongate body, wherein the conduit maintains a fixed distance between the sensor and the one or more flow passage distal ends, and wherein the sensor is configured to measure at least one parameter of a fluid after the fluid is emitted from the one or more flow passage distal ends; and
    a controller in communication with the sensor, wherein the controller is configured to determine a time-derived function of the at least one parameter of the fluid and is further configured to obtain a position of the sensor within a body of a subject, and wherein the time-derived function is based upon a degree of turbulence of the fluid after emitted from the one or more flow passages.

2. A method of determining a location within a body of a subject, comprising:
    positioning an elongate body within a lumen of a catheter;
    positioning the catheter within the body of the subject;
    introducing a fluid through the lumen and one or more flow passages of a conduit into the body;
    measuring via a sensor at least one parameter of the fluid after introduction within the body of the subject, wherein the sensor is positioned at or in proximity to a distal end of the elongate body such that the sensor is maintained at a fixed distance relative to a fluid exit port of the catheter or conduit;
determining a time-derived function of the at least one parameter of the fluid; and
determining a position of the sensor within the body of the subject based upon the time-derived function.

3. The method of claim 2 wherein positioning the catheter comprises advancing the catheter intravascularly within the body of the subject.

4. The method of claim 2 wherein measuring via a sensor at least one parameter comprises measuring a temperature.

5. The method of claim 2 wherein introducing a fluid further comprises passing the fluid through the one or more flow passages of the conduit positioned at or in proximity to the distal end of the elongate body.

6. The method of claim 2 wherein the elongate body is attached to the conduit.

7. The method of claim 2 wherein the elongate body is positioned to extend longitudinally relative to the lumen.

8. The method of claim 2 further comprising measuring an electrical signal within the body via an ECG electrode incorporated into the elongate body.

9. The method of claim 2 wherein measuring via a sensor further comprises transmitting sensor data between the sensor and a controller.

10. The method of claim 9 further comprising transmitting temperature data between the sensor and the controller.

11. The system of claim 2 wherein determining a time-derived function comprises determining a degree of turbulence of the fluid after being emitted from the fluid exit port.

12. The method of claim 2 wherein determining a time-derived function comprises determining a difference in temperature from baseline to obtain the position of the sensor within the body.

13. A location detection system for use within a catheter lumen, comprising:
an elongate body;
a sensor positioned at or in proximity to the distal end of the elongate body, wherein the sensor is configured to measure at least one parameter of a fluid after the fluid is emitted from the catheter lumen; and
a controller in communication with the sensor, wherein the controller is configured to determine a time-derived function of the at least one parameter of the fluid and is further configured to obtain a position of the sensor within a body of a subject based upon the time-derived function.

14. The system of claim 13 further comprising a catheter which defines the catheter lumen.

15. The system of claim 13 wherein the elongate body comprises a stylet.

16. The system of claim 13 wherein the elongate body comprises a guidewire.

17. The system of claim 13 wherein the sensor is positioned at or distal to an opening of the catheter lumen.

18. The system of claim 13 wherein the sensor is positioned at the distal end of the elongate body.

19. The system of claim 13 wherein the sensor comprises a temperature sensor.

20. The system of claim 13 further comprising a conduit positioned at least partially within the catheter lumen.

21. The system of claim 20 wherein the elongate body is attached to the conduit.

22. The system of claim 13 wherein the sensor is positioned along a longitudinal axis of the catheter lumen.

23. The system of claim 13 wherein the sensor is positioned at a fixed distance relative to an opening of the catheter lumen.

24. The system of claim 13 further comprising an ECG electrode incorporated into the elongate body.

25. The system of claim 13 further comprising a pressure sensor incorporated into the elongate body.

26. The system of claim 13 further comprising a fluid reservoir in communication with the catheter lumen.

27. The system of claim 13 wherein sensor data is transmitted between the sensor and the controller.

28. The system of claim 27 wherein the sensor data comprises temperature data.

29. The system of claim 28 wherein the controller is configured to obtain a position of the sensor within a vasculature of the body of the subject based upon the temperature data.

30. The system of claim 13 wherein the time-derived function is based upon a degree of turbulence of the fluid after emitted from an opening of the catheter lumen.

* * * * *